US008673818B2

(12) United States Patent
Ruther et al.

(10) Patent No.: US 8,673,818 B2
(45) Date of Patent: Mar. 18, 2014

(54) C2-PHENYL-SUBSTITUTED CYCLIC KETONOLS

(75) Inventors: Michael Ruther, Leverkusen (DE); Hermann Hagemann, Leverkusen (DE); Udo Schneider, Leverkusen (DE); Markus Dollinger, Leverkusen (DE); Peter Dahmen, Neuss (DE); Ulrike Wachendorff-Neumann, Neuwied (DE); Reiner Fischer, Monheim (DE); Alan Graff, Leverkusen (DE); Thomas Bretschneider, Leverkusen (DE); Christoph Erdelen, Leichlingen (DE); Mark Wilhelm Drewes, Langenfeld (DE); Dieter Feucht, Eschborn (DE); Folker Lieb, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 13/455,416

(22) Filed: Apr. 25, 2012

(65) Prior Publication Data
US 2012/0238450 A1  Sep. 20, 2012

Related U.S. Application Data

(62) Division of application No. 13/029,497, filed on Feb. 17, 2011, now Pat. No. 8,193,120, which is a division of application No. 10/239,331, filed as application No. PCT/EP01/03215 on Mar. 21, 2001, now Pat. No. 7,915,282.

(30) Foreign Application Priority Data

Apr. 3, 2000 (DE) .................................. 100 16 544

(51) Int. Cl.
C07C 49/597 (2006.01)
C07C 69/003 (2006.01)
A01N 35/06 (2006.01)
A01N 37/10 (2006.01)

(52) U.S. Cl.
USPC ............ 504/318; 568/329; 568/376; 560/155

(58) Field of Classification Search
USPC ..................... 568/329, 376; 504/318; 560/155
See application file for complete search history.

(56) References Cited

U.S. PATENT DOCUMENTS

| | | |
|---|---|---|
| 3,542,809 A | 11/1970 | Nakanishi |
| 4,091,006 A | 5/1978 | Durden, Jr. et al. |
| 4,104,043 A | 8/1978 | Durden, Jr. et al. |
| 4,175,135 A | 11/1979 | Haines |
| 4,209,532 A | 6/1980 | Wheeler |
| 4,256,659 A | 3/1981 | Wheeler |
| 4,283,348 A | 8/1981 | Wheeler |
| 4,303,669 A | 12/1981 | D'Silva |
| 4,338,122 A | 7/1982 | Wheeler |
| 4,351,666 A | 9/1982 | Koerwer |
| 4,409,153 A | 10/1983 | Hodakowski |
| 4,422,870 A | 12/1983 | Wheeler |
| 4,436,666 A | 3/1984 | Wheeler |
| 4,484,942 A | 11/1984 | Kirino et al. |
| 4,526,723 A | 7/1985 | Wheeler et al. |
| 4,551,547 A | 11/1985 | Wheeler |

(Continued)

FOREIGN PATENT DOCUMENTS

| | | |
|---|---|---|
| CH | 1999 0001642 | 9/1999 |
| DE | 28 133 41 | 10/1978 |

(Continued)

OTHER PUBLICATIONS

Chemical Reviews, (month unavailable) 1953, pp. 237-416, "The Reactions of Aliphatic Acid Chlorides" by N. O. V. Sonntag.
Organikum, VEB Deutscher Verlag der Wissenschaften, Berlin, (month unavailable) 1977, p. 505 D.7.1.5. Reaktionen von Carbonsaeuren und Carbonsaeurenderivaten mit Basen.
Chem. Pharm. Bull., 15 (8) pp. 1120-1122, (month unavailable) 1967, "Studies on Antiviral Agents IV. Biological Activity of Tenuazonic Acid Derivatives" by S. Suzuki, F. Sano and H. Yuki.
The Journal of Antibiotics, vol. XXXVI, No. 11, Nov. 1983, pp. 1589-1591, "Synthesis and Biological Activities of Thiotetromycin Analogs" by K. Tsuzuki and S. Omura.

(Continued)

Primary Examiner — Kahsay Habte
(74) Attorney, Agent, or Firm — Miles & Stockbridge, P.C.

(57) ABSTRACT

The present invention relates to novel $C_2$-phenyl-substituted cyclic ketoenols of the formula

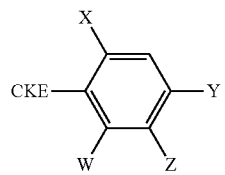

in which W is methyl, X is alkyl, alkenyl or alkinyl, Y is hydrogen, methyl, ethyl, i-propyl, alkenyl or alkinyl, and Z is hydrogen, alkyl, alkenyl or alkinyl, with the proviso that at least one of X, Y, or Z represents a chain having at least two carbon atoms and with the further proviso that X is not ethyl when Z is hydrogen and Y is methyl, and CKE represents the group

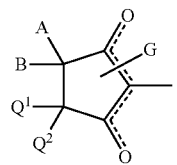

in which B is hydrogen, alkyl or alkoxyalkyl, A and $Q^1$ together are optionally substituted alkanediyl or alkenediyl, $Q^2$ is represents hydrogen or $C_1$-$C_4$-alkyl, and G represents hydrogen or an acyl or acyl-like group, to a plurality of processes for their preparation and to their use as pesticides and herbicides.

8 Claims, No Drawings

(56) References Cited

U.S. PATENT DOCUMENTS

| | | |
|---|---|---|
| 4,613,617 A | 9/1986 | Sousa |
| 4,632,698 A | 12/1986 | Wheeler |
| 4,659,372 A | 4/1987 | Wheeler |
| 4,925,868 A | 5/1990 | Terao et al. |
| 5,045,560 A | 9/1991 | Fischer et al. |
| 5,091,537 A | 2/1992 | Fischer et al. |
| 5,094,681 A | 3/1992 | Kraemer et al. |
| 5,116,836 A | 5/1992 | Fischer et al. |
| 5,186,737 A | 2/1993 | Fischer et al. |
| 5,207,817 A | 5/1993 | Kraemer et al. |
| 5,225,434 A | 7/1993 | Bertram et al. |
| 5,258,527 A | 11/1993 | Krauskopf et al. |
| 5,262,383 A | 11/1993 | Fischer et al. |
| 5,321,122 A | 6/1994 | Kuramoto et al. |
| 5,393,729 A | 2/1995 | Fischer et al. |
| 5,420,155 A | 5/1995 | Kulagowski et al. |
| 5,462,913 A | 10/1995 | Fischer et al. |
| 5,504,057 A | 4/1996 | Fischer et al. |
| 5,567,671 A | 10/1996 | Fischer et al. |
| 5,589,469 A | 12/1996 | Fischer et al. |
| 5,602,078 A | 2/1997 | Fischer et al. |
| 5,610,122 A | 3/1997 | Fischer et al. |
| 5,616,536 A | 4/1997 | Fischer et al. |
| 5,622,917 A | 4/1997 | Fischer et al. |
| 5,677,449 A | 10/1997 | Fischer et al. |
| 5,719,310 A | 2/1998 | Fischer et al. |
| 5,740,662 A | 4/1998 | Royneberg et al. |
| 5,808,135 A | 9/1998 | Fischer et al. |
| 5,830,825 A | 11/1998 | Fischer et al. |
| 5,830,826 A | 11/1998 | Fischer et al. |
| 5,840,661 A | 11/1998 | Fischer et al. |
| 5,847,211 A | 12/1998 | Fischer et al. |
| 5,945,444 A | 8/1999 | Fischer et al. |
| 5,977,029 A | 11/1999 | Fischer et al. |
| 5,981,567 A | 11/1999 | Fischer et al. |
| 5,994,274 A | 11/1999 | Fischer et al. |
| 6,051,723 A | 4/2000 | Fischer et al. |
| 6,071,937 A | 6/2000 | Bretschneider et al. |
| 6,110,872 A | 8/2000 | Lieb et al. |
| 6,114,374 A | 9/2000 | Lieb et al. |
| 6,133,296 A | 10/2000 | Lieb et al. |
| 6,140,358 A | 10/2000 | Lieb et al. |
| 6,150,304 A | 11/2000 | Fischer et al. |
| 6,172,255 B1 | 1/2001 | Fischer et al. |
| 6,200,932 B1 | 3/2001 | Fischer et al. |
| 6,251,830 B1 | 6/2001 | Fischer et al. |
| 6,251,833 B1 | 6/2001 | Erdelen et al. |
| 6,255,342 B1 | 7/2001 | Lieb et al. |
| 6,271,180 B2 | 8/2001 | Lieb et al. |
| 6,288,102 B1 | 9/2001 | Hagemann et al. |
| 6,316,486 B1 | 11/2001 | Lieb et al. |
| 6,359,151 B2 | 3/2002 | Lieb et al. |
| 6,380,246 B1 | 4/2002 | Lieb et al. |
| 6,388,123 B1 | 5/2002 | Lieb et al. |
| 6,391,912 B1 | 5/2002 | Hagemann et al. |
| 6,410,480 B1 | 6/2002 | Muehlebach et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,469,196 B2 | 10/2002 | Fischer et al. |
| 6,472,419 B1 | 10/2002 | Fischer et al. |
| 6,486,343 B1 | 11/2002 | Lieb et al. |
| 6,504,036 B1 | 1/2003 | Lieb et al. |
| 6,511,942 B1 | 1/2003 | Lieb et al. |
| 6,515,184 B1 | 2/2003 | Fischer et al. |
| 6,794,183 B2 | 9/2004 | Wildi et al. |
| 6,933,261 B2 | 8/2005 | Lieb et al. |
| 7,256,158 B2 | 8/2007 | Lieb et al. |
| 7,915,282 B2 | 3/2011 | Ruther et al. |
| 8,168,832 B2 | 5/2012 | Fischer et al. |
| 8,193,120 B2 * | 6/2012 | Ruther et al. ............ 504/318 |
| 2002/0010204 A1 | 1/2002 | Lieb et al. |
| 2002/0022575 A1 | 2/2002 | Fischer et al. |
| 2002/0072617 A1 | 6/2002 | Hagemann et al. |
| 2002/0161034 A1 | 10/2002 | Hagemann et al. |
| 2003/0073851 A1 | 4/2003 | Lieb et al. |
| 2003/0171219 A1 | 9/2003 | Lieb et al. |
| 2003/0216260 A1 | 11/2003 | Ruther et al. |
| 2005/0038021 A1 | 2/2005 | Lieb et al. |

FOREIGN PATENT DOCUMENTS

| | | |
|---|---|---|
| DE | 100 16 544 | 10/2001 |
| DE | 10016554 | 10/2001 |
| EP | 03 555 99 | 2/1990 |
| EP | 0456053 | 11/1991 |
| EP | 0456063 | 11/1991 |
| EP | 0528156 | 7/1992 |
| EP | 0596298 | 10/1993 |
| EP | 0647637 | 8/1994 |
| EP | 0706527 | 1/1995 |
| EP | 9501798 | 1/1995 |
| EP | 0837847 | 4/1998 |
| EP | 0915846 | 5/1999 |
| EP | 1280770 | 2/2003 |
| FR | 1374665 | 11/1963 |
| JP | 510256/96 | 10/1996 |
| JP | 505293/97 | 5/1997 |
| WO | 9426702 | 11/1994 |
| WO | 9514013 | 5/1995 |
| WO | 96/01798 | 1/1996 |
| WO | 9603366 | 2/1996 |
| WO | 96/25395 | 8/1996 |
| WO | 97/36868 | 10/1997 |
| WO | 98/05638 | 2/1998 |
| WO | 99/16748 | 4/1999 |
| WO | 99/24437 | 5/1999 |
| WO | 9947525 | 9/1999 |

OTHER PUBLICATIONS

Can. J. Chem., 53, (month unavailable) 1975, pp. 3339-3350, "Stereochemistry of the Bucherer-Bergs and Striker Reactions of 4-tert-Butylcyclohexanone" by J. T. Edward and C. Jitrangsri.

J. Chem. Soc., (month unavailable) 1961, pp. 4372-4379, "Aminoacids of the Cyclohexane Series. Part I." by L. Munday.

Organikum, VEB Deutscher Verlag der Wissenschaften, Berlin, (month unavailable) 1977, pp. 587-589, D.7.2.6. Esterkondensation.

Organikum, VEB Deutscher Verlag der Wissenschaften, Berlin, (month unavailable) 1977, pp. 517-581, D.7.1.5. Reaktionen von Carbonsaeuren und Carbonsaeurederivaten mit Basen.

Organic Preparations and Procedures Int., 7(4), pp. 155-158, (month unavailable) 1975, "Synthesis of Chlorocarbonyl Ketenes" by S. Naskanishi and K. Butler.

J. Chem. Soc., Chem. Commun., (month unavailable) 1987, pp. 1228-1230, "An Asymmetric Synthesis of Thiotetronic Acids using Chriality Transfer via an Allyl Xanthate-toDithiocarbonate Rearrangement. X-Ray Crystal Structure of (5R)-2,5-Dihydro-4-hydroxy-5-methyl-3-phenyl-5-prop-1'-enyl-2-oxothiophene" by M.S. Chambers, E. J. Thomas and D. J. Williams.

J. Chem. Soc. C, (month unavailable) 1967, pp. 405-409, "Constituents of the Higher Fungi. Part IV. Involutin, a Diphenyl-Cyclopenteneone from Paxillus involutus (Oeder ex Fries)" by R. L. Edwards, G. C. Elsworthy and N. Kale.

Arch. Pharm., 309, (month available) 1976, pp. 558-564, "Zur Synthese von Kawalactonderivaten" by A. M. Chirazi, T. Kappe and E. Ziegler.

J. Heterocycl. Chem., Apr. 10, 1973, pp. 223-228, "Synthesis of Heterocycles. 174 (1,2) Substituted Thiazines and Bisthiazinyls from Dithiooxamide and Trichlorophenyl Malonates" by R. Ketcham (3), Th. Kappe and E. Ziegler.

J. Chem. Soc., Perkin Trans. I, (month unavailable) 1985, pp. 1567-1576, "Synthesis of (E)- and (Z)-Pulvin" by A. C. Campbell, M. S. Maidment, J. H. Pick and D. F. M. Stevenson.

Liebigs Ann. Chem., (month unavailable) 1985, pp. 1095-1098, "Cyclisierung von N-Acylalanin-und N-Acylglycinestern" by R. Schmierer a and H. Mildenberger.

Indian J. Chem., 6, (month unavailable) 1968, pp. 341-345, "Isoquinoline Derivatives: Part XVIII—Formation of I-Alkyl-(or alkryl)-3-methyl-7-chloro-(or 5-chloro)-isoquinolines" by B. Bhattacharya.

(56) References Cited

OTHER PUBLICATIONS

Chemistry & Industry (London), Nov. 9, 1968, p. 1568, "Use of molecular sieves in the methyl esterification of carboxylic acids" by H. R. Harrison, W. M. Haynes, P. Arthur and E. J. Eisenbraum.
Chem. Ber., 91, (month unavailable) 1958, p. 2849, "Ringschluesse mit Malonsaeure-dicloriden" by K. H. Boltze and K. Heidenbluth.
J. Org. Chem., vol. 44, No. 26, (month unavailable) 1979, pp. 4906-4912, "Novel Photochemical Synthesis of 2-Aryl-1,3-cyclohexanediones" by T. N. Wheeler.
Tetrahedron Letters, vol. 27, No. 24, pp. 2763-2766, (month unavailable) 1986, "Dimethyl Arylmalonates From Cerium(IV) Ammonium Nitrate Promoted Reactions of Dimethyl Malonate With Aromatic Compounds in Methanol" by E. Baciocchi, D. Dell'Aira, and R. Ruzziconi.
Tetrahedron Letters, vol. 48, No. 36, pp. 7519-7526, (month unavailable) 1992, "Alkylation and Acylation of 5-Phenylsulphonyl- and 5-Cyanobutyrolactones" by J. Micklefield, M. H. Block and A. R. Battersby.
Monatsch, 95, (month unavailable) 1964, pp. 147-155, "Synthesen von Heterocyclen, 52. Mitt.: Ueber Derivate des 2-Phenyl-4-hydroxyl-[1,3-thiazinons-(6)]1" by E. Ziegler and E. Steiner.
Ann. Chim., (month unavailable) 1970, t. 5, pp. 11-22, "Addition Des Reactifs Nucleophiles Sur L'Hydrogene Selenie" by P. L. Compagnon and M. Miocque.
Journal of Economic Entomology, (month unavailable) 1973, pp. 584-586, vol. 66, No. 2, "Esters of 3-Hydroxy-2-Arylindones, a New Class of Acaricide1" by A. A. Sousa, J. A. Durden, Jr., and J. F. Stephen.
Houben-Weyl: Methoden der Organischen Chemie, vol. 8, (month unavailable) 1952, pp. 467-469, H. Henecka.
Organikum, 15th edition, Berlin (month unavailable) 1977, p. 499, D. 7. 3. 5. Reaktionen mit metallorganischen Verbindungen.
Organikum, 15th edition, Berlin (month unavailable) 1977, pp. 519-521, D. 7. 4. 2. Reaktionen vinyloger Biektronendonorverbindungen.
Jasna Peter-Katalinic et al., "Umwandlung von 6-Methylen-tricyclo [3.2.1. 02,7] oct-3-en-8-onen mit Ameisensaure in kermethyliarts Phenylassigsauren", Helvetica Chimica Acta, vol. 57, Fasc. 1 (1974), pp. 223-266.
B. Van Zanten et al., "Synthesis of Alkyl-Substituted 3-Phenyl-4 Hydroxycoumarins", Recueil de Travaux Chimiques, vol. 79, 1960, pp. 1211-1222.
European Patent Office, Notice of Opposition to European Patent No. EP 1 280770B1 (Bayer Aktiengesellschaft), Mar. 15, 2011.
Canadian Office Action based on Canadian Application No. 2,404,868 dated Dec. 18, 2009.
CAS Registry Database No. 100863-17-0; 2,4,6-Triethylbenzeneacetic Acid; Dated Mar. 15, 1986.
CAS Registry Database No. 100256-33-5; 2,6-Diethylbenzeneacetic Acid; Feb. 15, 1986.
CAS Registry Database No. 81598-12-1; 2-Ethenylbenzeneacetic Acid; Nov. 16, 1984.
CAS Registry Database No. 19418-96-3; 2-(1-Methylethyl)Benzeneacetic Acid; Nov. 16, 1984.
CAS Registry Database No. 6331-04-0; 2,4-Dimethylbenzeneacetic Acid; Nov. 16, 1984.
CAS Registry Database No. 166519-12-6; 2,6-Bis(1-Methylethyl)Benzeneacetyl; Aug. 18, 1995.
CAS Registry Database No. 90705-86-5; 2,4-Dimethylbenzeneacetyl Chloride; Nov. 16, 1984.
CAS Registry Database No. 79998-80-4; 2-(1-Methylethyl)Benzeneacetyl Chloride; Nov. 16, 1984.
CAS Registry Database No. 79929-33-2; 2,4,6-Trimethylbenzeneacetyl Iodide; Nov. 16, 1984.
CAS Registry Database No. 52629-47-7; 2-4-6-Tris(1-Methylethyl)Benzeneacetyl; Nov. 16, 1984.
CAS Registry Database No. 181129-75-9; 5-Methyl-2-(1-Methylethyl)Benzeneacetic Acid, Ethyl Ester; Sep. 24, 1996.
CAS Registry Database No. 170635-30-0; 4-Ethenyl-2-Methylbenzeneacetic Acid, 1,1-Dimethylethyl Ester; Nov. 28, 1995.
CAS Registry Database No. 169602-49-7; 2,4,6-Trimethylbenzeneacetic Acid, Butyl Ester; Nov. 3, 1995.
CAS Registry Database No. 105337-78-8; 2-Ethylbenzeneacetic Acid, Ethyl Ester; Nov. 22, 1986.
CAS Registry Database No. 105337-16-4; 2,4-Dimethylbenzeneacetic Acid, Ethyl Ester Nov. 22, 1986.
Canadian Office Action Based on Patent Application No. 2,404,868 Dated Dec. 18, 2009.
Opposition to EP 1 280 770 B1, documents dated May 20, 2013 and Apr. 19, 2013, 66 pages.
Allais, A., et al., "Derives de la serie des acides benzoylphenylacetiques anti-inflammatoires et analgesiques," Eur. J. Med. Chem.—Chimica Therapeutica, pp. 381-389, vol. 9, No. 4 (Jul.-Aug. 1974).
Wenner, W., "Hydolysis of Acrylacetonitriles," Contrubution No. 153 from the Research Laboratories of Hoffman-La Roche Inc., Journal of Organic Chemistry, pp. 548-551, vol. 15 (1950).
Casanova, J., et al., "The Neighboring Sulfonium Group in Ester Hydrolysis," Journal of the American Chemical Society, vol. 89(10):2411-2416 (May 10, 1967).
Fischer, R. and H.C. Weiss, "Spirotetramat (Movento®)—discovery, synthesis and physico-chemical properties," Bayer CropScience Journal 61:127-140 (2008).
Nauen, R., et al., "Biological profile of spirotetramat (Movento®)—a new two-way systemic (ambimobile) insecticide against sucking pest species," Bayer CropScience Journal 61:245-278 (2008).
Bruck, E., et al., "Movento®, an innovative ambimobile insecticide for sucking insect pest control in agriculture: Biological profile and field performance," Crop Protection 28:838-844 (2009).
English Translation of European Decision Revoking EP 1 280 770 which was filed as EP 01917102.4 dated Jul. 15, 2013.

* cited by examiner

C2-PHENYL-SUBSTITUTED CYCLIC KETONOLS

This application is a Divisional Application of U.S. application Ser No. 13/029,497, filed Feb. 17, 2011, which is a Divisional of U.S. Ser. No. 10/239,331, filed Dec. 16, 2002, now U.S. Pat. No. 7,915,282, which is a National Stage Application of PCT/EP01/03215, filed Mar. 21, 2001, which claim priority to German Application 100 16 544.3, filed Apr. 3, 2000, each hereby incorporated by reference in their entireties.

The present invention relates to novel $C_2$-phenyl-substituted cyclic ketoenols, to a plurality of processes for their preparation and to their use as pesticides and herbicides.

Pharmacological properties of 3-acyl-pyrrolidine-2,4-diones have already been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-aryl-pyrrolidine-2,4-diones) of which, however, no herbicidal, insecticidal or acaricidal activity has become known. Unsubstituted bicyclic 3-aryl-pyrrolidine-2,4-dione derivatives (EP-A-355 599 and EP-A-415 211) and substituted monocyclic 3-aryl-pyrrolidine-2,4-dione derivatives (EP-A-377 893 and EP-A-442 077) having herbicidal, insecticidal or acaricidal activity are known.

Also known are polycyclic 3-arylpyrrolidine-2,4-dione derivatives (EP-A-442 073) and 1H-arylpyrrolidine-dione derivatives (EP-A-456 063, EP-A-521 334, EP-A-596 298. EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868. WO 97/43275, WO 98/05638, WO 98/06721, WO 98/25928, WO 99/16748, WO 99/24437. WO 99/43649. WO 99/48869 and WO 99/55673).

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methyl-phenyl)-4-hydroxy-5-(4-fluorophenyl)-$\Delta^3$-dihydrofuran-2-one) is likewise described in DE-A-4 014420.

Compounds of a similar structure are known from the publication Campbell et al., J. Chem. Soc., Perkin Trans. 1, 1985, (8) 1567-76, without any insecticidal and/or acaricidal activity being mentioned. Furthermore, 3-aryl-$\Delta^3$-dihydrofuranone derivatives having herbicidal, acaricidal and insecticidal properties are known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869 and WO 99/55673. 3-Aryl-$\Delta^3$-dihydrothiphenone derivatives are likewise known (WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673).

Certain phenyl-pyrone derivatives which are unsubstituted in the phenyl ring have already become known (cf. A. M. Chirazi, T. Kappe and E. Ziegler, Arch. Pharm. 309, 558 (1976) and K.-H. Boltze and K. Heidenbluth, Chem. Ber. 91, 2849), a possible use of these compounds as pesticides not being mentioned. Phenyl-pyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869 and WO 99/55673.

Certain 5-phenyl-1,3-thiazine derivatives which are unsubstituted in the phenyl ring have already become known (cf. E. Ziegler and E. Steiner, Monatsh. 95, 147 (1964), R. Ketcham, T. Kappe and E. Ziegler, J. Heterocycl. Chem. 10, 223 (1973)), a possible use of these compounds as pesticides not being mentioned. 5-Phenyl-1,3-thiazine derivatives which are substituted in the phenyl ring and have herbicidal, acaricidal and insecticidal activity are described in WO 94/14 785, WO 96/02 539, WO 96/35 664, WO 97/01 535, WO 97/02 243, WO 97/02 243, WO 97/36 868, WO 99/05638, WO 99/43649, WO 99/48869 and WO 99/55673.

It is known that certain substituted 2-arylcyclopentanediones have herbicidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO 99/48869, WO 99/55673). Moreover, compounds of a similar structure are known; 3-hydroxy-5,5-dimethyl-2-phenylcyclo-pent-2-en-1-one from the publication Micklefield et al., Tetrahedron, (1992), 7519-26 and the natural product involutine (−)-cis-5-(3,4-dihydroxyphenyl)-3,4-dihydroxy-2-(4-hydroxyphenyl)-cyclopent-2-en-one from the publication Edwards et al., J. Chem. Soc. S, (1967), 405-9. An insecticidal or acaricidal activity is not described. Moreover, 2-(2,4,6-trimethylphenyl)-1,3-indanedione is known from the publication J. Economic Entomology, 66, (1973), 584 and the Offenlegungsschrift DE-A 2 361 084, with herbicidal and acaricidal activities being mentioned.

It is known that certain substituted 2-arylcyclohexanediones have herbicidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2 813 341, and also Wheeler, T. N., J. Org. Chem. 44, 4906 (1979)), WO 99/43649, WO 99/48869, WO 99/55673).

However, the activity and the activity spectrum of these compounds are, in particular at low application rates and concentrations, not always entirely satisfactory. Furthermore, the compatibility of these compounds with plants is not always sufficient.

This invention, accordingly, provides novel compounds of the formula (I)

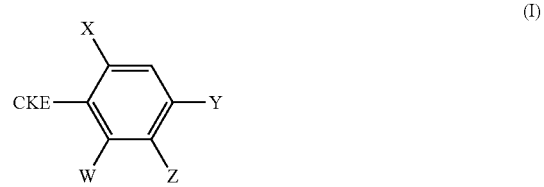

in which

W represents hydrogen, alkyl, alkenyl or alkinyl,

X represents alkyl, alkenyl or alkinyl,

Y represents hydrogen, methyl, ethyl, i-propyl, alkenyl or alkinyl,

Z represents hydrogen, alkyl, alkenyl or alkinyl, with the proviso that at least one of the radicals W, X, Y or Z represents a chain having at least two carbon atoms, CKE represents one of the groups

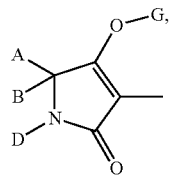  (1)

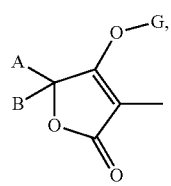  (2)

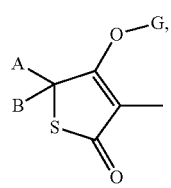  (3)

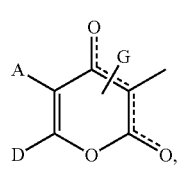  (4)

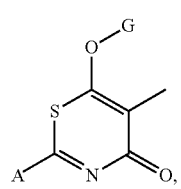  (5)

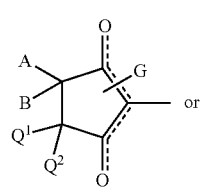  (6)

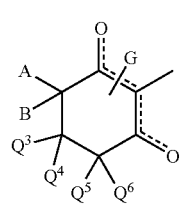  (7)

in which

A represents hydrogen, represents in each case optionally halogen-substituted alkyl, alkenyl, alkoxyalkyl, alkylthioalkyl, represents saturated or unsaturated, optionally substituted cycloalkyl in which optionally at least one ring atom is replaced by a heteroatom, or represents in each case optionally halogen-, alkyl-, halogenoalkyl-, alkoxy-, halogenoalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated unsubstituted or substituted cycle which optionally contains at least one heteroatom, D represents hydrogen or represents an optionally substituted radical from the group consisting of alkyl, alkenyl, alkinyl, alkoxyalkyl, saturated or unsaturated cycloalkyl in which optionally one or more ring members are replaced by heteroatoms, arylalkyl, aryl, hetarylalkyl and hetaryl or A and D together with the atoms to which they are attached represent a saturated or unsaturated cycle which is unsubstituted or substituted in the A,D moiety and which optionally contains at least one heteroatom, or A and $Q^1$ together represent alkanediyl or alkenediyl, each of which is optionally substituted by hydroxyl or by in each case optionally substituted alkyl, alkoxy, alkylthio, cycloalkyl, benzyloxy or aryl or $Q^1$ represents hydrogen or alkyl, $Q^2$, $Q^4$, $Q^5$ and $Q^6$ independently of one another each represent hydrogen or alkyl, $Q^3$ represents hydrogen, alkyl, alkoxyalkyl, alkylthioalkyl, optionally substituted cycloalkyl (in which optionally one methylene group is replaced by oxygen or sulphur) or optionally substituted phenyl, or $Q^3$ and $Q^4$ together with the carbon atom to which they are attached represent a saturated or unsaturated unsubstituted or substituted cycle which optionally contains a heteroatom, G represents hydrogen (a) or represents one of the groups

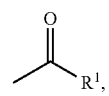  (b)

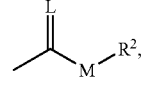  (c)

  (d)

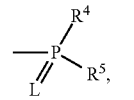  (e)

E or  (f)

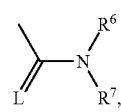  (g)

in which

E represents a metal ion equivalent or an ammonium ion,

L represents oxygen or sulphur,

M represents oxygen or sulphur,

R¹ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, R² represents in each case optionally halogen-substituted alkyl, alkenyl, alkoxyalkyl, polyalkoxyalkyl or represents in each case optionally substituted cycloalkyl, phenyl or benzyl, R³, R⁴ and R⁵ independently of one another each represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio, R⁶ and R⁷ independently of one another each represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur.

Depending, inter alia, on the nature of the substituents, the compounds of the formula (I) can be present as geometrical and/or optical isomers or mixtures of isomers in varying compositions, which can be separated, if desired, in a customary manner. The present invention provides both the pure isomers and the isomer mixtures, their preparation and use and also compositions comprising them. In the following, for simplicity, however, the compounds of the formula (I) are always referred to, although both pure compounds and, if appropriate, mixtures having different proportions of isomeric compounds are intended.

Including the meanings (1) to (7) of the group CKE, the following principal structures (I-1) to (I-7) result:

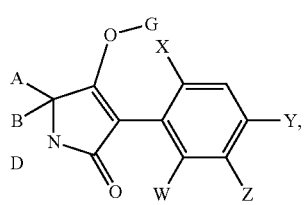
(I-1)

(I-2)

(I-3)

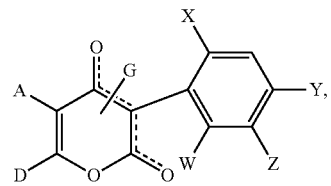
(I-4)

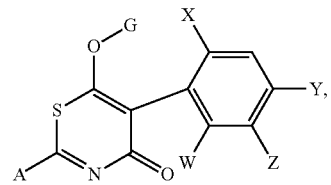
(I-5)

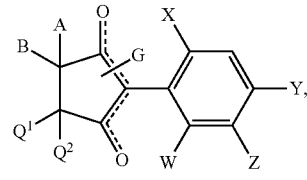
(I-6)

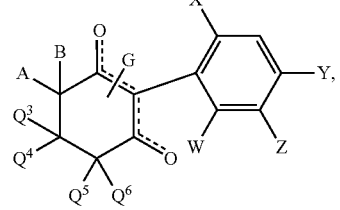
(I-7)

in which

A, B, D, G, Q¹, Q², Q³, Q⁴, Q⁵, Q⁶, W, X, Y and Z are each as defined above.

Including the various meanings of (a), (b), (c), (d), (e), (f) and (g) of the group G, the following principal structures (I-1-a) to (I-1-g) result if CKE represents the group (1):

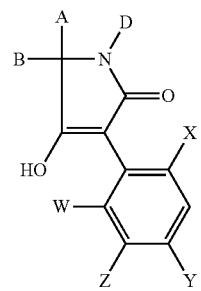
(I-1-a)

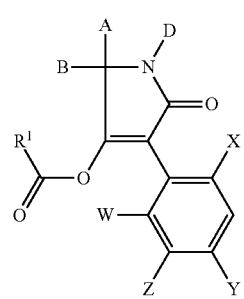
(I-1-b)

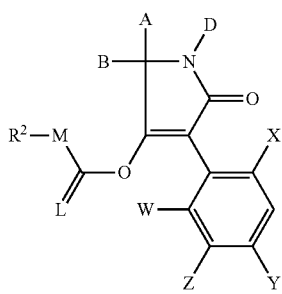
(I-1-c)
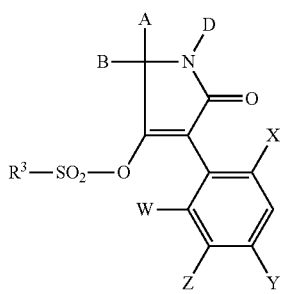
(I-1-d)
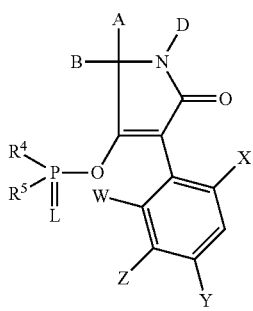
(I-1-e)
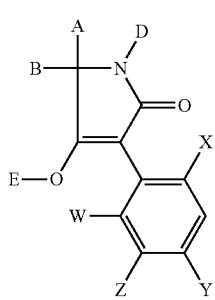
(I-1-f)
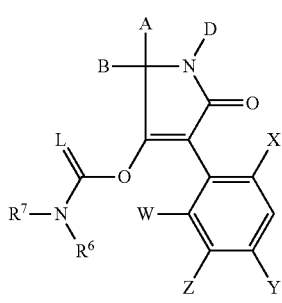
(I-1-g)
in which
A, B, D, E, L, M, W, X, Y, Z, $R^1$, $R^2$, $R^3$, $R^4$, $R^5$, $R^6$ and $R^7$ are each as defined above.
Including the various meanings (a), (b), (c), (d), (e), (f) and (g) of the group G, the following principal structures (I-2-a) to (I-2-g) result if CKE represents the group (2):
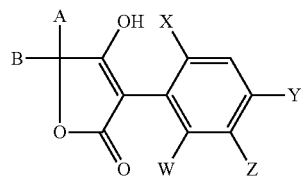
(I-2-a)
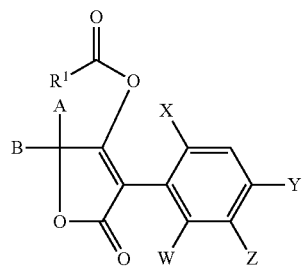
(I-2-b)
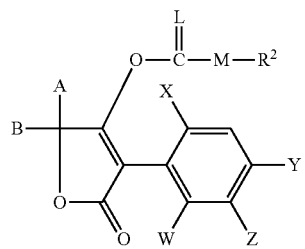
(I-2-c)
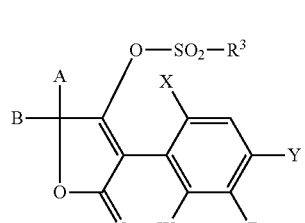
(I-2-d)
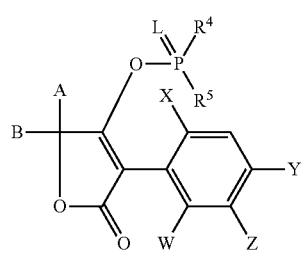
(I-2-e)
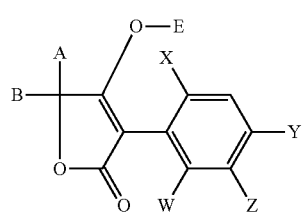
(I-2-f)

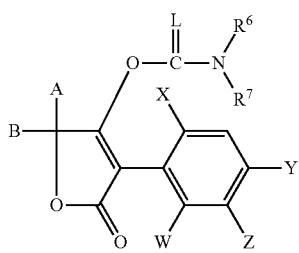
(I-2-g)

in which

A, B, E, L, M, W, X, Y, Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-3-a) to (I-3-g) result if CKE represents the group (3): (I-3-a): (I-3-b):

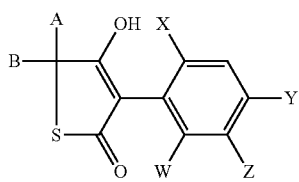
(I-3-a)

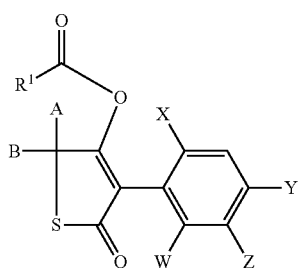
(I-3-b)

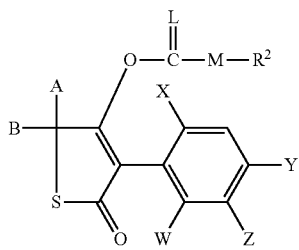
(I-3-c)

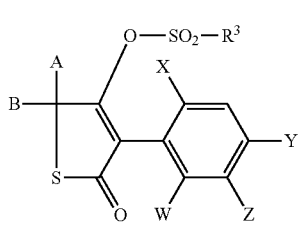
(I-3-d)

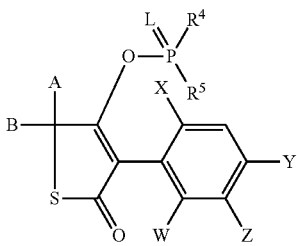
(I-3-e)

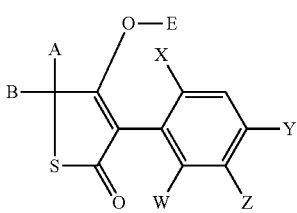
(I-3-f)

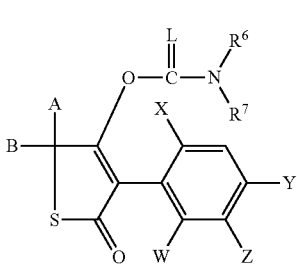
(I-3-g)

in which

A, B, E, L, M, W, X, Y, Z, $R^1$, $R^2$, $R^3$, $R^4$, $R^5$, $R^6$ and $R^7$ are each as defined above.

Depending on the position of the substituent G, the compounds of the formula (I-4) can be present in two isomeric forms of the formulae (I-5-A) and (I-5-B)

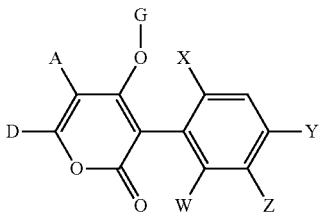
(I-4-A)

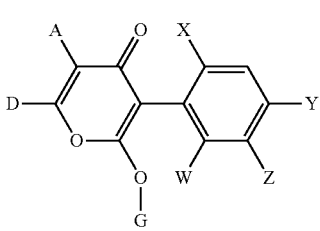
(I-4-B)

which is meant to be indicated by the dashed line in the formula (I-4).

The compounds of the formulae (I-4-A) and (I-4-B) can be present both as mixtures and in the form of their pure isomers. Mixtures of the compounds of the formulae (I-4-A) and (I-4-B) can be separated, if desired, in a known manner by physical methods, for example by chromatographic methods.

For reasons of clarity, hereinbelow in each case only one of the possible isomers is given. This does not exclude that the compounds may, if appropriate, be present in the form of the isomer mixtures or in the respective other isomeric form.

Including the various meanings (a), (b), (c), (d), (e), (f) and (g) of the group G, the following principal structures (I-4-a) to (I-4-g) result if CKE represents the group (4): (I-4-a): (I-4-b):

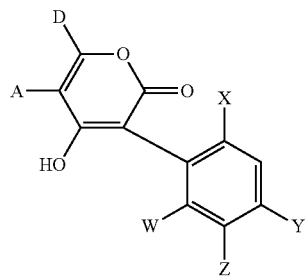
(I-4-a)

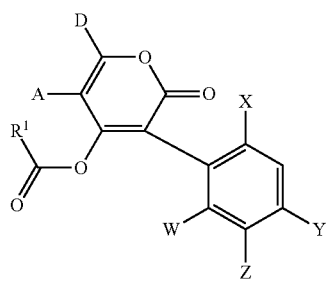
(I-4-b)

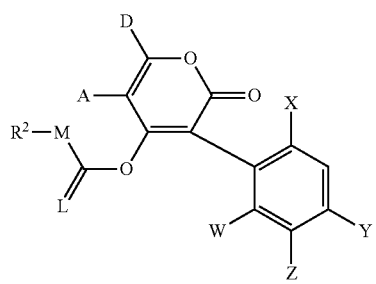
(I-4-c)

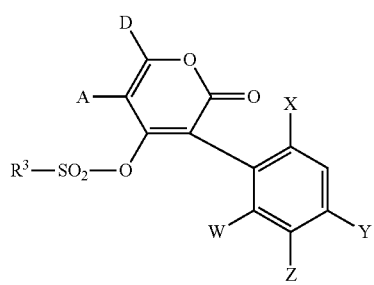
(I-4-d)

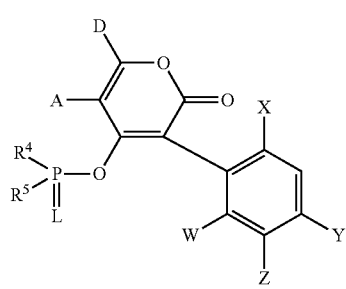
(I-4-e)

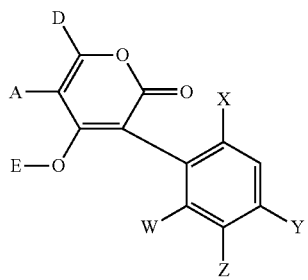
(I-4-f)

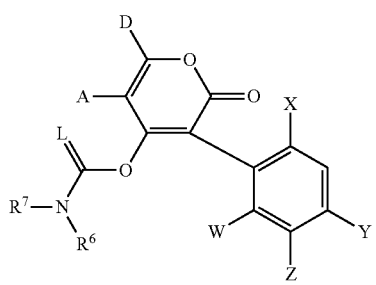
(I-4-g)

in which
A, D, E, L, M, W, X, Y, Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-5-a) to (I-5-g) result if CKE represents the group (5): (I-5-a): (I-5-b):

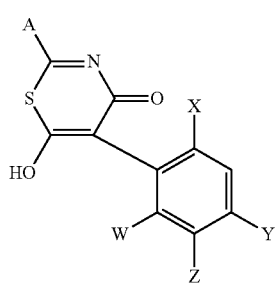
(I-5-a)

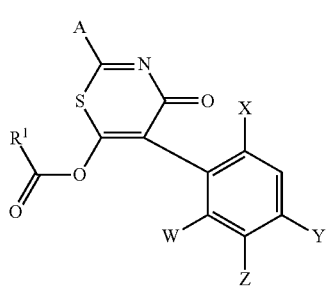
(I-5-b)

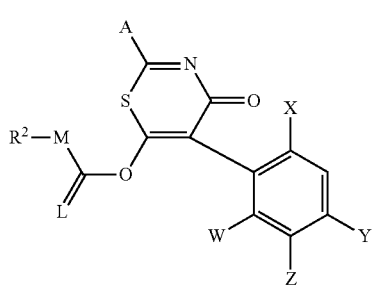
(I-5-c)

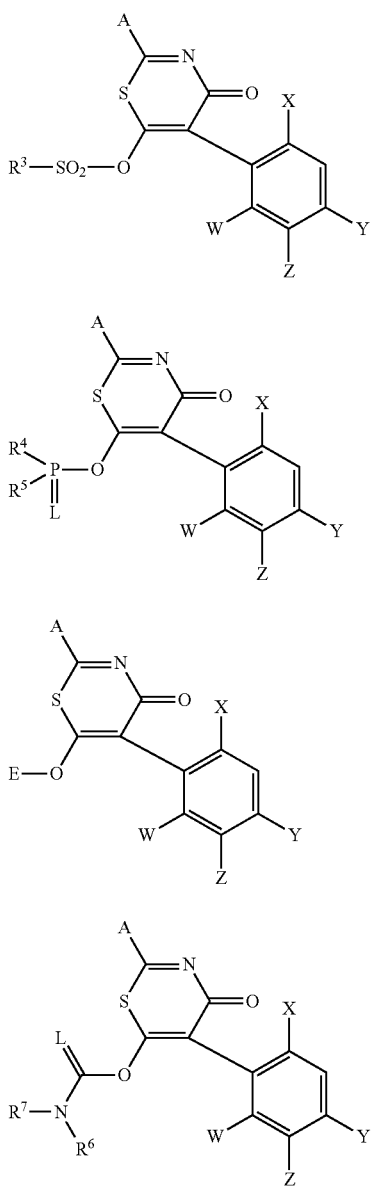

in which

A, E, L, M, W, X, Y, Z, $R^1$, $R^2$, $R^3$, $R^4$, $R^5$, $R^6$ and $R^7$ are each as defined above.

Depending on the position of the substituent G, the compounds of the formula (I-6) can be present in the two isomeric forms of the formula (I-6-A) and (I-6-B)

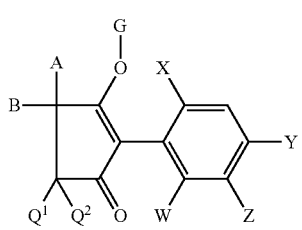

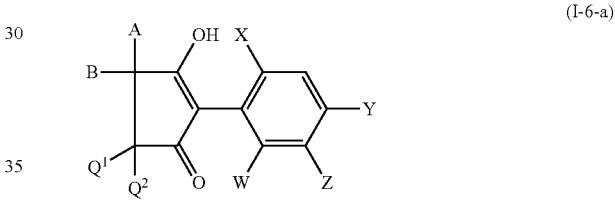

which is meant to be indicated by the dashed line in the formula (I).

The compounds of the formulae (I-6-A) and (I-6-B) can be present both as mixtures and in the form of their pure isomers. Mixtures of the compounds of the formulae (I-6-A) and (I-6-B) can be separated, if desired, by physical methods, for example by chromatographic methods.

For reasons of clarity, hereinbelow in each case only one of the possible isomers is given. This does not exclude that the compounds may, if appropriate, be present in the form of the isomer mixtures or in the respective other isomeric form.

Including the various meanings (a), (b), (c), (d), (e), (f) and (g) of the group G, the following principal structures (I-6-a) to (I-6-g) result:

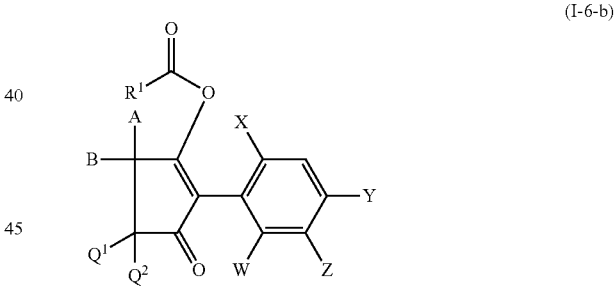

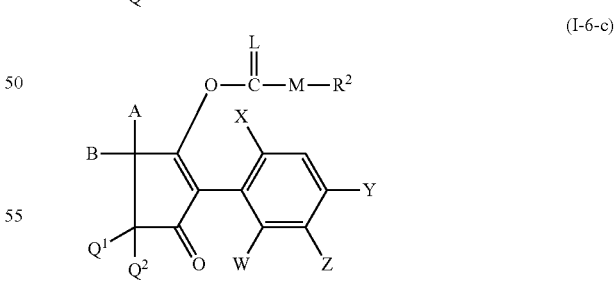

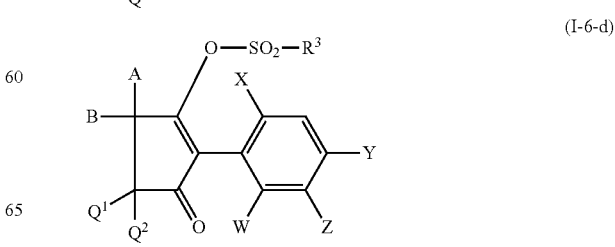

-continued

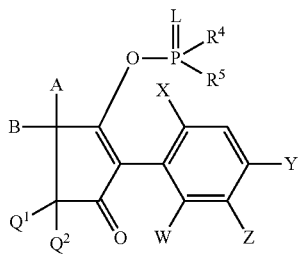
(I-6-e)

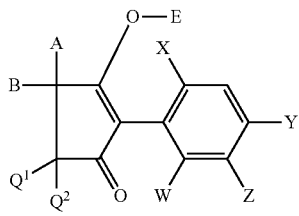
(I-6-f)

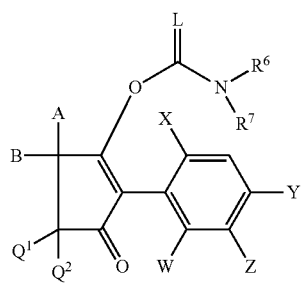
(I-6-g)

in which

A, B, Q$^1$, Q$^2$, E, L, M, W, X, Y, Z, R$^1$, R$^2$, R$^3$, R$^4$, R$^5$, R$^6$ and R$^7$ are each as defined above.

Depending on the position of the substituent G, the compounds of the formula (I-7) can be present in two isomeric forms of the formulae (I-7-A) and (I-7-B) which is meant to be indicated by the dashed line in the formula (I-7):

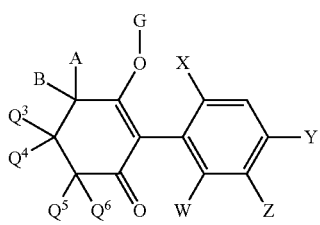
(I-7-A)

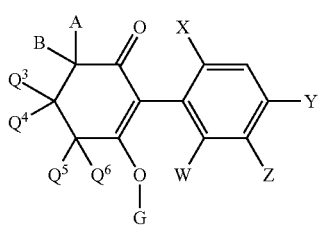
(I-7-B)

The compounds of the formulae (I-7-A) and (I-7-B) can be present both as mixtures and in the form of their pure isomers. Mixtures of the compounds of the formulae (I-7-A) and (I-7-B) can be separated, if desired, by physical methods, for example by chromatographic methods.

For reasons of clarity, hereinbelow in each case only one of the possible isomers is given. This does not exclude that the compound may, if appropriate, be present in the form of the isomer mixture or in the respective other isomeric form.

Including the various meanings (a), (b), (c), (d), (e), (f) and (g) of the group G, the following principal structures (I-7-a) to (I-7-g) result:

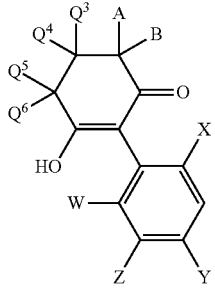
(I-7-a)

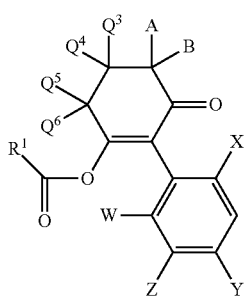
(I-7-b)

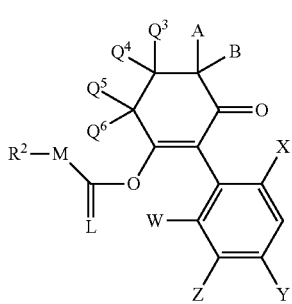
(I-7-c)

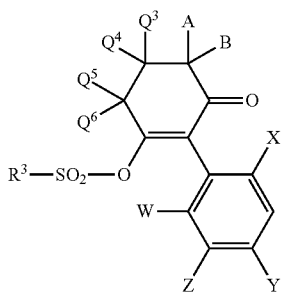
(I-7-d)

-continued (I-7-e)

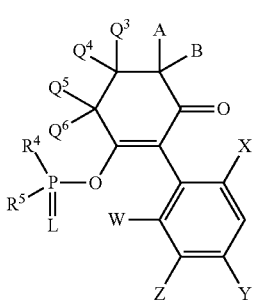

(I-7-f)

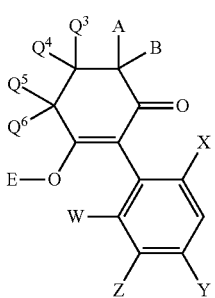

(I-7-g)

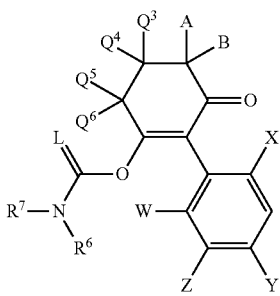

in which
A, B, E, L, M, $Q^3$, $Q^4$, $Q^5$, $Q^6$, W, X, Y, Z, $R^1$, $R^2$, $R^3$, $R^4$, $R^5$, $R^6$ and $R^7$ are each as defined above.

Furthermore, it has been found that the novel compounds of the formula (I) are obtained by one of the processes described below:

(A) Substituted 3-phenylpyrrolidine-2,4-diones or their enols of the formula (I-1-a)

(I-1-a)

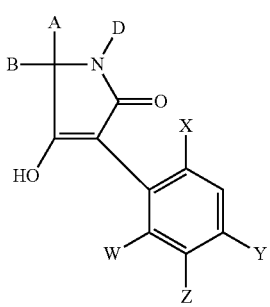

in which

A, B, D, W, X, Y and Z are each as defined above are obtained when

N-acylamino acid esters of the formula (II)

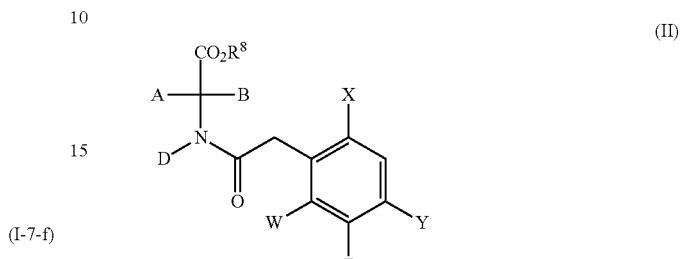

(II)

in which

A, B, D, W, X, Y and Z are each as defined above
and $R^8$ represents alkyl (preferably $C_1$-$C_6$-alkyl), are condensed intramolecularly in the presence of a diluent and in the presence of a base.

(B) Moreover, it has been found that substituted 3-phenyl-4-hydroxy-$\Delta^3$-di-hydrofuranone derivatives of the formula (I-2-a)

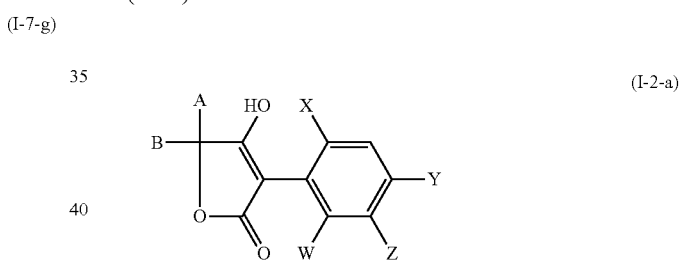

(I-2-a)

in which

A, B, W, X, Y and Z are each as defined above are obtained when carboxylic esters of the formula (III)

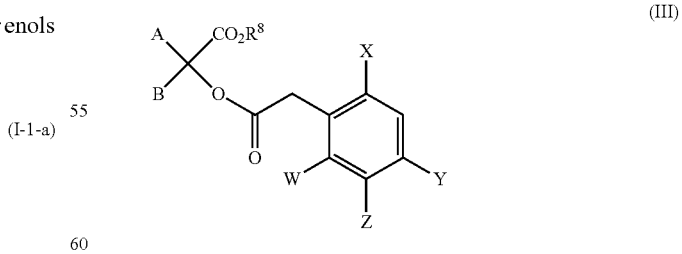

(III)

in which

A, B, W, X, Y, Z and $R^8$ are each as defined above are condensed intramolecularly in the presence of a diluent and in the presence of a base.

(C) Furthermore, it has been found that substituted 3-phenyl-4-hydroxy-Δ³-di-hydrothiophenone derivatives of the formula (I-3-a)

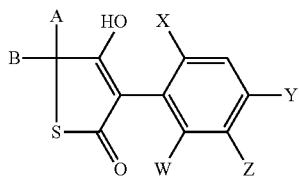
(I-3-a)

in which
A, B, W, X, Y and Z are each as defined above
are obtained when
β-ketocarboxylic esters of the formula (IV)

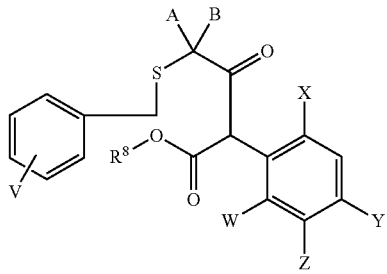
(IV)

in which
A, B, W, X, Y, Z and $R^8$ are each as defined above and
V represents hydrogen, halogen, alkyl (preferably $C_1$-$C_6$-alkyl) or alkoxy (preferably $C_1$-$C_8$-alkoxy)
are cyclized intramolecularly, if appropriate in the presence of a diluent and in the presence of an acid.

(D) Furthermore, it has been found that the novel substituted 3-phenylpyrone derivatives of the formula (I-4-a)

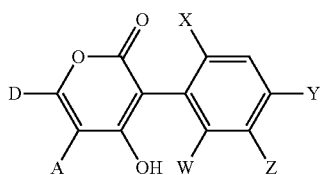
(I-4-a)

in which
A, D, W, X, Y and Z are each as defined above
are obtained when
carbonyl compounds of the formula (V)

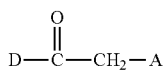
(V)

in which
A and D are each as defined above or their silyl enol ethers of the formula (Va)

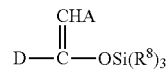
(Va)

in which
A, D and $R^8$ are each as defined above
are reacted with ketene acid halides of the formula (VI)

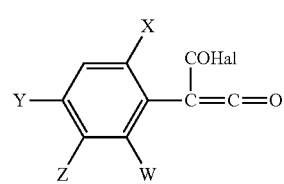
(VI)

in which
W, X, Y and Z are each as defined above and
Hal represents halogen (preferably chlorine or bromine),
if appropriate in the presence of a diluent and if appropriate in the presence of an acid acceptor.

Furthermore, it has been found
(E) that the novel substituted phenyl-1,3-thiazine derivatives of the formula (I-5-a)

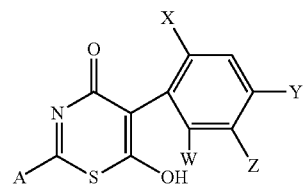
(I-5-a)

in which
A, W, X, Y and Z are each as defined above are obtained when
thioamides of the formula (VII)

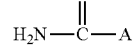
(VII)

in which
A is as defined above are reacted with ketene acid halides of the formula (VI)

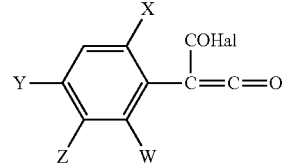
(VI)

in which

Hal, W, X, Y and Z are each as defined above, if appropriate in the presence of a diluent and if appropriate in the presence of an acid acceptor.

Furthermore, it has been found (F) that compounds of the formula (I-6-a)

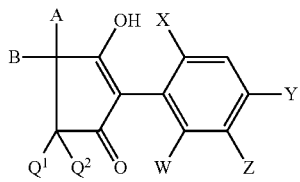
(I-6-a)

in which

A, B, $Q^1$, $Q^2$, W, X, Y and Z are each as defined above are obtained when ketocarboxylic esters of the formula (VIII)

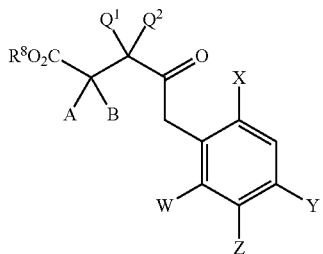
(VIII)

in which

A, B, $Q^1$, $Q^2$, W, X, Y and Z are each as defined above and $R^8$ represents alkyl (in particular $C_1$-$C_8$-alkyl)

are cyclized intramolecularly, if appropriate in the presence of a diluent and in the presence of a base.

Moreover, it has been found (G) that compounds of the formula (I-7-a)

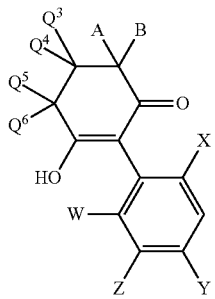
(I-7-a)

in which

A, B, $Q^3$, $Q^4$, $Q^5$, $Q^6$, W, X, Y and Z are each as defined above are obtained when 6-aryl-5-keto-hexanoic esters of the formula (IX)

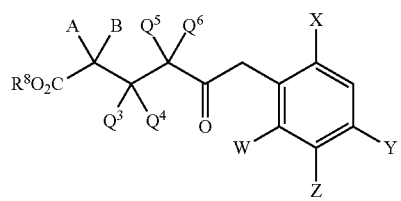
(IX)

in which

A, B, $Q^3$, $Q^4$, $Q^5$, $Q^6$, W, X, Y and Z are each as defined above and $R^8$ represents alkyl (preferably $C_1$-$C_6$-alkyl)

are condensed intramolecularly in the presence of a diluent and in the presence of a base;

(H) that compounds of the formulae (I-1(a-g)) to (I-7(a-g)) shown above in which A, B, D, G, $Q^1$, $Q^2$, $Q^3$, $Q^4$, $Q^5$, $Q^6$, W, X, Y and Z are each as defined above, where one, at most two, radicals W, X, Y or Z represent $R^{22}$—C=C— or

$R^{22}$ represents hydrogen or $C_1$-$C_4$-alkyl, preferably hydrogen or $C_1$-$C_2$-alkyl and particularly preferably hydrogen, are obtained when compounds of the formulae (I-1'(a-g)) to (I-7'(a-g)),

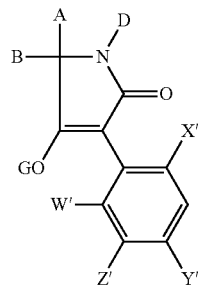
(I-1')

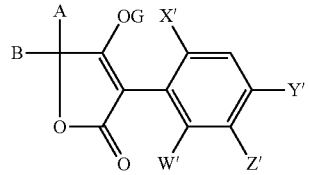
(I-2')

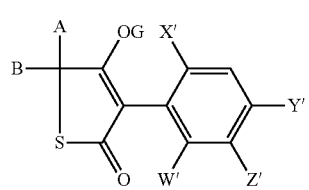
(I-3')

-continued (I-4')

[chemical structure]

(I-5')

[chemical structure]

(I-6')

[chemical structure]

(I-7')

[chemical structure]

in which

A, B, D, G, $Q^1$, $Q^2$, $Q^3$, $Q^4$, $Q^5$, $Q^6$, W', X', Y' and Z' are each as defined above and where the apostrophe ' means that one, at most two, radicals W, X, Y and Z in this process represent chlorine, bromine, iodine, preferably bromine, with the proviso that the other radicals W, X, Y or Z do not represent alkenyl or alkinyl are reacted with silylacetylenes of the formula (X-a) or vinylstannanes of the formula (X-b)

$$R^{22}-C\equiv C-Si(Alk)(Alk)(R^{21}) \quad (X\text{-a})$$

$$R^{22}\text{-}HC=CH\text{-}Sn(Alk)(Alk)(Alk) \quad (X\text{-b})$$

in which alk preferably represents $C_1$-$C_4$-alkyl and $R^{21}$ preferably represents $C_1$-$C_4$-alkyl or phenyl, $R^{22}$ preferably represents hydrogen or $C_1$-$C_4$-alkyl, particularly preferably hydrogen or $C_1$-$C_2$-alkyl and very particularly preferably hydrogen, in the presence of a solvent, if appropriate in the presence of a base and a catalyst, particularly suitable catalysts being palladium complexes.

Moreover, it has been found (I) that the compounds of the formulae (I-1-b) to (I-7-b) shown above in which A, B, D, $Q^1$, $Q^2$, $Q^3$, $Q^4$, $Q^5$, $Q^6$, $R^1$, W, X, Y and Z are each as defined above are obtained when compounds of the formulae (I-1-a) to (I-7-a) shown above in which A, B, D, $Q^1$, $Q^2$, $Q^3$, $Q^4$, $Q^5$, $Q^6$, W, X, Y and Z are each as defined above are in each case (α) reacted with acid halides of the formula (XI)

$$\text{Hal}-\underset{\underset{O}{\|}}{C}-R^1 \quad (XI)$$

in which $R^1$ is as defined above and

Hal represents halogen (in particular chlorine or bromine) or (β) reacted with carboxylic anhydrides of the formula (XII)

$$R^1\text{—CO—O—CO—}R^1 \quad (XII)$$

in which $R^1$ is as defined above, if appropriate in the presence of a diluent and if appropriate in the presence of an acid binder;

(J) that the compounds of the formulae (I-1-c) to (I-7-c) shown above in which A, B, D, $Q^1$, $Q^2$, $Q^3$, $Q^4$, $Q^5$, $Q^6$, $R^2$, M, W, X, Y and Z are each as defined above and L represents oxygen are obtained when compounds of the formulae (I-1-a) to (I-7-a) shown above in which A, B, D, $Q^1$, $Q^2$, $Q^3$, $Q^4$, $Q^5$, $Q^6$, W, X, Y and Z are each as defined above are in each case reacted with chloroformic esters or chloroformic thioesters of the formula (XIII)

$$R^2\text{-M-CO—Cl} \quad (XIII)$$

in which $R^2$ and M are each as defined above, if appropriate in the presence of a diluent and if appropriate in the presence of an acid binder;

(K) that compounds of the formulae (I-1-c) to (I-7-c) shown above in which A, B, D, $Q^1$, $Q^2$, $Q^3$, $Q^4$, $Q^5$, $Q^6$, $R^2$, M, W, X, Y and Z are in each case as defined above and L represents sulphur are obtained when compounds of the formulae (I-1-a) to (I-7-a) shown above in which A, B, D, $Q^1$, $Q^2$, $Q^3$, $Q^4$, $Q^5$, $Q^6$, W, X, Y and Z are in each case as defined above are in each case reacted with chloromonothioformic esters or chlorodithioformic esters of the formula (XIV)

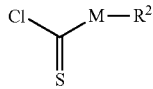  (XIV)

in which
M and $R^2$ are each as defined above,
if appropriate in the presence of a diluent and if appropriate in the presence of an acid binder
and
(L) that compounds of the formulae (I-1-d) to (I-7-d) shown above in which A, B, D, $Q^1$, $Q^2$, $Q^3$, $Q^4$, $Q^5$, $Q^6$, $R^3$, W, X, Y and Z are each as defined above are obtained when compounds of the formulae (I-Ia) to (I-7-a) shown above in which A, B, D, $Q^1$, $Q^2$, $Q^3$, $Q^4$, $Q^5$, $Q^6$, W, X, Y and Z are each as defined above are in each case
reacted with sulphonyl chlorides of the formula (XV)

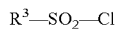  (XV)

in which
$R^3$ is as defined above,
if appropriate in the presence of a diluent and if appropriate in the presence of an acid binder,
(M) that compounds of the formulae (I-1-e) to (I-7-e) shown above in which A, B, D, L, $Q^1$, $Q^2$, $Q^3$, $Q^4$, $Q^5$, $Q^6$, $R^4$, $R^5$, W, X, Y and Z are each as defined above are obtained when compounds of the formulae (I-1-a) to (I-7-a) shown above in which A, B, D, $Q^1$, $Q^2$, $Q^3$, $Q^4$, $Q^5$, $Q^6$, W, X, Y and Z are each as defined above are in each case reacted with phosphorus compounds of the formula (XVI)

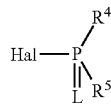  (XVI)

in which
L, $R^4$ and $R^5$ are each as defined above and
Hal represents halogen (in particular chlorine or bromine),
if appropriate in the presence of a diluent and if appropriate in the presence of an acid binder,
(N) that compounds of the formulae (I-1-f) to (I-7-f) shown above in which A, B, D, E, $Q^1$, $Q^2$, $Q^3$, $Q^4$, $Q^5$, $Q^6$, W, X, Y and Z are each as defined above are obtained when compounds of the formulae (I-1-a) to (I-7-a) shown above in which A, B, D, $Q^1$, $Q^2$, $Q^3$, $Q^4$, $Q^5$, $Q^6$, W, X, Y and Z are each as defined above are in each case
reacted with metal compounds or amines of the formulae (XVII) or (XVIII)

  (XVII)

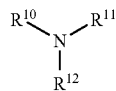  (XVIII)

in which
Me represents a mono- or divalent metal (preferably an alkali metal or alkaline earth metal, such as lithium, sodium, potassium, magnesium or calcium),
t represents the number 1 or 2,
$R^{10}$, $R^{11}$, $R^{12}$ independently of one another each represents hydrogen or alkyl (preferably $C_1$-$C_8$-alkyl),
if appropriate in the presence of a diluent,
(O) that compounds of the formulae (I-1-g) to (I-7-g) shown above in which A, B, D, L, $Q^1$, $Q^2$, $Q^3$, $Q^4$, $Q^5$, $Q^6$, $R^6$, $R^7$, W, X, Y and Z are each as defined above are obtained when compounds of the formulae (I-1-a) to (I-7-a) shown above in which A, B, D, $Q^1$, $Q^2$, $Q^3$, $Q^4$, $Q^5$, $Q^6$, W, X, Y and Z are each as defined above are in each case
(α) reacted with isocyanates or isothiocyanates of the formula (XIX)

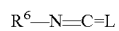  (XIX)

in which
$R^6$ and L are each as defined above,
if appropriate in the presence of a diluent and if appropriate in the presence of a catalyst, or
(β) reacted with carbamoyl chlorides or thiocarbamoyl chlorides of the formula (XX)

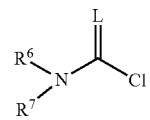  (XX)

in which
L, $R^6$ and $R^7$ are each as defined above,
if appropriate in the presence of a diluent and if appropriate in the presence of an acid binder.

Furthermore, it has been found that the novel compounds of the formula (I) have very good activity as pesticides, preferably as insecticides, acaricides and herbicides.

The formula (I) provides a general definition of the compounds according to the invention. Preferred substituents or ranges of the radicals listed in the formulae mentioned hereinabove and hereinbelow are illustrated below.

W preferably represents hydrogen, C t-$C_6$-alkyl, $C_2$-$C_6$-alkenyl or ethinyl.
X preferably represents $C_1$-$C_6$-alkyl, $C_2$-$C_6$-alkenyl or ethinyl.
Y preferably represents hydrogen, methyl, ethyl, i-propyl, $C_2$-$C_6$-alkenyl or ethinyl.
Z preferably represents hydrogen, $C_1$-$C_6$-alkyl, $C_2$-$C_6$-alkenyl or ethinyl
with the proviso that at least one of the radicals W, X, Y and Z represents a chain having at least two carbon atoms.
CKE preferably represents one of the groups

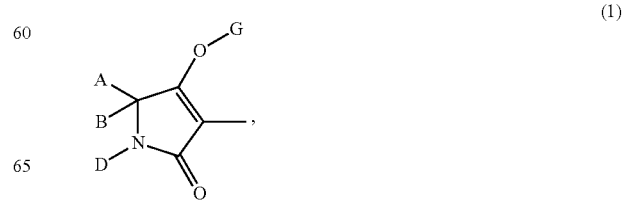  (1)

-continued

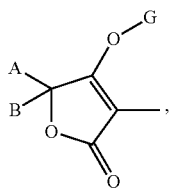

(2)

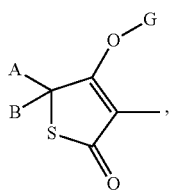

(3)

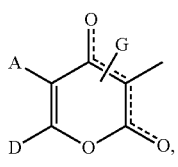

(4)

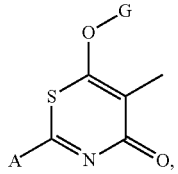

(5)

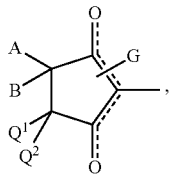

(6)

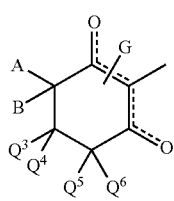

(7)

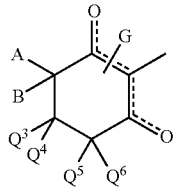

A preferably represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulphur or represents in each case optionally halogen-, $C_1$-$C_6$-alkyl-, $C_1$-$C_6$-halogenoalkyl-, $C_1$-$C_6$-alkoxy-, $C_1$-$C_6$-halogenoalkoxy-, cyano- or nitro-substituted phenyl or naphthyl, hetaryl having 5 to 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl.

B preferably represents hydrogen, $C_1$-$C_{12}$-alkyl or $C_1$-$C_8$-alkoxy-$C_1$-$C_6$-alkyl, or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_8$-alkyl, $C_3$-$C_{10}$-cycloalkyl, $C_1$-$C_8$-halogenoalkyl, $C_1$-$C_8$-alkoxy, $C_1$-$C_8$-alkylthio, halogen or phenyl, or A, B and the carbon atom to which they are attached preferably represent $C_3$-$C_6$-cycloalkyl which is substituted by an alkylenediyl group which optionally contains one or two not directly adjacent oxygen and/or sulphur atoms and which is optionally $C_1$-$C_4$-alkyl-substituted, or by an alkylenedioxyl group or by alkenedithioyl group which, together with the carbon atom to which it is attached, forms a further five- to eight-membered ring, or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl in which optionally one methylene group is replaced by oxygen or sulphur.

D preferably represents hydrogen, in each case optionally halogen-substituted $C_1$-$C_{12}$-alkyl, $C_3$-$C_8$-alkenyl, $C_3$-$C_8$-alkinyl, $C_1$-$C_{10}$-alkoxy-$C_2$-$C_8$-alkyl optionally halogen-, $C_1$-$C_4$-alkyl-, $C_1$-$C_4$-alkoxy- or $C_1$-$C_4$-halogenoalkyl-substituted $C_3$-$C_8$-cycloalkyl in which optionally one ring member is replaced by oxygen or sulphur or in each case optionally halogen-, $C_1$-$C_6$-alkyl-, $C_1$-$C_6$-halogenoalkyl-, $C_1$-$C_6$-alkoxy-, $C_1$-$C_6$-halogenoalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazoyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazoyl), or A and D together represent in each case optionally substituted $C_3$-$C_6$-alkanediyl or $C_3$-$C_6$-alkenediyl in which optionally one methylene group is replaced by a carbonyl group, oxygen or sulphur, possible substituents being in each case: halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compound of the formula (I-1), A and D, together with the atoms to which they are attached, then represent, for example, the groups AD-1 to AD-10 mentioned further below) which cycle may contain oxygen or sulphur, or which may optionally contain one of the groups below

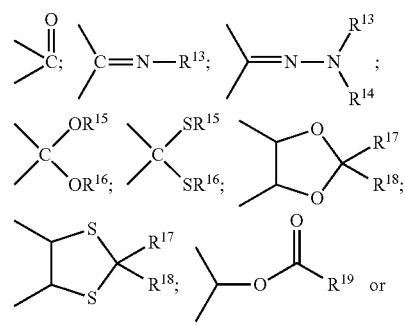

-continued or

A and $Q^1$ preferably together represent $C_3$-$C_6$-alkanediyl or $C_4$-$C_6$-alkenediyl, each of which is optionally mono- or disubstituted by identical or different substituents selected from the group consisting of halogen, hydroxyl, $C_1$-$C_{10}$-alkyl, $C_1$-$C_6$-alkoxy, $C_1$-$C_6$-alkylthio, $C_3$-$C_7$-cycloalkyl, each of which is optionally mono- to trisubstituted by identical or different halogens, and benzyloxy and phenyl, each of which is optionally mono- to trisubstituted by identical or different substituents selected from the group consisting of halogen, $C_1$-$C_6$-alkyl and $C_1$-$C_6$-alkoxy, and which furthermore optionally contains one of the groups below or is bridged by a $C_1$-$C_2$-alkanediyl group or by an oxygen atom, or $Q^1$ preferably represents hydrogen or $C_1$-$C_4$-alkyl.

$Q^2$, $Q^4$, $Q^5$ and $Q^6$ independently of one another each preferably represent hydrogen or $C_1$-$C_4$-alkyl.

$Q^3$ preferably represents hydrogen, $C_1$-$C_6$-alkyl, $C_1$-$C_6$-alkoxy-$C_1$-$C_2$-alkyl, $C_1$-$C_6$-alkylthio-$C_1$-$C_2$-alkyl, optionally $C_1$-$C_4$-alkyl- or $C_1$-$C_4$-alkoxy-substituted $C_3$-$C_8$-cycloalkyl in which optionally one methylene group is replaced by oxygen or sulphur or optionally halogen-, $C_1$-$C_4$-alkyl-, $C_1$-$C_4$-alkoxy-, $C_1$-$C_2$-halogenoalkyl-, $C_1$-$C_2$-halogenoalkoxy-, cyano- or nitro-substituted phenyl, or $Q^3$ and $Q^4$ together with the carbon atom to which they are attached preferably represent an optionally $C_1$-$C_4$-alkyl-, $C_1$-$C_4$-alkoxy- or $C_1$-$C_2$-halogenoalkyl-substituted $C_3$-$C_7$-ring in which optionally one ring member is replaced by oxygen or sulphur.

G preferably represents hydrogen (a) or represents one of the groups (b)

(c)

(d)

(e)

(f)

(g)

in particular (a), (b), (c) or (g)
in which
E represents a metal ion equivalent or an ammonium ion,
L represents oxygen or sulphur and
M represents oxygen or sulphur.

$R^1$ particularly preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl or $C_1$-$C_6$-alkoxy-substituted $C_3$-$C_8$-cycloalkyl in which optionally one or more (preferably not more than two) not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-halogenoalkyl-, $C_1$-$C_6$-halogenoalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-halogenoalkyl- or $C_1$-$C_6$-halogenoalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl). $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-halogenoalkyl- or $C_1$-$C_6$-halogenoalkoxy-substituted phenyl or benzyl.

$R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-halogenoalkyl-, $C_1$-$C_4$-halogenoalkoxy-, cyano- or nitro-substituted phenyl or benzyl.

$R^4$ and $R^5$ independently of one another each preferably represent in each case optionally halogen-substituted $C_1$-$C_8$-alkyl, $C_1$-$C_8$-alkoxy, $C_1$-$C_8$-alkyl-amino, di-($C_1$-$C_8$-alkyl) amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkyl- or $C_1$-$C_4$-halogenoalkyl-substituted phenyl, phenoxy or phenylthio.

$R^6$ and $R^7$ independently of one another each preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-halogenoalkyl-, $C_1$-$C_8$-alkyl- or $C_1$-$C_8$-alkoxy-substituted phenyl, optionally halogen-, $C_1$-$C_8$-alkyl-, $C_1$-$C_8$-halogenoalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulphur.

$R^{13}$ preferably represents hydrogen, represents in each case optionally halogen-substituted $C_1$-$C_8$-alkyl or $C_1$-$C_8$-alkoxy, represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or represents in each case optionally halogen-, $C_1$-$C_6$-alkyl $C_1$-$C_6$-alkoxy-, $C_1$-$C_4$-halogenoalkyl-, $C_1$-$C_4$-halogenoalkoxy-, nitro- or cyano-substituted phenyl, phenyl-$C_1$-$C_4$-alkyl or phenyl-$C_1$-$C_4$-alkoxy.

$R^{14}$ preferably represents hydrogen or $C_1$-$C_8$-alkyl, or $R^{13}$ and $R^{14}$ together preferably represent $C_4$-$C_6$-alkanediyl.

$R^{15}$ and $R^{16}$ are identical or different and each preferably represents $C_1$-$C_6$-alkyl, or $R^{15}$ and $R^{16}$ together preferably represent a $C_2$-$C_4$-alkanediyl radical which is optionally substituted by $C_1$-$C_6$-alkyl, $C_1$-$C_6$-halogenoalkyl or by optionally halogen-, $C_1$-$C_6$-alkyl-, $C_1$-$C_4$-halogenoalkyl-, $C_1$-$C_6$-alkoxy-, $C_1$-$C_4$-halogenoalkoxy-, nitro- or cyano-substituted phenyl.

$R^{17}$ and $R^{18}$ independently of one another each preferably represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-halogenoalkyl-, $C_1$-$C_4$-halogenoalkoxy-, nitro- or cyano-substituted phenyl, or $R^{17}$ and $R^{18}$ together with the carbon atom to which they are attached preferably represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur.

$R^{19}$ and $R^{20}$ independently of one another each particularly preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl) amino.

W particularly preferably represents hydrogen, $C_1$-$C_4$-alkyl, $C_2$-$C_4$-alkenyl or ethinyl.

X particularly preferably represents $C_1$-$C_4$-alkyl, $C_2$-$C_4$-alkenyl or ethinyl.

Y particularly preferably represents hydrogen, methyl, ethyl, i-propyl, $C_2$-$C_4$-alkenyl or ethinyl.

Z particularly preferably represents $C_1$-$C_4$-alkyl, $C_2$-$C_4$-alkenyl or ethinyl with the proviso that at least one of the radicals W, X, Y or Z represents a chain having at least two carbon atoms, where at most only one of the radicals W, X, Y or Z may represent $C_2$-$C_4$-alkenyl or ethinyl.

CKE particularly preferably represents one of the groups

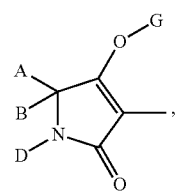
(1)

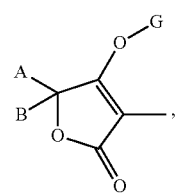
(2)

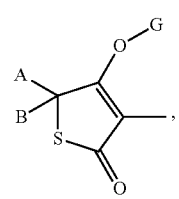
(3)

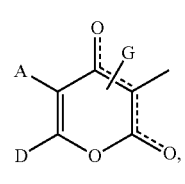
(4)

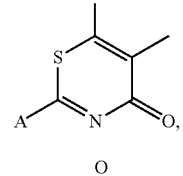
(5)

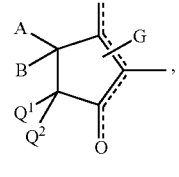
(6)

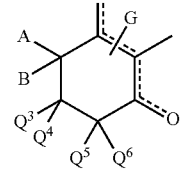
(7)

A particularly preferably represents in each case optionally fluorine- or chlorine-substituted $C_1$-$C_6$-alkyl, $C_1$-$C_4$-alkoxy-$C_1$-$C_2$-alkyl, optionally $C_1$-$C_2$-alkyl- or $C_1$-$C_2$-alkoxy-substituted $C_3$-$C_6$-cycloalkyl or (but not in the case of the compounds of the formulae (I-4), (I-6) and (I-7)) in each case optionally fluorine-, chlorine-, bromine-, $C_1$-$C_4$- alkyl-, $C_1$-$C_2$-halogenoalkyl-, $C_1$-$C_4$-alkoxy-, $C_1$-$C_2$-halogenoalkoxy-, cyano- or nitro-substituted phenyl or benzyl.

B particularly preferably represents hydrogen or $C_1$-$C_4$-alkyl, or

A, B and the carbon atom to which they are attached particularly preferably represent saturated or unsaturated $C_5$-$C_7$-cycloalkyl in which optionally one ring member is replaced by oxygen or sulphur and which is optionally monosubstituted by $C_1$-$C_6$-alkyl, trifluoromethyl or $C_1$-$C_6$-alkoxy, or A, B and the carbon atom to which they are attached particularly preferably represent $C_5$-$C_6$-cycloalkyl which is substituted by an alkylenediyl group which optionally contains one or two not directly adjacent oxygen and/or sulphur atoms and which is optionally methyl- or ethyl-substituted, or by an alkylenedioxyl group or by an alkylenedithiol group which, together with the carbon atom to which it is attached, forms a further 5- or 6-membered ring, or A, B and the carbon atom to which they are attached particularly preferably represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl.

D particularly preferably represents hydrogen, represents in each case optionally fluorine-substituted $C_1$-$C_6$-alkyl, $C_3$-$C_6$-alkenyl, $C_1$-$C_4$-alkoxy-$C_2$-$C_3$-alkyl, represents optionally $C_1$-$C_4$-alkyl-, $C_1$-$C_4$-alkoxy- or $C_1$-$C_2$-halogenoalkyl-substituted $C_3$-$C_6$-cycloalkyl in which optionally one methylene group is replaced by oxygen or (but not in the case of the compounds of the formula (I-1)) represents phenyl or pyridyl, each of which is optionally mono- or disubstituted by substituents selected from the group consisting of fluorine, chlorine, bromine, $C_1$-$C_4$-alkyl, $C_1$-$C_4$-halogenoalkyl, $C_1$-$C_4$-alkoxy and $C_1$-$C_4$-halogenoalkoxy, or A and D together particularly preferably represent optionally substituted $C_3$-$C_5$-alkanediyl in which one methylene group may be replaced by a carbonyl group (but not in the case of the compounds of the formula (I-1)), by oxygen or by sulphur, possible substituents being $C_1$-$C_2$-alkyl, or A and D (in the case of the compounds of the formula (I-1)) together with the atoms to which they are attached represent one of the groups AD-1 to AD-10:

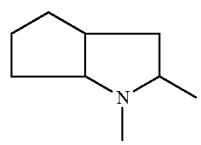
AD-1

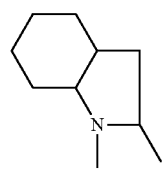
AD-2

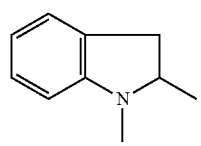
AD-3

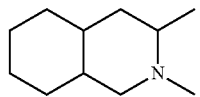
AD-4

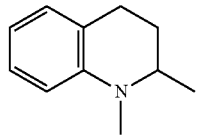
AD-5

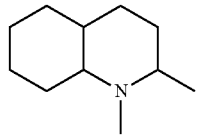
AD-6

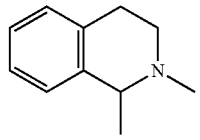
AD-7

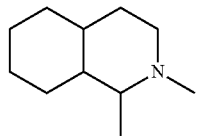
AD-8

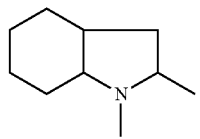
AD-9

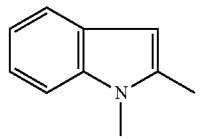
AD-10 or

A and $Q^1$ together particularly preferably represent $C_3$-$C_4$-alkanediyl which is optionally mono- or disubstituted by identical or different substituents selected from the group consisting of $C_1$-$C_2$-alkyl and $C_1$-$C_2$-alkoxy, or $Q^1$ particularly preferably represents hydrogen.

$Q^2$ particularly preferably represents hydrogen.

$Q^4$, $Q^5$ and $Q^6$ independently of one another each particularly preferably represent hydrogen or $C_1$-$C_3$-alkyl.

$Q^3$ particularly preferably represents hydrogen, $C_1$-$C_4$-alkyl or represents $C_3$-$C_6$-cycloalkyl which is optionally mono- or disubstituted by methyl or methoxy, or $Q^3$ and $Q^4$ together with the carbon to which they are attached particularly preferably represent an optionally $C_1$-$C_2$-alkyl- or $C_1$-$C_2$-alkoxy-substituted saturated $C_5$-$C_6$-membered ring in which optionally one ring member is replaced by oxygen or sulphur.

G particularly preferably represents hydrogen (a) or represents one of the groups

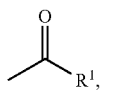  (b)

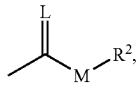  (c)

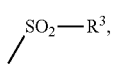  (d)

  (e)

E  or  (f)

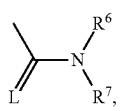  (g)

in particular (a), (b) or (c),
in which
E represents a metal ion equivalent or an ammonium ion,
L represents oxygen or sulphur and
M represents oxygen or sulphur.

$R^1$ particularly preferably represents in each case optionally fluorine- or chlorine-substituted $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl or optionally fluorine-, chlorine-, $C_1$-$C_2$-alkyl- or $C_1$-$C_2$-alkoxy-substituted $C_3$-$C_6$-cycloalkyl in which optionally one or two not directly adjacent ring members are replaced by oxygen,
represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-halogenoalkyl or $C_1$-$C_2$-halogenoalkoxy, $R^2$ particularly preferably represents in each case optionally fluorine-substituted $C_1$-$C_8$-alkyl, $C_2$-$C_8$-alkenyl or $C_1$-$C_4$-alkoxy-$C_2$-$C_4$-alkyl,
represents optionally $C_1$-$C_2$-alkyl- or $C_1$-$C_2$-alkoxy-substituted $C_3$-$C_6$-cycloalkyl or
represents phenyl or benzyl, each of which is optionally monosubstituted by fluorine, chlorine, bromine, cyano, nitro, $C_1$-$C_4$-alkyl, $C_1$-$C_3$-alkoxy, trifluoromethyl or trifluoromethoxy.

$R^3$ particularly preferably represents optionally fluorine-substituted $C_1$-$C_6$-alkyl or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ particularly preferably represents $C_1$-$C_6$-alkyl, $C_1$-$C_6$-alkoxy, $C_1$-$C_6$-alkyl-amino, di-($C_1$-$C_6$-alkyl)amino, $C_1$-$C_6$-alkylthio, $C_3$-$C_4$-alkenylthio, $C_3$-$C_6$-cycloalkylthio or represents phenyl, phenoxy or phenylthio, each of which is optionally monosubstituted by fluorine, chlorine, bromine, nitro, cyano, $C_1$-$C_3$-alkoxy, $C_1$-$C_3$-halogenoalkoxy, $C_1$-$C_3$-alkylthio, $C_1$-$C_3$-halogenoalkylthio, $C_1$-$C_3$-alkyl or trifluoromethyl.

$R^5$ particularly preferably represents $C_1$-$C_6$-alkoxy or $C_1$-$C_6$-alkylthio.

$R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy.

$R^7$ particularly preferably represents $C_1$-$C_6$-alkyl, $C_3$-$C_6$-alkenyl or $C_1$-$C_6$-alkoxy-$C_1$-$C_4$-alkyl.

$R^6$ and $R^7$ together particularly preferably represent an optionally methyl- or ethyl-substituted $C_5$-alkylene radical in which optionally one methylene group is replaced by oxygen or sulphur.

In the radical definitions mentioned as being particularly preferred, halogen represents fluorine, chlorine, bromine and iodine, and in particular fluorine, chlorine and bromine.

W very particularly preferably represents hydrogen, methyl, ethyl, i-propyl, vinyl or ethinyl.

X very particularly preferably represents methyl, ethyl, n-propyl, iso-propyl, vinyl or ethinyl, Y very particularly preferably represents hydrogen, methyl, ethyl, i-propyl, vinyl or ethinyl.

Z very particularly preferably represents hydrogen, methyl, ethyl, n-propyl, i-butyl, vinyl or ethinyl, with the proviso that at least one of the radicals W, X, Y or Z represents a chain having at least two carbon atoms where at most only one of the radicals W, X, Y or Z may represent vinyl or ethinyl, CKE very particularly preferably represents one of the groups

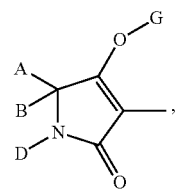  (1)

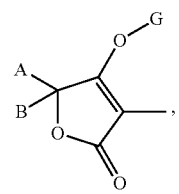  (2)

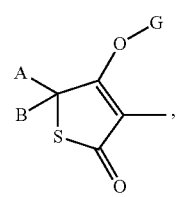  (3)

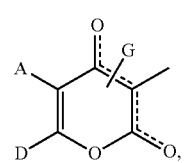  (4)

-continued

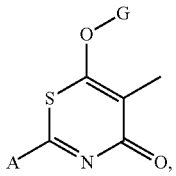
(5)

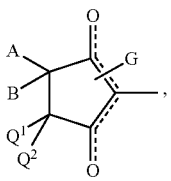
(6)

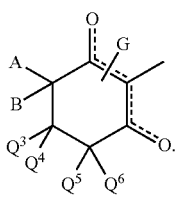
(7)

A very particularly preferably represents in each case optionally fluorine-substituted $C_1$-$C_4$-alkyl or $C_1$-$C_2$-alkoxy-$C_1$-$C_2$-alkyl, cyclopropyl, cyclopentyl or cyclohexyl and, only in the case of the compounds of the formula (I-5), represents optionally fluorine-, chlorine-, bromine-, methyl-, ethyl-, n-propyl-, iso-propyl-, methoxy-, ethoxy-, trifluoromethyl-, trifluoromethoxy-, cyano- or nitro-substituted phenyl.

B very particularly preferably represents hydrogen, methyl or ethyl, or

A, B and the carbon atom to which they are attached very particularly preferably represent saturated $C_5$-$C_6$-cycloalkyl in which optionally one ring member is replaced by oxygen or sulphur and which is optionally monosubstituted by methyl, ethyl, propyl, isopropyl, trifluoromethyl, methoxy, ethoxy, propoxy or butoxy or A, B and the carbon atom to which they are attached very particularly preferably represent $C_6$-cycloalkyl which is substituted by an alkylenedioxyl group which contains two oxygen atoms which are not directly adjacent, or A, B and the carbon atom to which they are attached represent $C_5$-$C_6$-cycloalkyl or $C_5$-$C_6$-cycloalkenyl in which two substituents together with the carbon atoms to which they are attached very particularly preferably represent $C_2$-$C_4$-alkanediyl or $C_1$-$C_4$-alkenediyl or butadienediyl.

D very particularly preferably represents hydrogen, represents in each case optionally fluorine-substituted $C_1$-$C_4$-alkyl, $C_3$-$C_4$-alkenyl, $C_1$-$C_4$-alkoxy-$C_2$-$C_3$-alkyl, cyclopropyl, cyclopentyl or cyclohexyl or (but not in the case of the compounds of the formula (I-1)) represents pyridyl or phenyl which is optionally monosubstituted by fluorine, chlorine, methyl, ethyl, n-propyl, iso-propyl, methoxy, ethoxy or trifluoromethyl, or A and D together very particularly preferably represent optionally substituted $C_3$-$C_4$-alkanediyl in which optionally one carbon atom is replaced by oxygen or sulphur A and $Q^1$ together very particularly preferably represent $C_3$-$C_4$-alkanediyl which is optionally mono- or disubstituted by methyl or methoxy, or $Q^1$ very particularly preferably represents hydrogen.

$Q^2$ very particularly preferably represents hydrogen.

$Q^4$, $Q^5$ and $Q^6$ independently of one another each very particularly preferably represent hydrogen or methyl.

$Q^3$ very particularly preferably represents hydrogen, methyl, ethyl or propyl, or $Q^3$ and $Q^4$ together with the carbon to which they are attached very particularly preferably represent a saturated $C_5$-$C_6$-ring which is optionally monosubstituted by methyl or methoxy.

G very particularly preferably represents hydrogen (a) or represents one of the groups

(b)

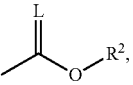
(c)

in which

L represents oxygen or sulphur and

M represents oxygen or sulphur.

$R^1$ very particularly preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl or cyclohexyl or cyclopropyl which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ very particularly preferably represents in each case optionally fluorine-substituted $C_1$-$C_8$-alkyl, $C_2$-$C_6$-alkenyl or $C_1$-$C_4$-alkoxy-$C_2$-$C_3$-alkyl, phenyl or benzyl.

W most particularly preferably represents hydrogen, methyl, ethyl or i-propyl,

X most particularly preferably represents methyl, ethyl, i-propyl or vinyl,

Y most particularly preferably represents hydrogen, methyl, ethyl, i-propyl, vinyl or ethinyl, Z most particularly preferably represents hydrogen, methyl, ethyl, n-propyl or i-butyl, with the proviso that at least one of the radicals W, X, Y or Z represents a chain having at least two carbon atoms, where at most only one of the radicals W, X, Y or Z may represent vinyl or ethinyl, CKE most particularly preferably represents one of the groups

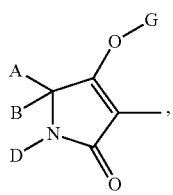
(1)

-continued

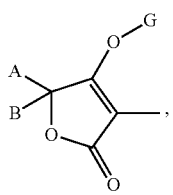
(2)

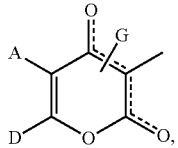
(4)

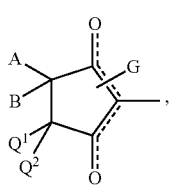
(6)

A most particularly preferably represents methyl,
B most particularly preferably represents methyl,
A, B and the carbon atoms to which they are attached most particularly preferably represent saturated $C_5$-$C_6$-cycloalkyl in which optionally one ring member is replaced by oxygen and which is optionally monosubstituted by methyl, ethyl, methoxy, ethoxy.
A and B together represent

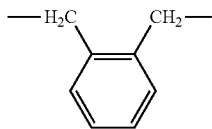

D most particularly preferably represents hydrogen or (but not in the case of the compound of the formula (I-1)) represents fluorine-substituted phenyl,
G most particularly preferably represents hydrogen (a) or represents one of the groups

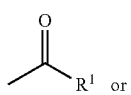
(b)

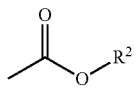
(c)

$R^1$ most particularly preferably represents $C_1$-$C_6$-alkyl, $C_1$-$C_2$-alkoxymethyl,
$R^2$ most particularly preferably represents $C_1$-$C_4$-alkyl.
For CKE=(6)
A and $Q^1$ together most particularly preferably represent $C_3$-$C_4$-alkanediyl and
B and $Q^2$ each most particularly preferably represent hydrogen.

The abovementioned general or preferred radical definitions or illustrations can be combined with each other as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preference according to the invention is given to the compounds of the formula (I) which contain a combination of the meanings listed above as being most preferred.

Saturated or unsaturated hydrocarbon radicals such as alkyl or alkenyl may in each case be straight-chain or branched as far as this is possible, including in combination with heteroatoms, such as, for example, in alkoxy.

Unless stated otherwise, optionally substituted radicals may be mono- or polysubstituted and, in the case of polysubstitutions, the substituents may be identical or different.

Besides the compounds mentioned in the Preparation Examples, the following compounds of the formula (I-1-a) may be specifically mentioned:

TABLE 1

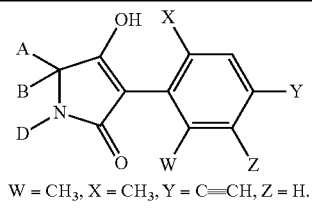

W = $CH_3$, X = $CH_3$, Y = C≡CH, Z = H.

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| △— | $CH_3$ | H |
| ⬠— | $CH_3$ | H |
| ⬡— | $CH_3$ | H |

TABLE 1-continued

[Structure: pyrrolinone with OH, A, B, D(N), =O, and phenyl ring with X, Y, W, Z substituents]

W = CH$_3$, X = CH$_3$, Y = C≡CH, Z = H.

| A | B | D |
|---|---|---|
| —(CH$_2$)$_2$— | | H |
| —(CH$_2$)$_4$— | | H |
| —(CH$_2$)$_5$— | | H |
| —(CH$_2$)$_6$— | | H |
| —(CH$_2$)$_7$— | | H |
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |
| —CH$_2$—CHCH$_3$—(CH$_2$)$_3$— | | H |
| —(CH$_2$)$_2$—CHCH$_3$—(CH$_2$)$_2$— | | H |
| —(CH$_2$)$_2$—CHC$_2$H$_5$—(CH$_2$)$_2$— | | H |
| —(CH$_2$)$_2$—CHC$_3$H$_7$—(CH$_2$)$_2$— | | H |
| —(CH$_2$)$_2$—CHi-C$_3$H$_7$—(CH$_2$)$_2$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHi-C$_3$H$_7$—(CH$_2$)$_2$— | | H |
| —(CH$_2$)$_2$—C(CH$_3$)$_2$—(CH$_2$)$_2$— | | H |
| —CH$_2$—(CHCH$_3$)$_2$—(CH$_2$)$_2$— | | H |
| —CH$_2$—CH—(CH$_2$)$_2$—CH— bridged by —CH$_2$— | | H |
| —CH$_2$—CH—CH—CH$_2$— bridged by —(CH$_2$)$_4$— | | H |
| —CH$_2$—CH—CH—(CH$_2$)$_2$— bridged by —(CH$_2$)$_3$— | | H |
| indane-bridge | | H |
| tetralin-bridge | | H |
| —(CH$_2$)$_3$— | | H |
| —(CH$_2$)$_4$— | | H |
| —CH$_2$—CHCH$_3$—CH$_2$— | | H |
| —CH$_2$—CH$_2$—CHCH$_3$— | | H |
| —CH$_2$—CHCH$_3$—CH$_2$— | | H |
| —CH$_2$—S—CH$_2$— | | H |
| —CH$_2$—S—(CH$_2$)$_2$— | | H |
| —CH$_2$—CH—CH— bridged by —(CH$_2$)$_3$— | | H |
| H | CH$_3$ | H |
| H | C$_2$H$_5$ | H |
| H | C$_3$H$_7$ | H |
| H | i-C$_3$H$_7$ | H |
| H | cyclopropyl | H |
| H | cyclopentylmethyl | H |
| H | cyclohexyl | H |
| CH$_3$ | CH$_3$ | H |
| CH$_3$ | C$_2$H$_5$ | H |
| CH$_3$ | C$_3$H$_7$ | H |
| CH$_3$ | i-C$_3$H$_7$ | H |
| CH$_3$ | cyclopropyl | H |
| CH$_3$ | cyclopentylmethyl | H |
| CH$_3$ | cyclohexylmethyl | H |
| C$_2$H$_5$ | CH$_3$ | H |
| C$_2$H$_5$ | C$_2$H$_5$ | H |

Table 2: A, B and D are each as given in Table 1
W=CH$_3$; X=CH$_3$; Y=CH=CH$_2$; Z=H.
Table 3: A, B and D are each as given in Table 1
W=CH$_3$; X=C$_2$H$_5$; Y=CH$_3$; Z=H.
Table 4: A, B and D are each as given in Table 1
W=CH$_3$; X=CH$_3$; Y=C$_2$H$_5$; Z=H.
Table 5: A, B and D are each as given in Table 1
W=C$_2$H$_5$; X=C$_2$H$_5$; Y=CH$_3$; Z=H.
Table 6: A, B and D are each as given in Table 1
W=C$_2$H$_5$; X=C$_2$H$_5$; Y=C$_2$H$_5$; Z=H.
Table 7: A, B and D are each as given in Table 1
W=CH$_3$; X=C≡CH; Y=CH$_3$; Z=H.
Table 8: A, B and D are each as given in Table 1
W=CH$_3$; X=CH=CH$_2$; Y=CH$_3$; Z=H.
Table 9: A, B and D are each as given in Table 1
W=CH$_3$; X=C$_2$H$_5$; Y=C$_2$H$_5$; Z=H.
Table 10: A, B and D are each as given in Table 1
W=H; X=CH$_3$; Y=C≡CH; Z=H.
Table 11: A, B and D are each as given in Table 1
W=H; X=CH$_3$; Y=CH=CH; Z=H.
Table 12: A, B and D are each as given in Table 1
W=H; X=C$_2$H$_5$; Y=CH$_3$; Z=H.
Table 13: A, B and D are each as given in Table 1
W=H; X=CH$_3$; Y=C$_2$H$_5$; Z=H.
Table 14: A, B and D are each as given in Table 1
W=H; X=CH$_3$; Y=H; Z=C$_2$H$_5$.
Table 15: A, B and D are each as given in Table 1
W=H; X=CH$_3$; Y=CH$_3$; Z=C$_2$H$_5$.

Besides the compounds mentioned in the Preparation Examples, the following compounds of the formula (I-2-a) may be specifically mentioned:

TABLE 16

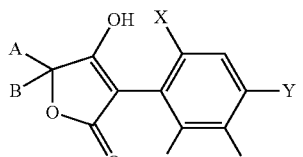

W = CH$_3$, X = CH$_3$, Y = C≡CH, Z = H

| A | B |
|---|---|
| CH$_3$ | H |
| C$_2$H$_5$ | H |
| C$_3$H$_7$ | H |
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
| C$_2$H$_5$ | C$_2$H$_5$ |
| C$_3$H$_7$ | C$_3$H$_7$ |
|  | CH$_3$ |
| 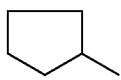 | CH$_3$ |
| 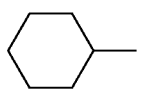 | CH$_3$ |
| —(CH$_2$)$_2$— | |
| —(CH$_2$)$_4$— | |
| —(CH$_2$)$_5$— | |
| —(CH$_2$)$_6$— | |
| —(CH$_2$)$_7$— | |
| —(CH$_2$)$_2$—O—(CH$_2$)$_2$— | |
| —CH$_2$—O—(CH$_2$)$_3$— | |
| —(CH$_2$)$_2$—S—(CH$_2$)$_2$— | |
| —CH$_2$—CHCH$_3$—(CH$_2$)$_3$— | |
| —(CH$_2$)$_2$—CHCH$_3$—(CH$_2$)$_2$— | |
| (CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi—C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHi—C$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |

—CH$_2$—CH—(CH$_2$)$_2$—CH—
        └—CH$_2$—┘

—CH$_2$—CH————CH—CH$_2$—
      └—(CH$_2$)$_4$—┘

—CH$_2$—CH————CH—(CH$_2$)$_2$—
      └—(CH$_2$)$_3$—┘

TABLE 16-continued

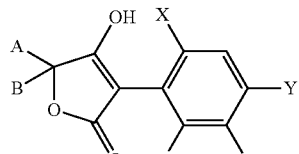

W = CH$_3$, X = CH$_3$, Y = C≡CH, Z = H

| A | B |
|---|---|
| 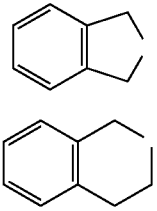 | |
| 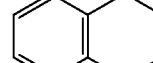 | |

Table 17: A and B are each as given in Table 16
W=CH$_3$; X=CH$_3$; Y=CH=CH$_1$; Z=H.

Table 18: A and B are each as given in Table 16
W=CH$_3$; X=CH$_5$; Y=CH$_3$; Z=H.

Table 19: A and B are each as given in Table 16
W=CH$_3$; X=CH$_3$; Y=C$_2$H$_5$; Z=H.

Table 20: A and B are each as given in Table 16
W=C$_2$H$_5$; X=C$_2$H$_5$; Y=CH$_3$; Z=H.

Table 21: A and B are each as given in Table 16
W=C$_7$H$_5$; X=C$_2$H$_5$; Y=C$_2$H$_5$; Z=H.

Table 22: A and B are each as given in Table 16
W=CH$_3$; X=C≡CH; Y=CH$_3$; Z=H.

Table 23: A and B are each as given in Table 16
W=CH$_3$; X=CH=CH$_2$; Y=CH$_3$; Z=H.

Table 24: A and B are each as given in Table 16
W=CH$_3$; X=C$_2$H$_5$; Y=C$_2$H$_5$; Z=H.

Table 25: A and B are each as given in Table 16
W=H; X=CH$_3$; Y=C≡CH; Z=H.

Table 26: A and B are each as given in Table 16
W=H; X=CH$_3$; Y=CH=CH$_2$; Z=H.

Table 27: A and B are each as given in Table 16
W=H; X=C$_2$H$_5$; Y=CH$_3$; Z=H.

Table 28: A and B are each as given in Table 16
W=H; X=CH$_3$; Y=C$_2$H$_5$; Z=H.

Table 29: A and B are each as given in Table 16
W=H; X=CH$_3$; Y=H; Z=C$_2$H$_5$.

Table 30: A and B are each as given in Table 16
W=H; X=CH$_3$; Y=CH$_3$; Z=C$_2$H$_5$.

Using, in accordance with process (A), ethyl N-(2-methyl-4-ethinyl-phenylacetyl)-1-aminocyclohexane-carboxylate as starting material, the course of the process according to the invention can be represented by the following equation:

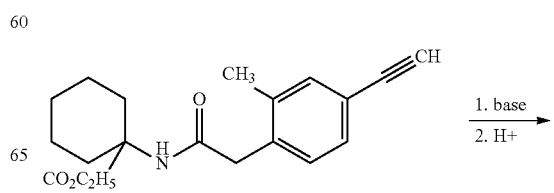

1. base
2. H+

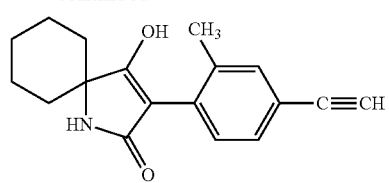

Using, in accordance with process (B), ethyl O-(2,4,6-triethyl-phenylacetyl)-2-hydroxyisobutyrate, the course of the process according to the invention can be represented by the following equation:

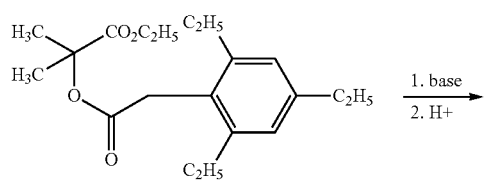

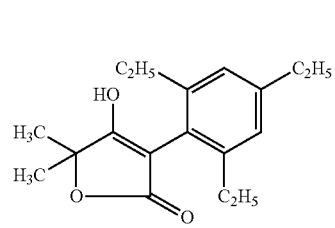

Using, in accordance with process (C), ethyl 2-(2,6-dimethyl-4-ethyl-phenyl)-4-(4-methoxy)-benzylmercapto-4-methyl-3-oxo-valerate, the course of the process according to the invention can be represented by the following equation:

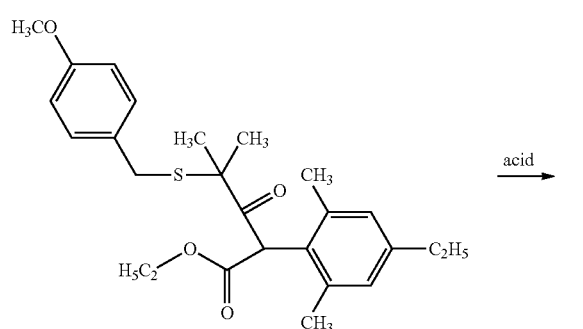

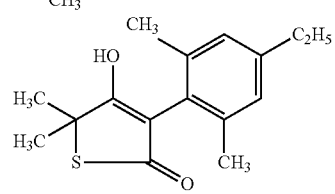

Using, for example in accordance with process (D), (chlorocarbonyl) 2-(2-ethyl-4,6-dimethyl)-phenylketene and acetone as starting materials, the course of the process according to the invention can be represented by the following equation:

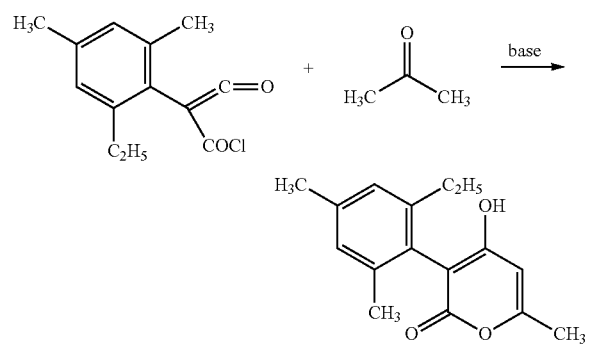

Using, for example in accordance with process (E), (chlorocarbonyl) 2-(2,6-dimethyl-4-ethyl)-phenyl ketene and thiobenzamide as starting materials, the course of the process according to the invention can be represented by the following equation:

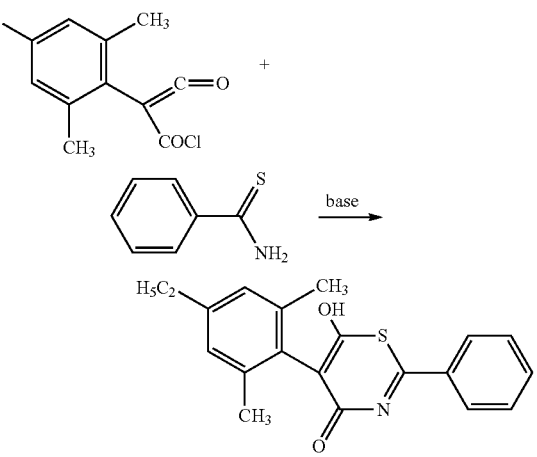

Using, in accordance with process (F), ethyl 5-(2,4-diethyl-6-methyl-phenyl)-2,3-tetramethylene-4-oxo-valerate, the course of the process according to the invention can be represented by the following equation:

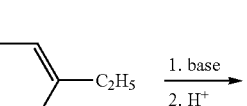

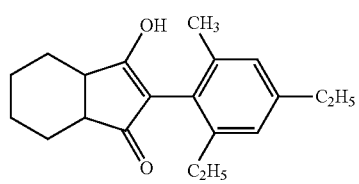

Using, in accordance with process (G), ethyl 5-[(2,4,6-triethyl-phenyl)-phenyl]-2,2-dimethyl-5-oxo-hexanoate, the course of the process according to the invention can be represented by the following equation:

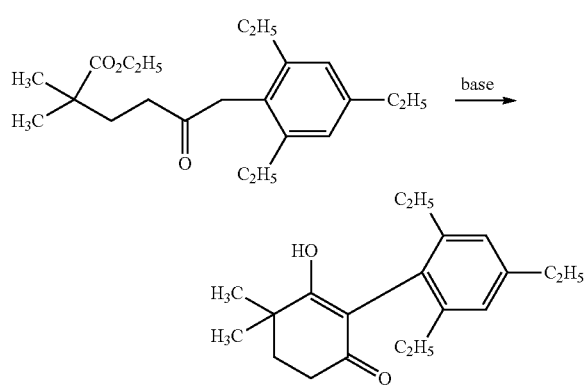

Using, in accordance with process (H), 3-[(2,6-dimethyl-4-bromo)-phenyl]-4,4-(pentamethylene)-pyrrolidine-2,4-dione as starting material, the course of the reaction can be represented by the following scheme:

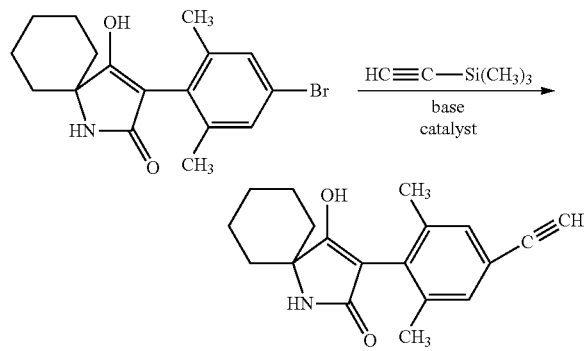

Using, in accordance with process (Iα), 3-(2,6-dimethyl-4-ethinyl-phenyl)-5,5-dimethylpyrrolidine-2,4-dione and pivaloyl chloride as starting materials, the course of the process according to the invention can be represented by the following equation:

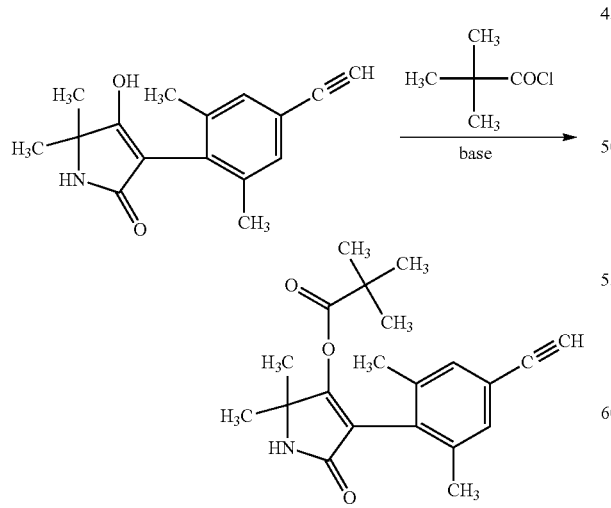

Using, in accordance with process (Iβ), 3-(2-ethyl-4,6-dimethyl-phenyl)-4-hydroxy-5-phenyl-Δ³-dihydrofuran-2-one and acetic anhydride as starting materials, the course of the process according to the invention can be represented by the following equation:

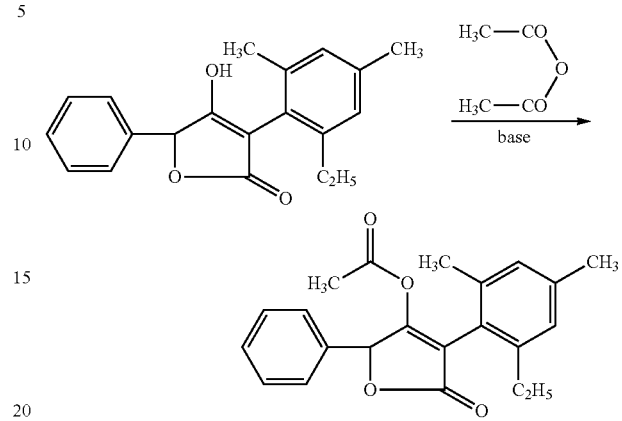

Using, in accordance with process (J), 8-[(2,6-diethyl-4-methyl)-phenyl]-1-aza-bicyclo-[4.3.0$^{1,6}$]-nonane-7,9-dione and ethoxyethyl chloroformate as starting materials, the course of the process according to the invention can be represented by the following equation:

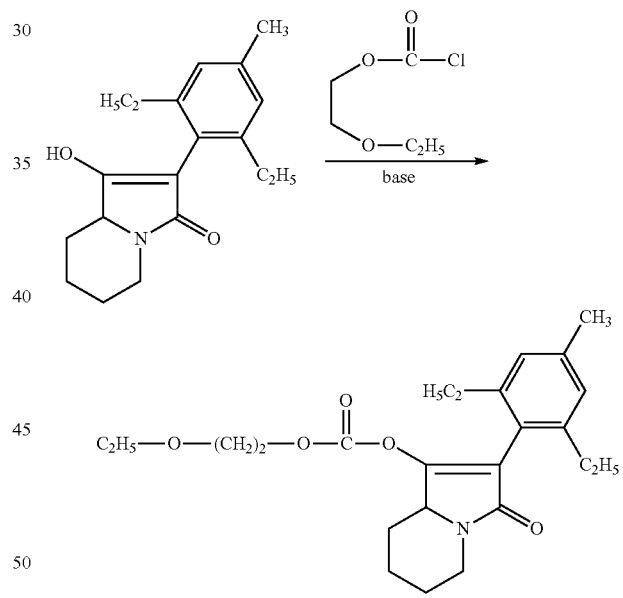

Using, in accordance with process (K), 3-(2-ethyl-4,6-dimethyl-phenyl)-4-hydroxy-5-methyl-6-(3-pyridyl)-pyrone and methyl chloromonothioformate as starting materials, the course of the reaction can be represented as follows:

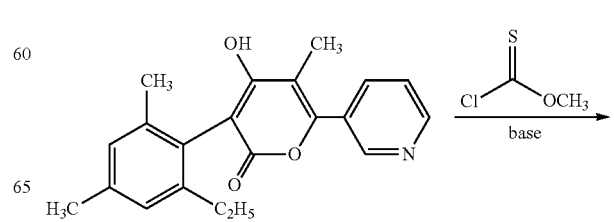

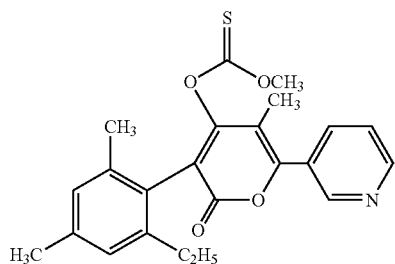

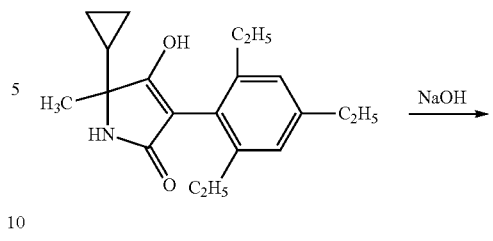

Using, in accordance with process (L), 3-(2,6-dimethyl-4-ethyl-phenyl)-5,5-penta-methylene-pyrrolidine-2,4-dione and methanesulfonyl chloride as starting materials, the course of the reaction can be represented by the following equation:

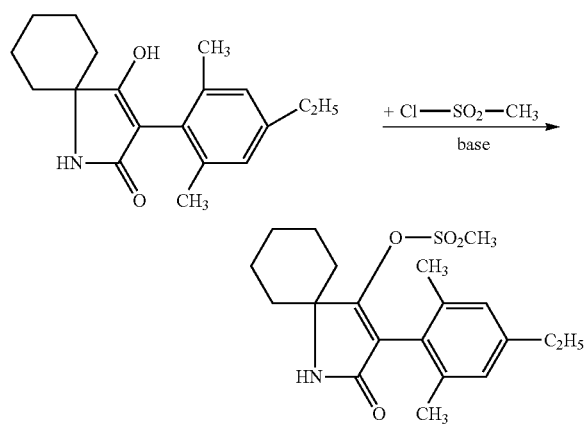

Using, in accordance with process (M), 3-(2,4-diethyl-6-methyl-phenyl)-4-hydroxy-5,5-dimethyl-$\Delta^3$-dihydrofuran-2-one and 2,2,2-trifluoroethyl methanethio-phosphonyl chloride as starting materials, the course of the reaction can be represented by the following equation:

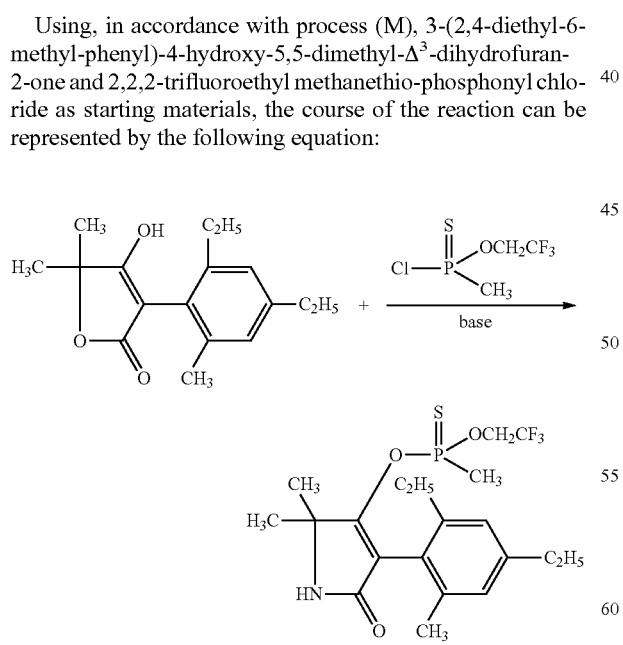

Using, in accordance with process (N), 3-(2,4,6-triethyl-phenyl)-5-cyclopropyl-5-methyl-pyrrolidine-2,4-dione and NaOH as components, the course of the process according to the invention can be represented by the following equation:

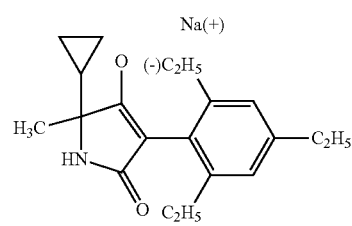

Using, in accordance with process (O), variant α, 3-(2,4-diethyl-6-methyl-phenyl)-4-hydroxy-5-tetramethylene-$\Delta^3$-dihydro-furan-2-one and ethyl isocyanate as starting materials, the course of the reaction can be represented by the following equation:

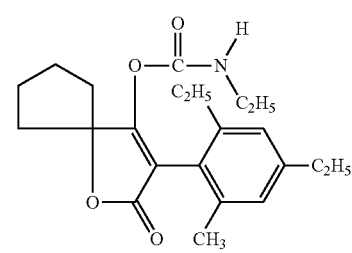

Using, in accordance with process (O), variant B, 3-(4-ethinyl-2,6-dimethyl-phenyl)-5-methyl-pyrrolidine-2,4-dione and dimethylcarbamoyl chloride as starting materials, the course of the reaction can be represented by the following scheme:

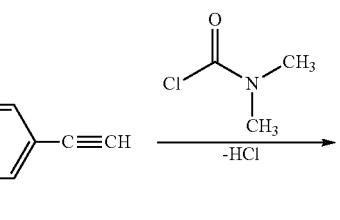

-continued

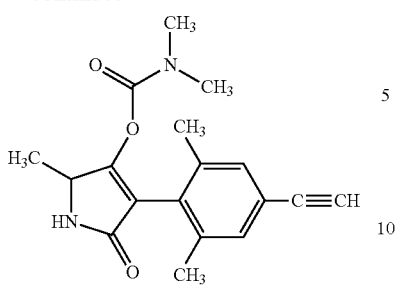

The compounds of the formula (II)

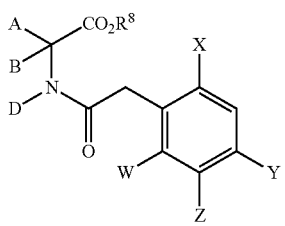

(II)

in which

A, B, D, W, X, Y, Z and $R^8$ are each as defined above which are required as starting materials in the process (a) according to the invention are novel.

The acylamino acid esters of the formula (II) are obtained, for example, when amino acid derivatives of the formula (XXI)

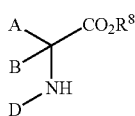

(XXI)

in which

A, B, $R^8$ and D are each as defined above are acylated with substituted phenylacetyl halides of the formula (XXII)

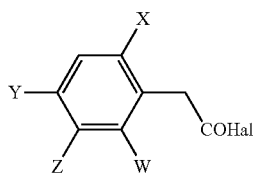

(XXII)

in which

W, X, Y and Z are each as defined above and

Hal represents chlorine or bromine (Chem. Reviews 52, 237-416 (1953); Bhattacharya, Indian J. Chem. 6, 341-5, 1968)

or when acylamino acids of the formula (XXIII)

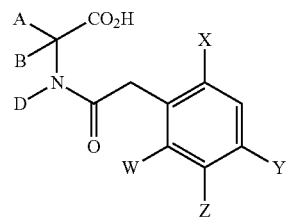

(XXIII)

in which

A, B, D, W, X, Y and Z are each as defined above are esterified (Chem. Ind. (London) 1568 (1968)).

The compounds of the formula (XXIII)

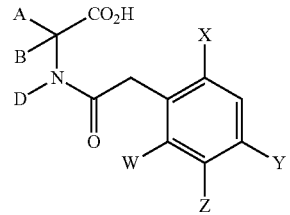

(XXIII)

in which

A, B, D, W, X, Y and Z are each as defined above are novel.

Compounds of the formula (XXIII) are obtained when amino acids of the formula (XXIV)

(XXIV)

in which

A, B and D are each as defined above are acylated with substituted phenyl acetyl halides of the formula (XXII)

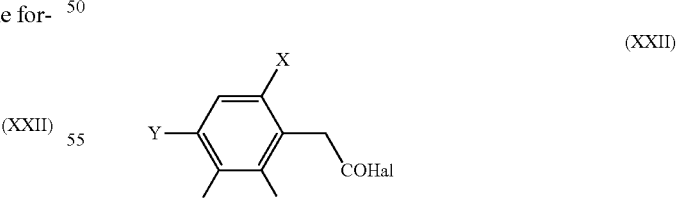

(XXII)

in which

W, X, Y and Z are each as defined above and

Hal represents chlorine or bromine, for example according to Schotten-Baumann (Organikum, VEB Deutscher Verlag der Wissenschaften, Berlin 1977, p. 505).

The compounds of the formula (XXII) are novel. They can be prepared by processes which are known in principle (see, for example, H. Henecka, Houben-Weyl, Methoden der Organischen Chemie, Vol. 8, pp. 467-469 (1952)).

The compounds of the formula (XXII) are obtained, for example, by reacting substituted phenylacetic acids of the formula (XXV)

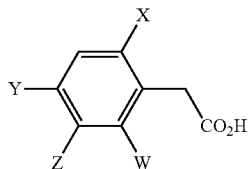
(XXV)

in which
W, X, Y and Z are each as defined above
with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons such as toluene or methylene chloride), at temperatures from −20° C. to 150° C., preferably from −10° C. to 100° C.

Some of the compounds of the formulae (XXI) and (XXIV) are known, and/or they can be prepared by known processes (see, for example, Compagnon, Miocque Ann. Chim. (Paris) [14] 5, S. 11-22, 23-27 (1970)).

The substituted cyclic aminocarboxylic acids of the formula (XXIV) in which A and B form a ring are generally obtainable by the Bucherer-Bergs synthesis or by the Strecker synthesis and are in each case obtained in different isomer forms. Thus, under the conditions of the Bucherer-Bergs synthesis, the isomers (for simplicity called β below), in which the radicals R and the carboxyl group are equatorial are predominantly obtained, while under the conditions of the Strecker synthesis the isomers (for simplicity called (o below) in which the amino group and the radicals R are equatorial are predominantly obtained.

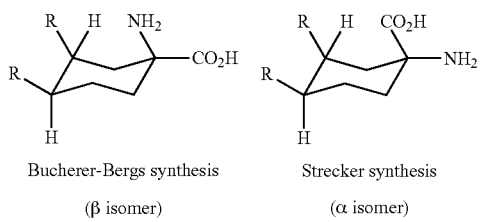

Bucherer-Bergs synthesis (β isomer)      Strecker synthesis (α isomer)

(L. Munday, J. Chem. Soc. 4372 (1961); J. T. Eward, C. Jitrangeri, Can. J. Chem. 53, 3339 (1975).

Furthermore, the starting materials of the formula (II)

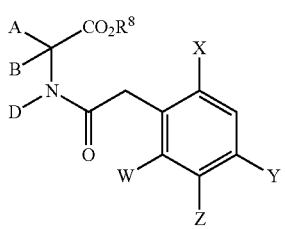
(II)

in which
A, B, D, W, X, Y, Z and $R^8$ are each as defined above
used in the above process (A) can be prepared when aminonitriles of the formula (XXVI)

(XXVI)

in which
A, B and D are each as defined above
are reacted with substituted phenylacetyl halides of the formula (XXII)

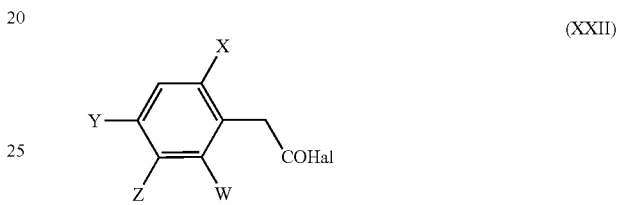
(XXII)

in which
W, X, Y, Z and Hal are each as defined above
to give compounds of the formula (XXVII)

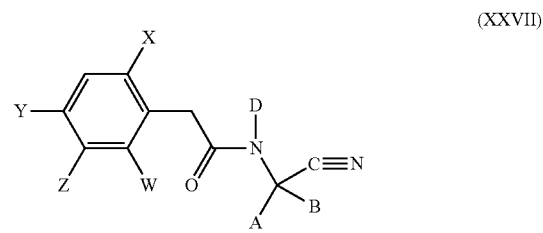
(XXVII)

in which
A, B, D, W, X, Y and Z are each as defined above
and these are subsequently subjected to acidic alcoholysis.

The compounds of the formula (XXVII) are likewise novel.

The compounds of the formula (III)

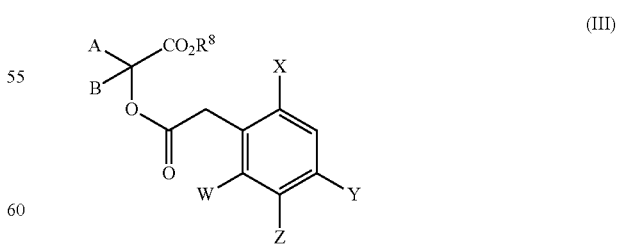
(III)

in which
A, B, W, X, Y, Z and $R^8$ are each as defined above
required as starting materials in the process (B) according to the invention are novel.

They can be prepared by methods known in principle.

Thus, the compounds of the formula (III), for example, are obtained when 2-hydroxycarboxylic esters of the formula (XXVIII)

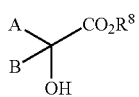
(XXVIII)

in which

A, B and $R^8$ are each as defined above are acylated with substituted phenylacetyl halides of the formula (XXII)

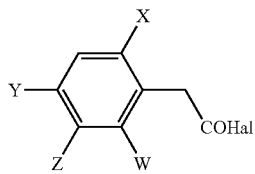
(XXII)

in which

W, X, Y, Z and Hal are each as defined above (Chem. Reviews 52, 237-416 (1953)).

Furthermore, compounds of the formula (I) are obtained when substituted phenylacetic acids of the formula (XXV)

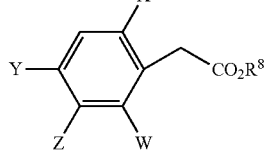
(XXV)

in which

W, X, Y and Z are each as defined above are alkylated with α-halogenocarboxylic esters of the formula (XXIX)

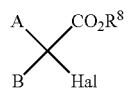
(XXIX)

in which

A, B and $R^8$ are each as defined above and

Hal represents chlorine or bromine.

The compounds of the formula (XXV) are novel.

The compounds of the formula (XXIX) are commercially available.

The compounds of the formula (XXV)

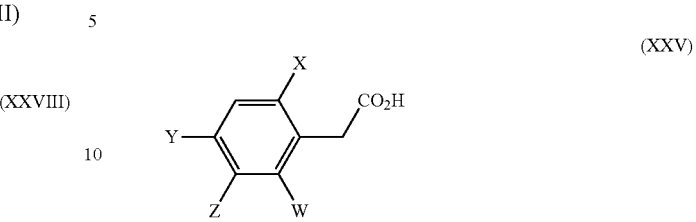
(XXV)

in which

W, X, Y and Z are each as defined above and

Y may furthermore represent —C≡C—Si(CH$_3$)$_3$ are obtained, for example, when phenylacetic esters of the formula (XXX)

(XXX)

in which

W, X, Y, Z and $R^8$ are each as defined above are hydrolysed in the presence of acids or bases, in the presence of a solvent, under generally known standard conditions.

The compounds of the formula (XXX) are novel.

The compounds of the formula (XXX)

(XXX)

in which

W, X, Y, Z and $R^8$ are each as defined above, and

Y may furthermore represent —C≡C—Si(CH$_3$)$_3$ are obtained, for example, when phenylacetic esters of the formula (XXX-a)

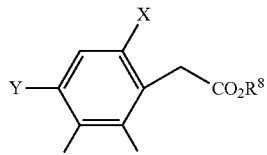
(XXX-a)

in which $R^8$, W, X, Y and Z are each as defined above, and one or two of the radicals, in particular one radical, W, X, Y or Z represents chlorine, bromine or iodine, in particular bromine, with the proviso that the other radicals W, X, Y or Z do not represent alkenyl or alkinyl, are reacted with silylacetylenes of the formula (X-a) or vinyl-stannanes of the formula (X-b)

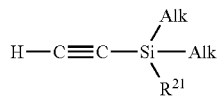
(X-a)

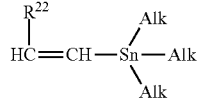
(X-b)

in which Alk preferably represents $C_1$-$C_4$-alkyl, $R^{21}$ preferably represents $C_1$-$C_4$-alkyl or phenyl and $R^{22}$ is as defined above in the presence of a solvent, if appropriate in the presence of a base and a catalyst (preferably one of the palladium complexes mentioned above).

Some of the phenylacetic esters of the formula (XXX-a) are known from the applications WO 96/35 664, WO 97/02 243, WO 97/01535, WO 97/36868 or WO 98/05638, or they can be prepared by processes described therein.

Furthermore, phenylacetic esters of the formula (XXX) are obtained by the processes (P) and (Q) described further below.

The compounds of the formula (IV)

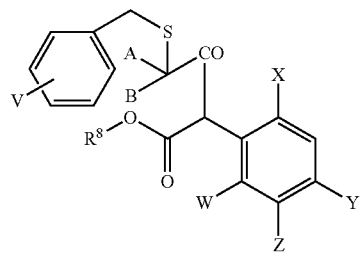
(IV)

in which

A, B, V, W, X, Y, Z and $R^8$ are each as defined above required as starting materials in the above process (C) are novel.

They can be prepared by methods known in principle.

The compounds of the formula (IV) are obtained, for example when substituted phenylacetic esters of the formula (XXX)

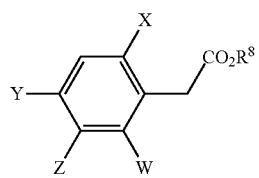
(XXX)

in which

W, X, Y, $R^8$ and Z are each as defined above are acylated with 2-benzylthio-carbonyl halides of the formula (XXX)

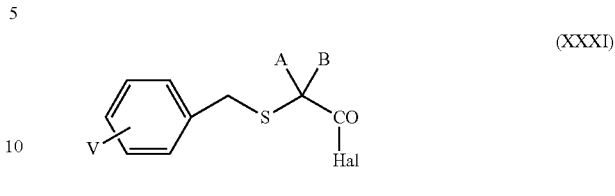
(XXXI)

in which

A, B and V are each as defined above and

Hal represents halogen (in particular chlorine or bromine) in the presence of strong bases (see, for example, M. S. Chambers, E. J. Thomas, D. J. Williams, J. Chem. Soc. Chem. Commun., (1987), 1228).

Some of the benzylthio-carbonyl halides of the formula (XXXI) are known, and/or they can be prepared by known processes (J. Antibiotics (1983), 26, 1589). The halogenocarbonyl ketenes of the formula (VI) required as starting materials in the above process (D) and (E) are novel. They can be prepared in a simple manner by methods which are known in principle (cf. for example, Org. Prep. Proced. Int., 7, (4), 155-158, 1975 and DE 1 945 703). Thus, for example, the compounds of the formula (VI)

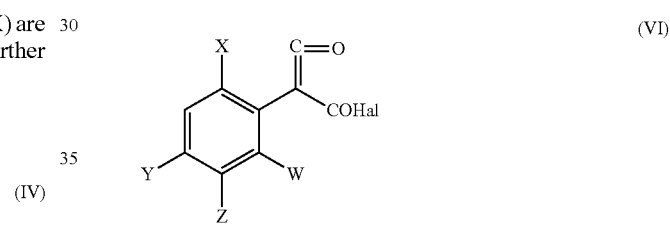
(VI)

in which

W, X, Y and Z are each as defined above and

Hal represents chlorine or bromine are obtained when substituted phenylmalonic acids of the formula (XXXII)

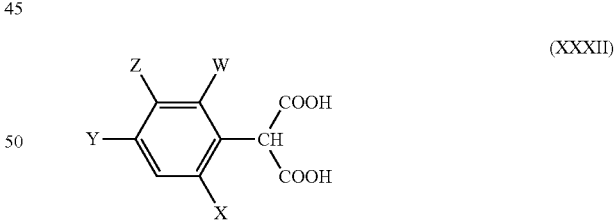
(XXXII)

in which

W, X, Y and Z are each as defined above are reacted with acid halides, such as, for example, thionyl chloride, phosphorus(V) chloride, phosphorus(III) chloride, oxalyl chloride, phosgene or thionyl bromide, if appropriate in the presence of catalysts, such as, for example, diethylformamide, methyl-sterylformamide or triphenylphosphine and, if appropriate, in the presence of bases, such as, for example, pyridine or triethylamine.

The substituted phenylmalonic acids of the formula (XXXII) are novel. They can be prepared in a simple manner by known processes (cf., for example, Organikum, VEB Deutscher Verlag der Wissenschaften, Berlin 1977, p. 517 ff, EP-A-528 156, WO 96/35 664, WO 97/02 243, WO 97/01535, WO 97/36868 and WO 98/05638).

Thus, phenylmalonic acids of the formula (XXXII)

(XXXII)

in which

W, X, Y and Z are each as defined above are obtained when phenylmalonic esters of the formula (XXXIII)

(XXXIII)

in which

W, X, Y, Z and $R^8$ are each as defined above are initially hydrolysed in the presence of a base and a solvent and subsequently carefully acidified (EP-528 156, WO 96/35 664, WO 97/02 243).

Some of the malonic esters of the formula (XXXIII)

(XXXIII)

in which

W, X, Y, Z and $R^8$ are each as defined above are known.

They can be prepared by generally known methods of organic chemistry (cf., for example, Tetrahedron Lett. 27, 2763 (1986), Organikum, VEB Deutscher Verlag der Wissenschaften, Berlin 1977, p. 587 ff., WO 96/35664, WO 97/02243, WO 97/01535, WO 97/36868, WO 98/05638 and WO 99/47525).

The carbonyl compounds of the formula (V)

(V)

in which

A and D are each as defined above required as starting materials for the process (D) according to the invention or their silyl enol ethers of the formula (Va)

(Va)

in which

A, D and $R^8$ are each as defined above are commercially available, generally known compounds or compounds which are obtainable by known processes.

The preparation of the ketene acid chlorides of the formula (VI) required as starting materials for carrying out the process (E) according to the invention has already been described above. The thioamides of the formula (VII)

(VII)

in which

A is as defined above required for carrying out the process (E) according to the invention are compounds which are generally known in organic chemistry.

The compounds of the formula (VI)

(VIII)

in which

A, B, $Q^1$, $Q^2$, W, X, Y, Z and $R^8$ are each as defined above required as starting materials in the above process (F) are novel.

They can be prepared by methods known in principle.

The 5-aryl-4-ketocarboxylic esters of the formula (VIII) are obtained, for example, when 5-aryl-4-ketocarboxylic acids of the formula (XXXIV)

(XXXIV)

in which

W, X, Y, Z, A, B, $Q^1$ and $Q^2$ are each as defined above are esterified (cf., for example, Organikum, $15^{th}$ edition, Berlin, 1977, page 499) or alkylated (see Preparation Example).

The 5-aryl-4-ketocarboxylic acids of the formula (XXXIV)

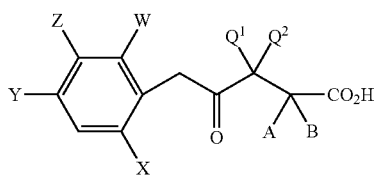

(XXXIV)

in which

A, B, $Q^1$, $Q^2$, W, X, Y and Z are each as defined above are novel but can be prepared by methods known in principle (see Preparation Example).

The 5-aryl-4-ketocarboxylic acids of the (XXXIV) are obtained, for example, when 2-phenyl-3-oxo-adipic esters of the formula (XXXV)

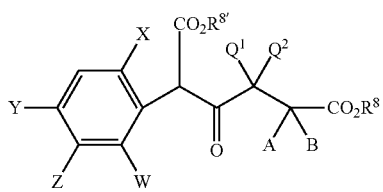

(XXXV)

in which

A, B, $D^1$, $D^2$, W, X, Y and Z are each as defined above and $R^8$ and $R^{8'}$ each represent alkyl (in particular $C_1$-$C_8$-alkyl) and in which, if the compound of the formula (XXXVII) is used, $R^8$ represents hydrogen are decarboxylated, if appropriate in the presence of a diluent and if appropriate in the presence of a base or an acid (cf., for example, Organikum, $15^{th}$ edition, Berlin, 1977, pages 519 to 521).

The compounds of the formula (XXXV)

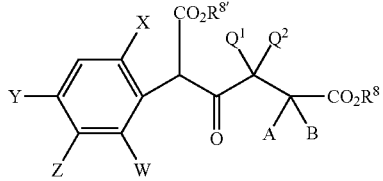

(XXXV)

in which

A, B, $Q^1$, $Q^2$, W, X, Y, Z, $R^8$, $R^{8'}$ are each as defined above and in which, if the compound of the formula (XXXVII) is used, $R^8$ represents hydrogen are novel.

The compounds of the formula (XXXV) are obtained, for example, when dicarboxylic monoester chlorides of the formula (XXXVI),

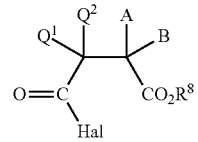

(XXXVI)

in which

A, B, $Q^1$, $Q^2$ and $R^8$ are each as defined above and

Hal represents chlorine or bromine or carboxylic anhydrides of the formula (XXXVII)

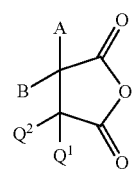

(XXXVII)

in which

A, B, $Q^1$ and $Q^2$ are each as defined above are acylated with a phenylacetic ester of the formula (XXX)

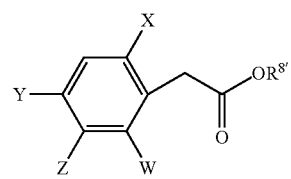

(XXX)

in which

W, X, Y, Z and $R^{8'}$ are each as defined above in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

Some of the compounds of the formulae (XXXVI) and (XXXVII) are known compounds of organic chemistry, and/or they can be prepared in a simple manner by methods known in principle.

The compounds of the formula (IX)

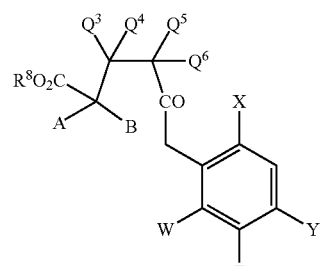

(IX)

in which

A, B, Q³, Q⁴, Q⁵, Q⁶, W, X, Y, Z and R⁸ are each as defined above required as starting materials in the above process (G) are novel.

They can be prepared by methods known in principle.

The 6-aryl-5-ketocarboxylic esters of the formula (IX) are obtained, for example, when 6-aryl-5-ketocarboxylic acids of the formula (XXXVIII)

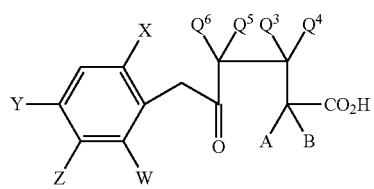

(XXXVIII)

in which

A, B, Q³, Q⁴, Q⁵, Q⁶, W, X, Y and Z are each as defined above are esterified (cf., for example, Organikum, 15$^{th}$ edition, Berlin, 1977, page 499).

The 6-aryl-5-ketocarboxylic acids of the formula (XXXVIII)

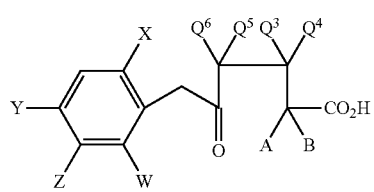

(XXXVIII)

in which

A, B, Q³, Q⁴, Q⁵, Q⁶, W, X, Y and Z are each as defined above are novel. They can be prepared by methods known in principle, for example by hydrolysing and decarboxylating substituted 2-phenyl-3-oxo-heptanedioic esters of the formula (XXXIX)

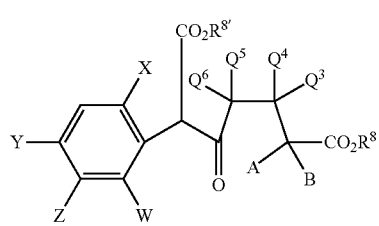

(XXXIX)

in which

A, B, Q³, Q⁴, Q⁵, Q⁶, W, X, Y and Z are each as defined above and

R⁸ and R⁸' are each alkyl (preferably $C_1$-$C_6$-alkyl), if appropriate in the presence of a diluent and if appropriate in the presence of a base or acid (cf., for example, Organikum, 15$^{th}$ edition, Berlin, 1977, pages 519 to 521).

The compounds of the formula (XXXIX)

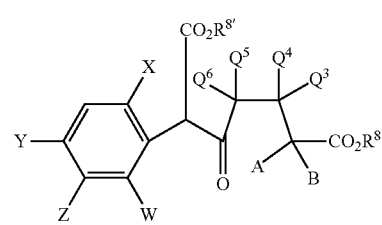

(XXXIX)

in which

A, B, Q³, Q⁴, Q⁵, Q⁶, W, X, Y, Z, R⁸ and R⁸' are each as defined above are novel and can be obtained when dicarboxylic anhydrides of the formula (XLI)

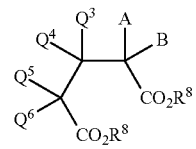

(XLI)

in which

A, B, Q³, Q⁴, Q⁵, Q⁶ and R⁸ are each as defined above are condensed with a substituted phenylacetic ester of the formula (XXX)

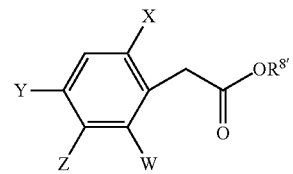

(XXX)

in which

W, X, Y, Z and R⁸' are each as defined above in the presence of a diluent and in the presence of a base.

Some of the compounds of the formula (XLI) are known, and/or they can be prepared by known processes.

The compounds of the formula (XXX) have already been described under the precursors for the process (B) or are described explicitly as examples in processes (P) and (Q) below.

(P) Thus, furthermore, compounds of the formula (XXX),

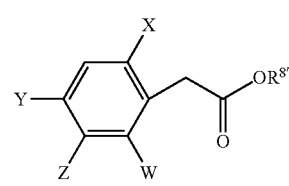

(XXX)

in which

W, X, Y, Z and $R^{8'}$ are each as defined above are obtained when acylphenylacetic esters of the formula (XLII)

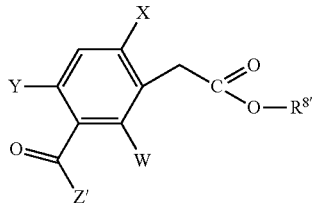
(XLII)

W, X, Y and $R^8$ are each as defined above and

Z' represents alkyl are reduced with suitable reducing agents (such as, for example, Zn/HCl, hydrogen/catalyst, hydrazine/base), if appropriate in the presence of a solvent.

The compounds of the formula (XLII) are novel.

Compounds of the formula (XLII)

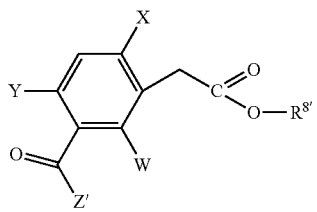
(XLII)

in which

W, X, Y, Z' and $R^{8'}$ are each as defined above are obtained when phenylacetic esters of the formula (XXX-b)

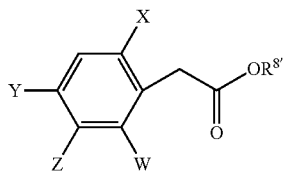
(XXX-b)

in which

W, X, Y and $R^{8'}$ are each as defined above and

Z represents hydrogen are Friedel-Crafts acylated, if appropriate in the presence of a solvent, using a carbonyl chloride or carboxylic anhydride in the presence of an acid or a Lewis acid (for example aluminium chloride, iron(III) bromide).

The compounds (XXX-b) are known or can be prepared by the processes described in the literature cited at the outset.

(Q) Phenylacetic esters of the formula (XXX),

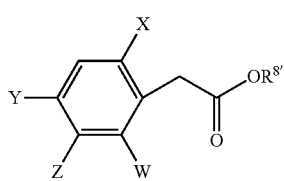
(XXX)

in which

X represents alkyl,

W, Y and Z each represent hydrogen or alkyl and $R^{8'}$ represents alkyl are furthermore obtained when phenylacetic esters of the formula (XXX-c),

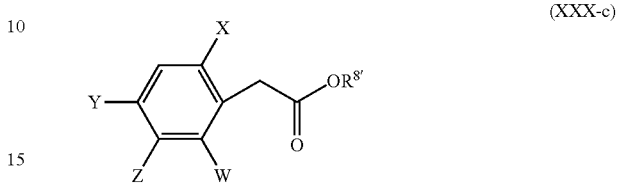
(XXX-c)

in which

X represents alkyl, $R^{8'}$ represents alkyl and

W, Y and Z may represent, in addition to hydrogen and alkyl, chlorine and bromine are dehalogenated in the presence of a solvent and in the presence of a reducing agent (for example hydrogen in the presence of a noble-metal catalyst such as, for example, palladium or platinum).

The compounds of the formula (XXX-c) are known from the patent applications cited at the outset or can be prepared by the processes described therein.

Some of the compounds of the formulae (I-1'a) to (I-8'-a) in which A, B, D, $Q^1$, $Q^2$, $Q^3$, $Q^4$, $Q^5$, $Q^6$, W', X', Y' and Z' are each as defined above, required as starting materials in the above process (H), are known (WO 96/35 664, WO 97/02 243, WO 97/01535, WO 97/36868, WO 98/05638) or they can be prepared by the processes described therein.

Some of the coupling agents of the formulae (X-a) and (X-b)

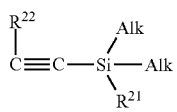
(X-a)

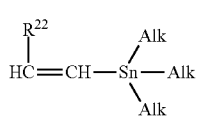
(X-b)

in which

Alk, $R^{21}$ and $R^{22}$ are each as defined above are commercially available, or they can be prepared in a simple manner by generally known processes.

The acid halides of the formula (XI), carboxylic anhydrides of the formula (XII), chloroformic esters or chloroformic thioesters of the formula (XIII), chloromonothioformic esters or chlorodithioformic esters of the formula (XIV), sulphonyl chlorides of the formula (XV), phosphorus compounds of the formula (XVI) and metal hydroxides, metal alkoxides or amines of the formulae (XVII) and (XVII) and isocyanates of the formula (XIX) and carbamoyl chlorides of the formula (XX) furthermore required as starting materials for carrying out the processes (I), (J), (K), (L), (M), (N) and (O) according to the invention are generally known compounds of organic or inorganic chemistry.

Moreover, the compounds of the formulae (V), (VII), (XI) to (XX), (XXI), (XXIV), (XXVI), (XXVIII), (XXIX), (XXXI), (XXXVI), (XXXVII) and (XLI) are known from the patent applications cited at the outset, and/or they can be prepared by the methods given therein.

The process (A) is characterized in that compounds of the formula (II) in which A, B, D, W, X, Y, Z and $R^8$ are each as defined above are subjected to an intramolecular condensation in the presence of a base.

Suitable diluents for the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, iso-propanol, butanol, iso-butanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (A) according to the invention, the reaction temperatures can be varied within a relatively wide range. In general, the reaction is carried out at temperatures between 0° C. and 250° C., preferably between 50° C. and 150° C.

The process (A) according to the invention is generally carried out under atmospheric pressure.

When carrying out process (A) according to the invention, the reaction components of the formula (II) and the deprotonating bases are generally employed in approximately double-equimolar amounts. However, it is also possible to use a larger excess (up to 3 mol) of one component or the other.

The process (B) is characterized in that compounds of the formula (III) in which A, B, W, X, Y, Z and $R^8$ are each as defined above are subjected to an intramolecular condensation in the presence of a diluent and in the presence of a base.

Suitable diluents for the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, iso-propanol, butanol, iso-butanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (B) according to the invention, the reaction temperatures can be varied within a relatively wide range. In general, the reaction is carried out at temperatures between 0° C. and 250° C., preferably between 50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process (C) is characterized in that compounds of the formula (IV) in which A, B, V, W, X, Y, Z and $R^8$ are each as defined above are cyclized intramolecularly in the presence of an acid and, if appropriate, in the presence of a diluent.

Suitable diluents for the process (C) according to the invention are all inert organic solvents. Preference is given to using hydrocarbons, such as toluene and xylene, furthermore halogenated hydrocarbons such as dichloromethane, chloroform, ethylene chloride, chlorobenzene, dichlorobenzene, moreover polar solvents, such as dimethyl sulphoxide, sulpholane, dimethyl formamide and N-methyl-pyrrolidone. Furthermore, it is possible to employ alcohols such as methanol, ethanol, propanol, iso-propanol, butanol, isobutanol and tert-butanol.

If appropriate, the acid used can also serve as diluent.

Suitable acids for the process (C) according to the invention are all customary inorganic and organic acids, such as, for example, hydrohalic acids, sulphuric acid, alkyl-, aryl- and haloalkylsulphonic acids, in particular halogenated alkylcarboxylic acids, such as, for example, trifluoroacetic acid.

When carrying out the process (C) according to the invention, the reaction temperatures can be varied within a relatively wide range. In general, the reaction is carried out at temperatures between 0° C. and 250° C., preferably between 50° C. and 150° C.

The process (C) according to the invention is generally carried out under atmospheric pressure.

When carrying out the process (C) according to the invention, the reaction components of the formulae (IV) and the acid are employed, for example, in equimolar amounts. However, it is also possible, if appropriate, to use the acid as solvent or as catalyst.

The process (D) according to the invention is characterized in that carbonyl compounds of the formula (V) or enol ethers thereof of the formula (V-a) are reacted with ketene acid halides of the formula (VI) in the presence of a diluent and, if appropriate, in the presence of an acid acceptor.

Suitable diluents for the process (D) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide or N-methyl-pyrrolidone.

Suitable acid acceptors for carrying out the process variant D) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethyl-aniline.

When carrying out the process variant D) according to the invention, the reaction temperatures can be varied within a relatively wide range. Advantageously, the reaction is carried out at temperatures between 0° C. and 250° C., preferably between 50° C. and 220° C.

The process (D) according to the invention is advantageously carried out under atmospheric pressure.

When carrying out the process (D) according to the invention, the reaction components of the formulae (V) and (VI) in which A, D, W, X, Y and Z are each as defined above and Hal represents halogen, and, if appropriate, the acid acceptors, are generally employed in approximately equimolar amounts. However, it is also possible to use a relatively large excess (up to 5 mol) of one component or the other.

The process (E) according to the invention is characterized in that thioamides of the formula (VII) are reacted with ketene acid halides of the formula (VI) in the presence of a diluent and, if appropriate, in the presence of an acid acceptor.

Suitable diluents for the process variant E) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methyl-pyrrolidone.

Suitable acid acceptors for carrying out the process (E) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethyl-aniline.

When carrying out the process (E) according to the invention, the reaction temperatures can be varied within a relatively wide range. Advantageously, the reaction is carried out at temperatures between 0° C. and 250° C., preferably between 20° C. and 220° C.

The process (E) according to the invention is advantageously carried out under atmospheric pressure.

When carrying out the process (E) according to the invention, the reaction components of the formulae (VII) and (VI) in which A, W, X, Y and Z are each as defined above and Hal represents halogen, and, if appropriate, the acid acceptors, are generally employed in approximately equimolar amounts. However, it is also possible to use a relatively large excess (up to 5 mol) of one component or the other.

The process (F) is characterized in that compounds of the formula (VIII) in which A, B, $Q^1$, $Q^2$, W, X, Y, Z and $R^8$ are each as defined above are subjected to an intramolecular condensation in the presence of a base.

Suitable diluents for the process (F) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. It is furthermore possible to use alcohols, such as methanol, ethanol, propanol, iso-propanol, butanol, isobutanol, tert-butanol.

Suitable bases (deprotonating agents) for carrying out the process (F) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (methyltrialkyl($C_8$-$C_{10}$)ammonium chloride) or TDA 1 (tris-(methoxyethoxyethyl)-amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (F) according to the invention, the reaction temperatures can be varied within a relatively wide range. In general, the reaction is carried out at temperatures between −75° C. and 250° C., preferably between −50° C. and 150° C. The process (F) according to the invention is generally carried out under atmospheric pressure.

When carrying out the process (F) according to the invention, the reaction components of the formula (VIII) and the deprotonating bases are generally employed in approximately equimolar amounts. However, it is also possible to use a relatively large excess (up to 3 mol) of one component or the other.

The process (G) is characterized in that compounds of the formula (IX) in which A, B, $Q^3$, $Q^4$, $Q^5$, $Q^6$, W, X, Y, Z and $R^8$ are each as defined above are subjected to an intramolecular condensation in the presence of bases.

Suitable diluents for the process (G) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. Alcohols, such as methanol, ethanol, propanol, iso-propanol, butanol, isobutanol and tert-butanol can also be used.

Suitable bases (deprotonating agents) for carrying out the process (H) according to the invention are all customary proton acceptors.

Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (methyltrialkyl($C_9$-$C_{10}$)ammonium chloride) or TDA 1 (tris-(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying the process (G) according to the invention, the reaction temperatures can be varied within a relatively wide range. In general, the reaction is carried out at temperatures between 0° C. and 250° C., preferably between 50° C. and 150° C.

The process (G) according to the invention is generally carried out under atmospheric pressure.

When carrying out the process (G) according to the invention, the reaction components of the formula (IX) and the deprotonating bases are generally employed in approximately equimolar amounts. However, it is also possible to use a relatively large excess (up to 3 mol) of one component or the other.

For carrying out the process (H) according to the invention, palladium(0) complexes are suitable as catalysts. Preference is given to, for example, tetrakis-(triphenylphosphine)palladium or bis-(triphenylphosphine)-palladium dichloride/triphenyl phosphine.

Suitable acid acceptors for carrying out the process (H) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, caesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (H) according to the invention are water, organic solvents and any mixtures thereof. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monomethyl ether; water.

The reaction temperature in the process (H) according to the invention can be varied within a relatively wide range. In general, the reaction is carried out at temperatures between 0° C. and +140° C., preferably between 50° C. and +100° C.

When carrying out the process (H) according to the invention, the coupling agents of the formula (X-aI) or (X-b) and compounds of the formulae (I-1'-a) to (I-8'-a) are employed in a molar ratio of from 1:1 to 5:1. preferably from 1:1 to 2:1. In general, 0.005 to 0.5 mol, preferably 0.01 mol to 0.1 mol of catalyst is employed per mole of the compounds of the formulae (I-1'-a) to (I-8'-a). The base is usually employed in excess.

The process (I-α) is characterized in that compounds of the formulae (I-1-a) to (I-7-a) are in each case reacted with carbonyl halides of the formula (XI), if appropriate in the presence of a diluent and if appropriate in the presence of an acid binder.

Suitable diluents for the process (I-α) according to the invention are all solvents which are inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acid halide permitting, the reaction can also be carried out in the presence of water.

Suitable acid binders for the reaction according to the process (I-α) according to the invention are all customary acid acceptors. Preference is given to using tertiary amines, such as triethylamine, pyridine, diazabicyclooctane (DABCO), diazabicyclo-undecene (DBU), diazabicyclononene (DBN), Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides such as sodium hydroxide and potassium hydroxide.

The reaction temperatures in the process (I-α) according to the invention can be varied within a relatively wide range. In general, the reaction is carried out at temperatures between −20° C. and +150° C., preferably between 0° C. and 100° C.

When carrying out the process (I-α) according to the invention, the starting materials of the formulae (I-1-a) to (I-7-a) and the carbonyl halide of the formula (XI) are generally in each case employed in approximately equivalent amounts. However, it is also possible to employ a relatively large excess (up to 5 mol) of the carbonyl halide. Work-up is carried out by customary methods.

The process (I-β) is characterized in that compounds of the formulae (I-1-a) to (I-7-a) are reacted with carboxylic anhydrides of the formula (XII), if appropriate in the presence of a diluent and if appropriate in the presence of an acid binder.

Preferred diluents for the process (I-β) according to the invention are those diluents which are also preferred when acid halides are used. Otherwise, it is also possible for a carboxylic anhydride employed in excess to act simultaneously as a diluent.

In the process (I-β), acid binders which are added, if appropriate, are preferably those acid binders which are also preferred when acid halides are used.

In the process (I-β) according to the invention, the reaction temperatures can be varied within a relatively wide range. In general, the reaction is carried out at temperatures between −20° C. and +150° C., preferably between 0° C. and 100° C.

When carrying out the process (I-β) according to the invention, the starting materials of the formulae (I-1-a) to (I-7-a) and the carboxylic anhydride of the formula (XII) are generally each employed in approximately equivalent amounts. However, it is also possible to use a relatively large excess (up to 5 mol) of the carboxylic anhydride. Work-up is carried out by customary methods.

In general, the adopted procedure is to remove diluent and excess carboxylic anhydride and also the carboxylic acid formed by distillation or by washing with an organic solvent or with water.

The process (J) is characterized in that compounds of the formulae (I-1-a) to (I-7-a) are in each case reacted with chloroformic esters or chloroformic thiol esters of the formula (XV), if appropriate in the presence of a diluent and if appropriate in the presence of an acid binder.

Suitable diluents for the reaction according to the process (J) according to the invention are all customary acid acceptors. Preference is given to using tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides such as sodium hydroxide and potassium hydroxide.

Suitable diluents for the process (J) according to the invention are all solvents which are inert towards the chloroformic esters or chloroformic thiol esters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (J) according to the invention the reaction temperatures can be varied within a relatively wide range. If the reaction is carried out in the presence of a diluent and an acid binder, the reaction temperatures are generally between –20° C. and +100° C., preferably between 0° C. and 50° C.

The process (J) according to the invention is generally carried out under atmospheric pressure.

When carrying out the process (J) according to the invention, the starting materials of the formulae (I-1-a) to (I-7-a) and the appropriate chloroformic ester or chloroformic thiol ester of the formula (XIII) are generally in each case employed in approximately equivalent amounts. However, it is also possible to employ a relatively large excess (up to 2 mol) of one component or the other. Work-up is carried out by customary methods. In general, precipitated salts are removed and the reaction mixture that remains is concentrated by stripping the diluent.

The process (K) according to the invention is characterized in that compounds of the formulae (I-1-a) to (I-7-a) are in each case reacted with compounds of the formula (XIV) in the presence of a diluent and, if appropriate, in the presence of an acid binder.

In the preparation process (K), approximately 1 mol of chloromonothioformic ester or chlorodithioformic ester of the formula (XIV) is reacted per mole of starting material of the formulae (I-1-a) to (I-7-a), at from 0 to 120° C., preferably from 20 to 60° C.

Suitable diluents which are added if appropriate are all inert polar organic solvents, such as ethers, amides, sulphones, sulphoxides, but also halogenoalkanes.

Preference is given to using dimethyl sulphoxide, tetrahydrofuran, dimethyl-formamide or methylene chloride.

If, in a preferred embodiment, the enolate salt of the compounds (I-1-a) to (I-7-a) is prepared by addition of strong deprotonating agents, such as, for example, sodium hydride or potassium tert-butoxide, it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (L) according to the invention is characterized in that compounds of the formulae (I-1-a) to (I-7-a) are in each case reacted with sulphonyl chlorides of the formula (XV), if appropriate in the presence of a diluent and if appropriate in the presence of an acid binder.

In the preparation process (L), approximately 1 mol of sulphonyl chloride of the formula (XV) is reacted per mole of starting material of the formula (I-1-a to I-7-a), at from –20 to 150° C., preferably at from 20 to 70° C.

Suitable diluents which are added if appropriate are all inert polar organic solvents, such as ethers, amides, nitriles, sulphones, sulphoxides or halogenated hydrocarbons, such as methylene chloride.

Preference is given to using dimethyl sulphoxide, tetrahydrofuran, dimethyl-formamide and methylene chloride.

If, in a preferred embodiment, the enolate salt of the compounds (I-1-a) to (I-7-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (M) according to the invention is characterized in that compounds of the formulae (I-1-a) to (I-7-a) are in each case reacted with phosphorus compounds of the formula (XVI), if appropriate in the presence of a diluent and if appropriate in the presence of an acid binder.

In the preparation process (M), 1 to 2, preferably 1 to 1.3, mol of the phosphorus compound of the formula (XVI) are reacted per mole of the compounds (I-1-a) to (I-7-a) at temperatures between –40° C. and 150° C., preferably between –10 and 110° C., to give compounds of the formulae (I-1-e) to (I-7-e).

Suitable solvents which are added if appropriate are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added if appropriate are customary inorganic or organic bases such as hydroxides, carbonates or amines. Examples include sodium hydroxide, sodium carbonate, potassium carbonate, pyridine, triethylamine.

The reaction can be carried out at atmospheric pressure or under elevated pressure and is preferably carried out under atmospheric pressure. Work-up is carried out by customary methods of organic chemistry. The resulting end products are preferably purified by crystallization, chromatographic purification or by so-called "incipient distillation", i.e. removal of the volatile components under reduced pressure.

The process (N) is characterized in that compounds of the formulae (I-1-a) to (I-7-a) are reacted with metal hydroxides or metal alkoxides of the formula (XVII) or amines of the formula (XVIII), if appropriate in the presence of a diluent.

Preferred diluents for the process (N) according to the invention are ethers, such as tetrahydrofuran, dioxane, diethyl ether, or else alcohols, such as methanol, ethanol, isopropanol, but also water.

The process (N) according to the invention is generally carried out under atmospheric pressure.

The reaction temperatures are generally between −20° C. and 100° C., preferably between 0° C. and 50° C.

The process (O) according to the invention is characterized in that compounds of the formulae (I-1-a) to (I-7-a) are in each case reacted with (O-α) compounds of the formula (XIX), if appropriate in the presence of a diluent and if appropriate in the presence of a catalyst, or (O-β) with compounds of the formula (XX), if appropriate in the presence of a diluent and if appropriate in the presence of an acid binder.

In the preparation process (O-α), approximately 1 mol of isocyanate of the formula (XIX) is reacted per mole of starting material of the formulae (I-1-a) to (I-7-a), at from 0 to 100° C., preferably at from 20 to 50° C.

Suitable diluents which are added if appropriate are all inert organic solvents, such as ethers, amides, nitriles, sulphones and sulphoxides.

If appropriate, catalysts may be added to accelerate the reaction. Very advantageously, the catalysts which are employed are organotin compounds, such as, for example, dibutyltin dilaurate. The reaction is preferably carried out at atmospheric pressure.

In the preparation process (O-β), approximately 1 mol of carbamoyl chloride of the formula (XX) is reacted per mole of starting material of the formulae (I-1-a) to (I-7-a), at from −20 to 150° C., preferably at from 0 to 70° C.

Suitable diluents which are added if appropriate are all inert polar organic solvents, such as ethers, amides, sulphones, sulphoxides or halogenated hydrocarbons.

Preference is given to using dimethyl sulphoxide, tetrahydrofuran, dimethyl-formamide or methylene chloride.

If, in a preferred embodiment, the enolate salt of the compounds (I-1-a) to (I-7-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds having good plant tolerance and favourable warm-blood toxicity are suitable for controlling animal pests, in particular insects, arachnids and nematodes, which are encountered in agriculture, in forestry, in the protection of stored products and of materials, and in the hygiene sector. They are preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella occidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp.,

*Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematoden include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

At certain concentrations or application rates, the compounds according to the invention may, if appropriate, also be used as herbicides and microbicides, for example as fungicides, antimycotics and bactericides. If appropriate, they may also be used as intermediates or precursors for the synthesis of further active compounds.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:
for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:
Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimancin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole,
tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-3-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide, isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl[(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate, methyl N-(chloroacetyl)-N-(2,6-dimethylphenyl)-DL-alaninate,
N-(2,3-dichloro-4-hydroxyphenyl)-1-methyl-cyclohexanecarboxamide.
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulfonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin, *Bacillus*

*popilliae*, *Bacillus sphaericus*, *Bacillus subtilis*, *Bacillus thuringiensis*, Baculoviridae, *Beauveria bassiana*, *Beauveria tenella*, bendiocarb, benfuracarb, bensultap, benzoximate, betacyfluthrin, bifenazate, bifenthrin, bioethanomethrin, bio-permethrin, BPMC, bromophos A, bufencarb, buprofezin, butathiofos, butocarboxim, butylpyridaben, cadusafos, carbaryl, carbofuran, carbophenothion, carbosuifan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *metharhizium anisopliae, metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron. tefluthrin, temephos, temivinphos, terbufos, tetrachlorvinphos, thetacypermethnn, thiamethoxam, thiapronil, thiatriphos, thiocyclam hydrogen oxalate, thiodicarb, thiofanox, thuringiensin, tralocythrin, tralomethrin, triarathene, triazamate, triazophos, triazurone, trichlophenidine, trichiorfon, triflumuron, trimethacrb, vamidothion, vaniliprole, *Verticillium lecanii*,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropalecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamnate.

4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4,5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoramidothioate.

A mixture with other known active compounds, such as herbicides, or with fertilizers and growth regulators is also possible.

The active compounds according to the invention can furthermore be present when used as insecticides in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis*, *Periplaneta americana*, *Blattela germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as being preferred—but without any limitation:
Beetles, such as

*Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus* and *Sinoxylon* spec. *Dinoderus minutus*.

Hymenopterons, such as

*Sirex juvencus*, *Urocerus gigas*, *Urocerus gigas taignus* and *Urocerus augur*

Termites, such as

*Kalotermes flavicollis*, *Cryptotermes brevis*, *Heterotcrmes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*.

Bristletails, such as *Lepisma saccarina*.

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and wood processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamcthrin, permcethrin, imidacloprid, NI-25, flufenoxuron, hexaflumuron, transfluthrin, thiacloprid, methoxyphenoxide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis-(trialkyltin) sulphides, tri-n-butyltin laurate, tri-n-butyltin chloride, copper (I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylenebisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3, 5-triazine, dichlorophen, diuron, endothal, fentine acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluor-folpet, 3-iodo-2-propinyl butylcarbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulphone, 2-(N,N-di-methylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetra-methylthiuram disulphide and 2,4,6-trichlorophenylmaleiimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Onlscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domcstica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can be used as defoliants, desiccants, haulm killers and, especially, as weed killers. Weeds in the broadest sense are understood to mean all plants which grow in locations where they are undesired.

Whether the substances according to the invention act as total or selective herbicides depends essentially on the amount used.

The active compounds according to the invention can be used, for example, in connection with the following plants:

Dicotyledonous Weeds of the Genera:

*Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous Crops of the Genera:

*Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous Weeds of the Genera:

*Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous Crops of the Genera:

*Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds according to the invention have strong herbicidal activity and a broad activity spectrum when used on the soil or on above-ground parts of plants. To a certain extent, they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant varieties protectable or not protectable by plant breeders' rights. Plant parts are to be understood to mean all above-ground and underground parts and organs of plants, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seed, also by applying one or more coats.

As already mentioned above, it is possible to treat all plants and their parts according to the invention. In a preferred embodiment, wild plant species and plant varieties, or those obtained by conventional biological breeding, such as crossing or protoplast fusion, and parts thereof, are treated. In a further preferred embodiment, transgenic plants and plant varieties obtained by genetical engineering, if appropriate in combination with conventional methods (Genetic Modified Organisms), and parts thereof are treated. The term "parts" or "parts of plants" or "plant parts" has been explained above.

Particularly preferably, plants of the plant varieties which are in each case commercially available or in use are treated according to the invention.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant varieties (i.e. those obtained by genetical engineering) which are preferred according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant varieties having these or still to be developed genetic traits, which plants will be developed and/or marketed in the future.

The plants listed can be treated according to the invention in a particularly advantageous manner with the active compound mixtures according to the invention. The preferred ranges stated above for the active compounds also apply to the treatment of these plants. Particular emphasis is given to the treatment of plants with the mixtures specifically mentioned in the present text.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth; and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example
acetochlor, acifluorfen (-sodium), aclonifen, alachlor, alloxydim (-sodium), ametryne, amicarbazone, amidochlor, amidosulfuron, anilofos, asulam, atrazine, aza-fenidin, azimsulfuron, BAS-662H, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromo-fenoxim, bromoxynil, butachlor, butafenacil (-allyl), butroxydim, butylate, cafen-strole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxy-sulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flu-carbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), gly-phosate (-isopropylammonium), halosafen, haloxyfop (-ethoxyethyl, —P-methyl), hex-azinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyri-fop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orben-carb, oryzalin, oxadiargyl, oxadiazon, oxasulfuron, oxaziclomefone, oxyfluorfen, paraquat, pelargonsaiure, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-p-ethyl, -p-tefuryl), rimsulfuron, sethoxydim, simazine, simetryn, sulcotnone, sulfentrazone, sulfometuron (-methyl), sulfosate, sulfosulfuron, tebutam, tebuthiuron, tepraloxydim, terbuthylazine, terbutryn, thenylchlor, thiaflu-amide, thiazopyr, thidiazimin, thifensulfuron (-methyl), thiobencarb, tiocarbazil, tralkoxydim, triallate, triasulfuron, tribenuron (-methyl), triclopyr, tridiphane, tri-fluralin, trifloxysulfuron, triflusulfuron (-methyl), tritosulfuron.

A mixture with other known active compounds, such as fungicides, insecticides, acaricides, nematicides, bird repellents, plant nutrients and agents which improve soil structure, is also possible.

The active compounds can be used as such, in the form of the formulations or in the use forms prepared therefrom by further dilution, such as ready-to-use solutions, suspensions, emulsions, powders, pastes and granules. They are used in a customary manner, for example by watering, spraying, atomizing, or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and use of the active compounds according to the invention is illustrated by the examples below.

PREPARATION EXAMPLES

Example I-1-a-1

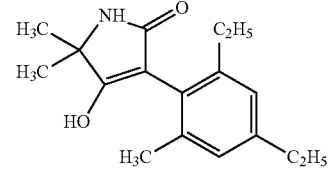

At 60° C., 7.4 g of the compound of Example II-1, dissolved in 1 ml of anhydrous dimethylformamide (DMF), are added dropwise to 6.5 g of potassium tert-butoxide in 25 ml of anhydrous DMF, and stirring is continued and the reaction is monitored by thin-layer chromatography. After the reaction has ended, 170 ml of ice-water are added, the mixture is, at from 0° C. to 10° C., acidified with conc. hydrochloric acid to pH 2 and filtered off with suction, and the filter cake is washed with ice-water. The residue is purified chromatographically on silica gel using the mobile phase methylene chloride/methanol 9:1.

Yield: 3.90 g (≙ 58.00% of theory), m.p. 199° C.

The following compounds of the formula (I-a-1) were obtained similarly to Example (I-1-a-1) and in accordance with the general preparation instructions (I-a-1)

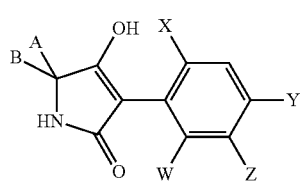

| Ex. No. | W | X | Y | Z | A | B | m.p. ° C. | Isomer |
|---|---|---|---|---|---|---|---|---|
| I-1-a-2 | CH₃ | C₂H₅ | C₂H₅ | H | —(CH₂)₂—CHCH₃—(CH₂)₂— | | 154 | β |
| I-1-a-3 | CH₃ | C₂H₅ | C₂H₅ | H | —(CH₂)₂—CHOCH₃—(CH₂)₂— | | 225 | β |
| I-1-a-4 | C₂H₅ | C₂H₅ | C₂H₅ | H | CH₃ | CH₃ | 200 | — |
| I-1-a-5 | C₂H₅ | C₂H₅ | C₂H₅ | H | —(CH₂)₂—CHCH₃—(CH₂)₂— | | 115 | β |
| I-1-a-6 | C₂H₅ | C₂H₅ | C₂H₅ | H | —(CH₂)₂—CHOCH₃—(CH₂)₂— | | 222 | β |
| I-1-a-7 | i-C₃H₇ | i-C₃H₇ | i-C₃H₇ | H | —(CH₂)₂—CHOCH₃—(CH₂)₂— | | >230 | β |
| I-1-a-8 | CH₃ | C₂H₅ | CH₃ | H | CH₃ | CH₃ | >220 | — |
| I-1-a-9 | CH₃ | C₂H₅ | CH₃ | H | —(CH₂)₂—CHCH₃—(CH₂)₂— | | 114 | β |
| I-1-a-10 | C₂H₅ | C₂H₅ | H | H | —(CH₂)₂—CHCH₃—(CH₂)₂— | | >220 | β |
| I-1-a-11 | C₂H₅ | C₂H₅ | H | H | —(CH₂)₂—O—(CH₂)₂— | | >220 | — |
| I-1-a-12 | CH₃ | C₂H₅ | H | H | CH₃ | CH₃ | 109 | — |
| I-1-a-13 | CH₃ | C₂H₅ | H | H | —(CH₂)₂—CHCH₃—(CH₂)₂— | | 216 | β |
| I-1-a-14 | H | CH₃ | H | i-C₄H₉ | CH₃ | CH₃ | 160 | — |
| I-1-a-15 | H | CH₃ | H | C₃H₇ | —(CH₂)₂—CHOCH₃—(CH₂)₂— | | 197 | β |
| I-1-a-16 | H | CH₃ | H | C₃H₇ | —(CH₂)₂—CHOC₂H₅—(CH₂)₂— | | 193 | β |
| I-1-a-17 | H | CH₃ | H | i-C₄H₉ | —(CH₂)₂—CHOCH₃—(CH₂)₂— | | 233 | β |
| I-1-a-18 | H | CH₃ | H | i-C₄H₉ | —(CH₂)₂—CHOC₂H₅—(CH₂)₂— | | 184 | β |
| I-1-a-19 | H | CH₃ | CH₃ | C₂H₅ | —(CH₂)₂—CHOCH₃—(CH₂)₂— | | 156 | β |
| I-1-a-20 | H | CH₃ | CH₃ | C₂H₅ | —(CH₂)₂—CHOC₂H₅—(CH₂)₂— | | 168 | β |
| I-1-a-21 | CH₃ | CH₃ | —C≡CH | H | —(CH₂)₂—CHOCH₃—(CH₂)₂— | | 127 | β |
| I-1-a-22 | H | CH₃ | C₂H₅ | H | —(CH₂)₂—CHCH₃—(CH₂)₂— | | 211 | β |
| I-1-a-23 | H | C₂H₅ | CH₃ | H | —(CH₂)₂—CHCH₃—(CH₂)₂— | | 210 | β |
| I-1-a-24 | H | C₂H₅ | CH₃ | H | —(CH₂)₂—O—(CH₂)₂— | | >220 | — |
| I-1-a-25 | H | C₂H₅ | CH₃ | H | CH₃ | CH₃ | 192 | — |
| I-1-a-26 | H | CH₃ | H | C₂H₅ | —(CH₂)₂—CHOC₂H₅—(CH₂)₂— | | 181 | β |
| I-1-a-27 | H | CH₃ | H | C₂H₅ | —(CH₂)₂—CHOCH₃—(CH₂)₂— | | 222 | β |
| I-1-a-28 | CH₃ | CH₃ | CH=CH₂ | H | —(CH₂)₂—CHOCH₃—(CH₂)₂— | | 278 | β |
| I-1-a-29 | CH₃ | CH₃ | C₂H₅ | H | —(CH₂)₂—CHOCH₃—(CH₂)₂— | | 268 | β |
| I-1-a-30 | CH₃ | CH₃ | C₂H₅ | H | —(CH₂)₂—CHOCH₃—(CH₂)₂— | | 248 | α |

Example I-1-b-1

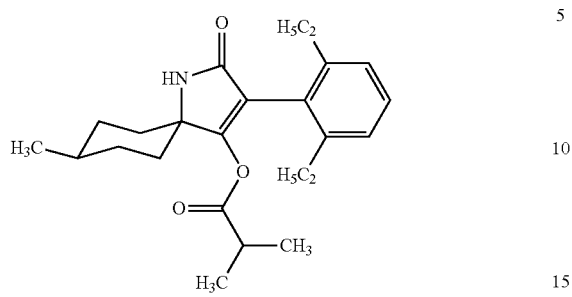

2.5 g of the compound I-1-a-10 in 50 ml of anhydrous ethyl acetate are heated at reflux with 1.7 ml of triethylamine, 1.3 ml of isobutyryl chloride in 5 ml of anhydrous ethyl acetate are added dropwise, the mixture is stirred at reflux and the reaction is monitored by thin-layer chromatography. The solvent is distilled off and the residue is taken up in methylene chloride, washed with 50 ml of 0.5 N NaOH, dried and concentrated using a rotary evaporator. The residue is then recrystallized from methyl tert-butyl ether (MTB ether)/n-hexane.

Yield: 2 g (≙ 65% of theory), m.p. 209° C.

The following compounds of the formula (I-1-b) are obtained similarly to Examples (I-1-b-1) and in accordance with the general preparation instructions

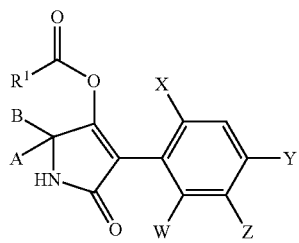

(I-1-b)

| Ex. No. | W | X | Y | Z | A | B | $R^1$ | m.p. ° C. | Isomer |
|---|---|---|---|---|---|---|---|---|---|
| I-1-b-2 | $CH_3$ | $C_2H_5$ | H | H | $CH_3$ | $CH_3$ | $i-C_3H_7$ | 145 | — |
| I-1-b-3 | $CH_3$ | $C_2H_5$ | H | H | —$(CH_2)_2$—$CHCH_3$—$(CH_2)_2$— | | $H_5C_2$—O—$CH_2$— | 135 | β |
| I-1-b-4 | $CH_3$ | $C_2H_5$ | H | H | $CH_3$ | $CH_3$ | $H_5C_2$—O—$CH_2$— | 76 | — |
| I-1-b-5 | H | $CH_3$ | $C_2H_5$ | H | —$(CH_2)_2$—$CHCH_3$—$(CH_2)_2$— | | $i-C_3H_7$ | 201 | β |
| I-1-b-6 | H | $CH_3$ | $C_2H_5$ | H | —$(CH_2)_2$—$CHCH_3$—$(CH_2)_2$— | | $i-C_4H_9$ | 215 | β |
| I-1-b-7 | H | $C_2H_5$ | $CH_3$ | H | —$(CH_2)_2$—O—$(CH_2)_2$— | | $i-C_3H_7$ | 190 | — |

Example I-1-c-1

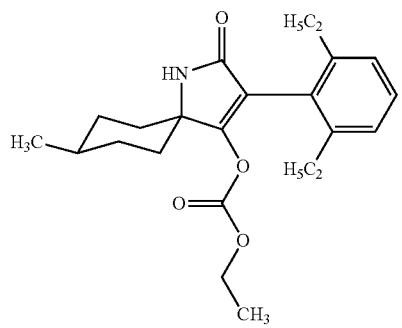

2.51 g of the compound of the formula I-1-a-10 and 1.2 ml of triethylamine are initially charged. At from 0 to 10° C., 0.8 ml of ethyl chloroformate in 5 ml of anhydrous dichloromethane are added dropwise, the mixture is stirred at room temperature and the reaction is monitored by thin-layer chromatography. The mixture is then washed with 0.5 N NaOH and dried, and the solvent is distilled off. The residue is recrystallized from methyl tert-butyl ether/n-hexane.

Yield: 1.1 g (≙ 30% of theory), m.p. 178° C.

The following compounds of the formula (I-1-c) are obtained similarly to Example (I-1-c-1) and in accordance with the general preparation instructions

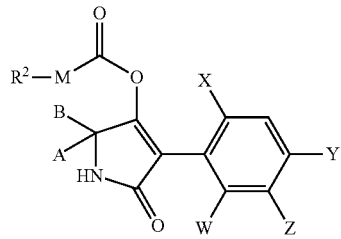

(I-1-c)

| Ex. No. | W | X | Y | Z | A | B | M | $R^2$ | m.p. °C. | Isomer |
|---|---|---|---|---|---|---|---|---|---|---|
| I-1-c-2 | $C_2H_5$ | $C_2H_5$ | H | H | —$(CH_2)_2$—O—$(CH_2)_2$— | | O | $C_2H_5$ | 194 | β |
| I-1-c-3 | $CH_3$ | $C_2H_5$ | H | H | $CH_3$ | $CH_3$ | O | $C_2H_5$ | 119 | — |
| I-1-c-4 | $CH_3$ | $CH_3$ | —C≡CH | H | —$(CH_2)_2$—CHOCH$_3$—$(CH_2)_2$— | | O | $C_2H_5$ | 171 | β |
| I-1-c-5 | H | $CH_3$ | $C_2H_5$ | H | —$(CH_2)_2$—CHCH$_3$—$(CH_2)_2$— | | O | i-$C_4H_9$ | 155 | β |
| I-1-c-6 | H | $C_2H_5$ | $CH_3$ | H | —$(CH_2)_2$—O—$(CH_2)_2$— | | O | $C_2H_5$ | 215 | — |
| I-1-c-7 | H | $CH_3$ | $CH_3$ | $C_2H_5$ | —$(CH_2)_2$—CHOCH$_3$—$(CH_2)_2$— | | O | $C_2H_5$ | 137 | β |
| I-1-c-8 | H | $CH_3$ | $CH_3$ | $C_2H_5$ | —$(CH_2)_2$—CHOC$_2H_5$—$(CH_2)_2$— | | O | $C_2H_5$ | 168 | β |

Example II-1

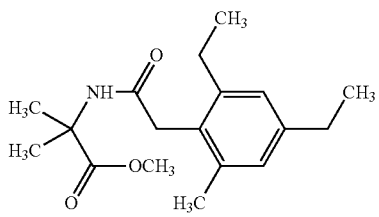

Example II-1

At 80° C., 7.5 g of 2,4-diethyl-6-methyl-phenylacetic acid and 9.2 ml of thionyl chloride are stirred until evolution of gas has ceased. Excess thionyl chloride is distilled off and the residue is taken up in 30 ml of dry THF. At from 0 to 10° C., this solution is added dropwise to 12.3 g of methyl 2-amino-2-methylpropanoate in 320 ml of dry THF admixed with 24.6 ml of triethylamine, and the mixture is stirred at room temperature for 1 h. This solution is then concentrated using a rotary evaporator, the residue is taken up in methylene chloride and 1 N HCl, the product is extracted and the organic phase is dried and concentrated using a rotary evaporator. The residue is recrystallized from MTB ether/n-hexane.

Yield: 8.07 g (≙ 66% of theory), m.p. 120-122° C.

Example II-11

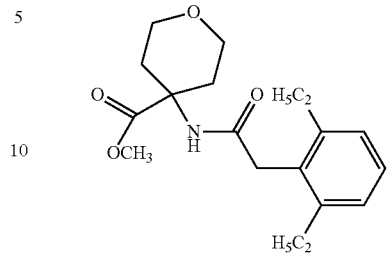

At an internal temperature of from 30 bis 40° C., 10.3 g of the compound of Example XXVII-1, as a suspension in 110 ml of methylene chloride, are added to 16.9 g of conc. sulphuric acid, and the mixture is stirred for 2 h. 23 ml of dry methanol are added dropwise, and the mixture is stirred at from 40 to 70° C. for 6 h. The solution is poured onto 0.18 kg of ice, the product is extracted with methylene chloride and the organic phase is washed with an $NaHCO_3$ solution. The organic phase is dried and concentrated using a rotary evaporator, and the residue is recrystallized from MTB ether/n-hexane.

Yield: 8.7 g (76% of theory), m.p. 137° C.

The following compounds of the formula (II) are obtained similarly to Example (II-1) and in accordance with the general preparation instructions

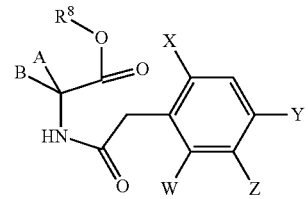

(II)

| Ex. No. | W | X | Y | Z | A | B | $R^8$ | m.p. °C. | Isomer |
|---|---|---|---|---|---|---|---|---|---|
| II-2 | $CH_3$ | $C_2H_5$ | $C_2H_5$ | H | —$(CH_2)_2$—$CHCH_3$—$(CH_2)_2$— | | $CH_3$ | 169 | β |
| II-3 | $CH_3$ | $C_2H_5$ | $C_2H_5$ | H | —$(CH_2)_2$—$CHOCH_3$—$(CH_2)_2$— | | $CH_3$ | 94 | β |
| II-4 | $C_2H_5$ | $C_2H_5$ | $C_2H_5$ | H | $CH_3$ | $CH_3$ | $CH_3$ | 109 | — |
| II-5 | $C_2H_5$ | $C_2H_5$ | $C_2H_5$ | H | —$(CH_2)_2$—$CHCH_3$—$(CH_2)_2$— | | $CH_3$ | 141 | β |
| II-6 | $C_2H_5$ | $C_2H_5$ | $C_2H_5$ | H | —$(CH_2)_2$—$CHOCH_3$—$(CH_2)_2$— | | $CH_3$ | 165 | β |
| II-7 | $i-C_3H_7$ | $i-C_3H_7$ | $i-C_3H_7$ | H | —$(CH_2)_2$—$CHOCH_3$—$(CH_2)_2$— | | $CH_3$ | 112 | β |
| II-8 | $CH_3$ | $C_2H_5$ | $CH_3$ | H | $CH_3$ | $CH_3$ | $CH_3$ | 126 | — |
| II-9 | $CH_3$ | $C_2H_5$ | $CH_3$ | H | —$(CH_2)_2$—$CHCH_3$—$(CH_2)_2$— | | $CH_3$ | 101 | β |
| II-10 | $C_2H_5$ | $C_2H_5$ | H | H | —$(CH_2)_2$—$CHCH_3$—$(CH_2)_2$— | | $CH_3$ | 108 | β |
| II-11 | $C_2H_5$ | $C_2H_5$ | H | H | —$(CH_2)_2$—O—$(CH_2)_2$— | | $CH_3$ | 137 | — |
| II-12 | $CH_3$ | $C_2H_5$ | H | H | $CH_3$ | $CH_3$ | $CH_3$ | 102 | — |
| II-13 | $CH_3$ | $C_2H_5$ | H | H | —$(CH_2)_2$—$CHCH_3$—$(CH_2)_2$— | | $CH_3$ | 169 | β |
| II-14 | H | $CH_3$ | H | $i-C_4H_9$ | $CH_3$ | $CH_3$ | $CH_3$ | 93 | — |
| II-15 | H | $CH_3$ | H | $C_3H_7$ | —$(CH_2)_2$—$CHOCH_3$—$(CH_2)_2$— | | $CH_3$ | 112 | β |
| II-16 | H | $CH_3$ | H | $C_3H_7$ | —$(CH_2)_2$—$CHOC_2H_5$—$(CH_2)_2$— | | $CH_3$ | 71 | β |
| II-17 | H | $CH_3$ | H | $i-C_4H_9$ | —$(CH_2)_2$—$CHOCH_3$—$(CH_2)_2$— | | $CH_3$ | 69 | β |
| II-18 | H | $CH_3$ | H | $i-C_4H_9$ | —$(CH_2)_2$—$CHOC_2H_5$—$(CH_2)_2$— | | $CH_3$ | 61 | β |
| II-19 | H | $CH_3$ | $CH_3$ | $C_2H_5$ | —$(CH_2)_2$—$CHOCH_3$—$(CH_2)_2$— | | $CH_3$ | 151 | β |
| II-20 | H | $CH_3$ | $CH_3$ | $C_2H_5$ | —$(CH_2)_2$—$CHOC_2H_5$—$(CH_2)_2$— | | $CH_3$ | 123 | β |
| II-21 | $CH_3$ | $CH_3$ | —C≡CH | H | —$(CH_2)_2$—$CHOCH_3$—$(CH_2)_2$— | | $CH_3$ | 141 | β |
| II-22 | H | $CH_3$ | $C_2H_5$ | H | —$(CH_2)_2$—$CHCH_3$—$(CH_2)_2$— | | $CH_3$ | 98 | β |
| II-23 | H | $C_2H_5$ | $CH_3$ | H | —$(CH_2)_2$—$CHCH_3$—$(CH_2)_2$— | | $CH_3$ | 149 | β |
| II-24 | H | $C_2H_5$ | $CH_3$ | H | —$(CH_2)_2$—O—$(CH_2)_2$— | | $CH_3$ | 164 | — |
| II-25 | H | $C_2H_5$ | $CH_3$ | H | $CH_3$ | $CH_3$ | $CH_3$ | 141 | — |
| II-26 | H | $CH_3$ | H | $C_2H_5$ | —$(CH_2)_2$—$CHOC_2H_5$—$(CH_2)_2$— | | $CH_3$ | 103 | β |
| II-27 | H | $CH_3$ | H | $C_2H_5$ | —$(CH_2)_2$—$CHOCH_3$—$(CH_2)_2$— | | $CH_3$ | Oil | β |

-continued

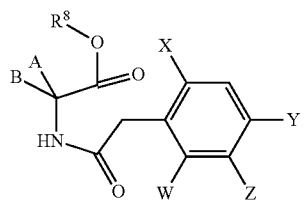
(II)

| Ex. No. | W | X | Y | Z | A | B | R$^8$ | m.p. °C. | Isomer |
|---|---|---|---|---|---|---|---|---|---|
| II-28 | CH$_3$ | CH$_3$ | CH=CH$_2$ | H | —(CH$_2$)$_2$—CHOCH$_3$—(CH$_2$)$_2$— | | CH$_3$ | 234 | β |
| II-29 | CH$_3$ | CH$_3$ | C$_2$H$_5$ | H | —(CH$_2$)$_2$—CHOCH$_3$—(CH$_2$)$_2$— | | CH$_3$ | 140 | β |

Example XXVII-1

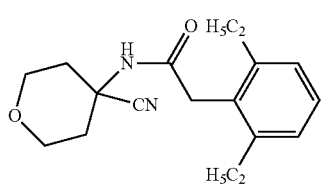

At 80° C., 7.68 g of 2,4-diethyl-6-methyl-phenylacetic acid and 9.1 ml of thionyl chloride are stirred until evolution of gas has ceased. Excess thionyl chloride is distilled off, and the residue is taken up in 40 ml of dry toluene. At from 0 to 10° C., this solution is added dropwise to 9 g of 4-amino-4-cyano-tetrahydropyran in 80 ml of dry THF admixed with 6.2 ml of triethylamine, and the mixture is stirred at room temperature for 1 h. The solution is then concentrated using a rotary evaporator, the residue is taken up in 1 N HCl in methylene chloride and the organic phase is dried and concentrated using a rotary evaporator. The residue is recrystallized from MTB-ether/n-hexane.

Yield: 10.3 g (≙ 85% of theory), m.p. 155° C.

Similarly to Example XXVII-1, Example XXVII-2 with m.p. 142° C. is obtained.

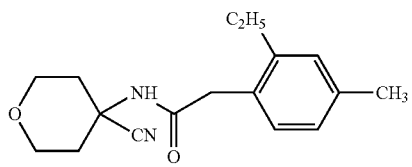 [SMILES: CCc1cc(C)ccc1CC(=O)NC1(C#N)CCOCC1]

Example I-2-a-1

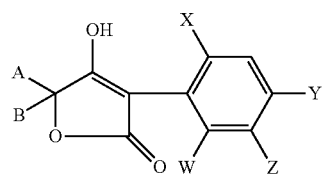

At from 0 to 10° C., 16.6 g of the compound of Example III-1, dissolved in 50 ml of anhydrous DMF, are added dropwise to 8.4 g of potassium tert-butoxide in 50 ml of anhydrous DMF, and the mixture is stirred at room temperature for 8 h. After the reaction has ended, 1000 ml of 1 N HCl are added dropwise with ice-cooling, and the mixture is stirred for 30 min. The precipitate is filtered off, washed with water and dried under reduced pressure.

Yield: 11.5 g (≙ 80% of theory), m.p. 135° C.

The following compounds of the formula (I-2-a) are obtained similarly to Example (I-2-a-1) and in accordance with the general preparation instructions (I-2-a)

| Ex. No. | W | X | Y | Z | A | B | m.p. °C. |
|---|---|---|---|---|---|---|---|
| I-2-a-2 | C$_2$H$_5$ | C$_2$H$_5$ | H | H | —(CH$_2$)$_2$—CHOCH$_3$—(CH$_2$)$_2$— | | Oil |
| I-2-a-3 | CH$_3$ | C$_2$H$_5$ | CH$_3$ | H | —(CH$_2$)$_5$— | | 223-225 |

-continued

| | | | | | | |
|---|---|---|---|---|---|---|
| I-2-a-4 | CH₃ | C₂H₅ | CH₃ | H | —(CH₂)₂—CHOCH₃—(CH₂)₂— | 175-178 |
| I-2-a-5 | CH₃ | C₂H₅ | C₂H₅ | H | —(CH₂)₂—CHOCH₃—(CH₂)₂— | Oil |

Example I-2-b-1

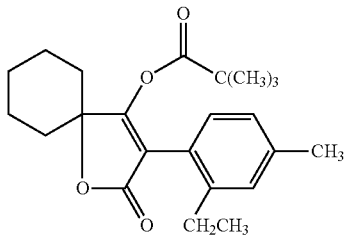 [SMILES: CCc1cc(C)ccc1C1=C(OC(=O)C(C)(C)C)C2(CCCCC2)OC1=O]

2.08 ml of triethylamine are added to 2.86 g of the compound of Example I-2-a-1 dissolved in 40 ml of dry methylene chloride (CH₂Cl₂). At 0-10° C., 1.5 g of pivaloyl chloride in 10 ml of CH₂Cl₂ are added, and the mixture is stirred at room temperature for 20 h.

The reaction solution is washed first with 10% strength citric acid and then with 1 N NaOH, dried and concentrated using a rotary evaporator, and the residue is stirred with petroleum ether.

Yield: 2.2 g (≙ 60% of theory), m.p. 110-112° C.

Example I-2-b-2

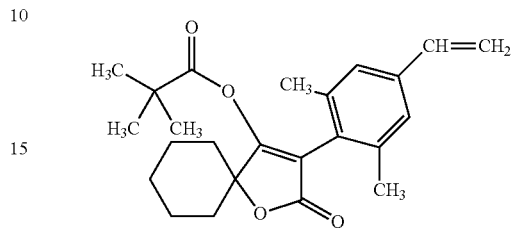

1.2 g (2.76 mmol) of the compound of Example I-2-b-2 from WO 97/02243 are initially charged in 20 ml of toluene, 3.5 g (11 mmol) of tributyl-vinyl tin, 133 mg (0.11 mmol) of Pd(PPh₃)₄ and 2 crystals of 2,6-di-t-butyl-4-methylcresol are added the mixture is boiled at reflux overnight and then concentrated using a rotary evaporator.

For purification, the crude mixture is chromatographed on silica gel, where first excess tin compounds are eluted with cyclohexane and then, by changing the mobile phase to cyclohexane/ethyl acetate (2:1), the product is eluted. Further purification was achieved by triturating the crude product with petroleum ether.

Yield: 0.46 g (44% of theory) of colourless crystals of m.p. 152-155° C.

The following compounds of the formula (I-2-b) are obtained similarly to Examples (I-2-b-1) and (I-2-b-2) and in accordance with the general preparation instructions (I-2-b)

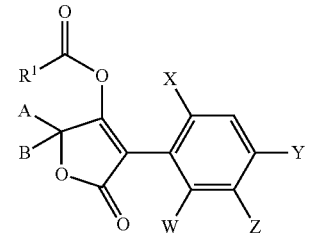

| Ex. No. | W | X | Y | Z | A | B | R¹ | m.p. ° C. |
|---|---|---|---|---|---|---|---|---|
| I-2-b-3 | H | C₂H₅ | CH₃ | H | —(CH₂)₅— | | t-C₄H₉—CH₂ | 162-164 |
| I-2-b-4 | C₂H₅ | C₂H₅ | H | H | —(CH₂)₂—CHOCH₃—(CH₂)₂— | | t-C₄H₉ | Oil |
| I-2-b-5 | CH₃ | CH₃ | CH=CH₂ | H | —(CH₂)₂—CHOCH₃—(CH₂)₂— | | t-C₄H₉ | 158-160 |
| I-2-b-6 | CH₃ | CH₃ | CH=CH₂ | H | —(CH₂)₂—CHCH₃—(CH₂)₂— | | t-C₄H₉ | 143-145 |
| I-2-b-7 | CH₃ | CH₃ | CH=CH₂ | H | —H₂C—(o-C₆H₄)—CH₂— | | t-C₄H₉ | 155-157 |
| I-2-b-8 | CH₃ | CH=CH₂ | CH₃ | H | —(CH₂)₂—CHOCH₃—(CH₂)₂— | | t-C₄H₉ | 145 |
| I-2-b-9 | CH₃ | C₂H₅ | CH₃ | H | —(CH₂)₅— | | t-C₄H₉ | 96-98 |
| I-2-b-10 | CH₃ | C₂H₅ | CH₃ | H | —(CH₂)₂—CHOCH₃—(CH₂)₂— | | t-C₄H₉ | 90-93 |
| I-2-b-11 | C₂H₅ | C₂H₅ | C₂H₅ | H | —(CH₂)₂—CHOCH₃—(CH₂)₂— | | H₅C₂—CHCH₃— | Oil |
| I-2-b-12 | H | CH₃ | CH=CH₂ | CH₃ | —(CH₂)₂—CHOCH₃—(CH₂)₂— | | s-C₄H₉ | Oil |
| I-2-b-13 | H | CH=CH₂ | CH₃ | CH₃ | —(CH₂)₂—CHOCH₃—(CH₂)₂— | | i-C₃H₇ | Oil |

Example III-1

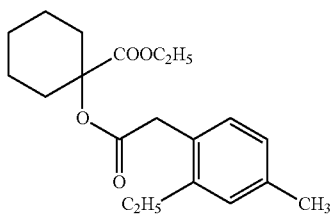

At 80° C., 8.9 g of 2-ethyl-4-methyl-phenylacetic acid in 50 ml of dry toluene and 7.3 ml of thionyl chloride are stirred until evolution of gas has ceased. Excess thionyl chloride is distilled off and the residue is taken up in 30 ml of dry toluene. At 0-10° C., this solution is added dropwise to 8.6 g of ethyl 1-hydroxy-cyclohexanecarboxylate in 50 ml of dry toluene, and the mixture is stirred at reflux for 8 h. The solution is then concentrated using a rotary evaporator.

Yield: 16.6 g (Δ 99% of theory)

The residue is used without further purification for the condensation to give Example I-2-a-1.

Example I-4-a-1

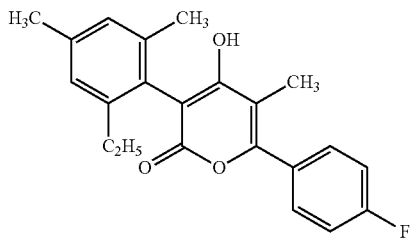 [SMILES: CCc1cc(C)cc(C)c1-c1c(O)c(C)c(-c2ccc(F)cc2)oc1=O]

2.4 g of 2-ethyl-4,6-dimethyl-2-phenyl chlorocarbonyl ketene are initially charged in ml of abs. xylene, and 1.5 g of 4-fluoropropiophenone in 20 ml of abs. xylene are added dropwise. The mixture is heated at reflux for 8 hours. The xylene solution is washed with water, dried over sodium sulphate and concentrated under reduced pressure. Chromatographic purification was carried out on silica gel using the mobile phase toluene/ethanol 20:1.

Yield: 1 g (Δ 28% of theory), of m.p. 161-162° C.

Example I-6-a-1

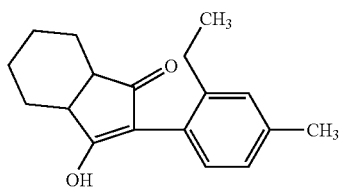 [SMILES: CCc1cc(C)ccc1C1=C(O)C2CCCCC2C1=O]

5.3 g of the compound of Example VIII-1 are initially charged in 50 ml of dry DMF and mixed with 2.95 g of potassium tert-butoxide, and the mixture is heated at 60° C. for 1 h.

The reaction solution is admixed with 100 ml of 1 N HCl and extracted with $CH_2Cl_2$, and the organic phase is dried and concentrated. The residue is purified by column chromatography (cyclohexane:ethyl acetate, 5:1).

Yield: 2.35 g (49% of theory, m.p. 148° C.

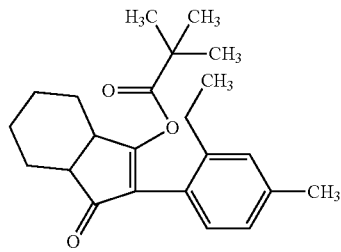 [SMILES: CCc1cc(C)ccc1C1=C(OC(=O)C(C)(C)C)C2CCCCC2C1=O]

1 g of the compound of Example I-6-a-1 is initially charged in 20 ml of dry methylene chloride and admixed with 0.77 ml of triethylamine. 0.68 ml of pivaloyl chloride is dissolved in 1 ml of methylene chloride and added dropwise with ice-cooling, and the mixture is stirred at room temperature for 2 h.

The reaction solution is extracted twice with 10% citric acid solution and the organic phase is washed twice with 1 N NaOH, dried and concentrated.

Yield: 1.2 g (92% of theory) oil.

$^1$H-NMR (500 MHz, $CDCl_3$): δ=1.1 (s, 9H, —C(CH$_3$), 2.31 (s, 3H, Ar—CH$_3$); 2.45 (q, 2H, Ar—C$\underline{H}_2$—CH$_3$) ppm

Example VIII-1

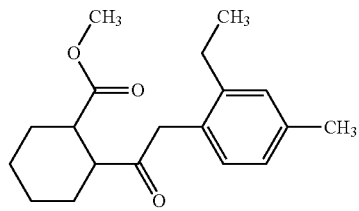 [SMILES: CCc1cc(C)ccc1CC(=O)C1CCCCC1C(=O)OC]

22.8 g of crude product from Example XXXIV-1 are initially charged in 200 ml of dry acetone and admixed with 10.9 g of potassium carbonate, and 33.6 g (14.75 ml) of methyl iodide are added dropwise. The mixture is stirred at reflux for 16 h.

The solvent is distilled off and the residue is purified by column chromatography (methylene chloride/petroleum ether: 8:1).

Yield: 3.5 g (30% of theory), oil The product is used directly for the cyclization to give Example I-6-a-1.

Example XXXIV-1

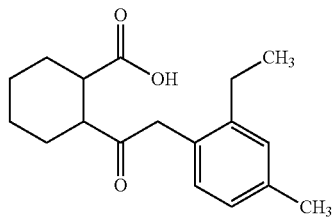 [SMILES: CCc1cc(C)ccc1CC(=O)C1CCCCC1C(=O)O]

11.2 g of monomethyl cyclohexanedicarboxylate, 5.3 ml of thionyl chloride and a drop of DMF in 50 ml of dry toluene are heated at 100° C. until evolution of gas has ceased. The solvent is concentrated.

A solution of 50 ml LDA solution in 100 ml of dry THF is, at −15° C., admixed dropwise with a solution of 17.3 g of methyl 2-ethyl-4-methyl-phenylacetate in 20 ml of dry THF, and the mixture is stirred at this temperature for 30 min.

At −15° C., a solution of the freshly prepared acid chloride described above in 15 ml of dry THF is then added dropwise.

The mixture is stirred at room temperature for 1 hour, and 150 ml of water and 40 g of ammonium chloride are then added. The intermediate is extracted with ether and the solution is concentrated. The residue is boiled at reflux with 100 g of KOH and 330 ml of water for two days.

Yield: 23.70 g (91% of theory), oil

Example XXV-1

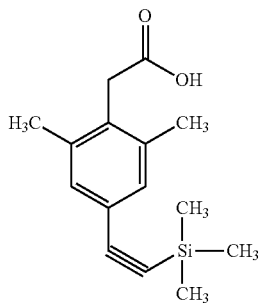

At room temperature, 4.7 g of lithium hydroxide, dissolved in 120 ml of water, are added dropwise to 26 g of the compound of Example XXX-1 in 120 ml THF, and the mixture is stirred at room temperature for 8 h.

The reaction solution is concentrated using a rotary evaporator, admixed with water and extracted with methyl tert-butyl ether.

The aqueous phase is adjusted to pH 2 using concentrated hydrochloric acid and the precipitate is filtered off with suction and dried.

Yield: 14 g (59% of theory), m.p.: 156.3° C.

Example XXX-1

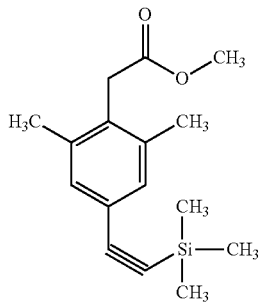

At room temperature and under an atmosphere of argon, 0.27 g of copper(I) iodide, 0.745 g of triphenylphosphine and 1 g of bis(triphenylphosphine)palladium dichloride are added with stirring to a solution of 7.32 g of methyl 2,6-dimethyl-4-bromo-phenylacetate (according to Example XXVI-1 from WO 97/02243) in 70 ml of triethylamine, and 19.7 ml of trimethylsilyl-acetylene are then added dropwise.

The reaction is monitored by gas chromatography.

Purification is carried out by silica gel column chromatography using the mobile phase petroleum ether/ethyl acetate, 20:1.

Yield: 6 g (73% of theory)

Example XXII-1

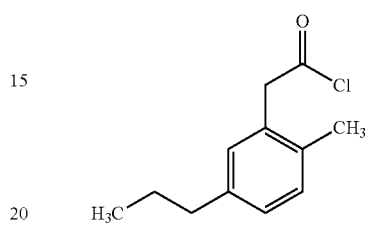

39 g of the compound of Example XXV-2 in 300 ml of thionyl chloride are stirred at 50° C. until evolution of gas has ceased.

Excess thionyl chloride is distilled off and the residue is taken up in 30 ml of dry toluene and distilled.

Yield: 37 g (87% of theory), b.p.: 90-92° C. (0.05 mbar)

Example XXV-2

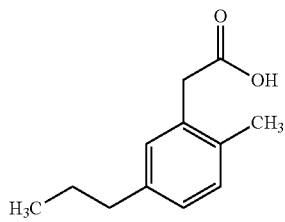

50 g of the compound of Example XXX-2 are admixed with 60 ml of ethanol, 30 ml of water and 25 g of potassium hydroxide, and the mixture is heated at reflux for hours.

After the reaction has ended, the solvent is distilled off, the residue is dissolved in water and the mixture is acidified with conc. hydrochloric acid. The precipitate is filtered off with suction, washed and dried.

Yield: 41 g (93% of theory)

Example XXX-2

Process (P)

(Process (P))

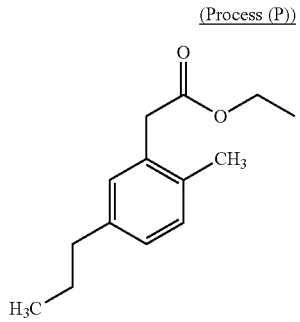 [SMILES: CCCc1ccc(C)c(CC(=O)OCC)c1]

60 g of the compound of Ex. XLfI-1 are dissolved in 600 ml of ethanol and admixed with 50 ml of concentrated hydrochloric acid, and 5 g of 10% Pd/C are added.

At 120° C., a hydrogen pressure of 150 bar is applied to the reaction mixture.

After the reaction has ended, the mixture is filtered, the solvent is distilled off and the residue is dissolved in 300 ml of methylene chloride, washed with 300 ml of water, dried and concentrated.

Yield: 51 g (91% of theory)

Example XLII-1

(Process (P))

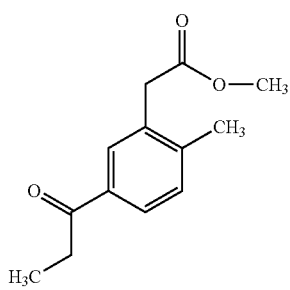

200 g of carbon disulphide and 86.7 g of aluminium chloride are initially charged. At 0° C., 50 g of methyl 2-methylphenylacetate and 28.2 g of propionyl chloride are added. The solution is stirred at reflux for 4 hours.

The solution is then poured onto 1 kg of ice-water and extracted with 500 ml of methylene chloride.

The organic phase is washed with 10% strength hydrochloric acid and then with sodium carbonate solution, dried and concentrated.

Yield: 60 g (91% of theory)

Example XXV-3

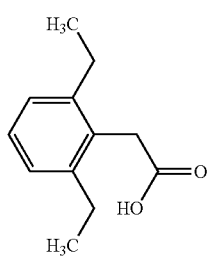

30 g of the compound of Example XXX-3 in 32 ml of methanol and 16 ml of water are admixed with 12.2 g of potassium hydroxide, and the mixture is stirred at reflux for 5 h.

The solution is concentrated and the residue is taken up in water, the mixture is washed with ethyl acetate and the aqueous phase is adjusted to pH 1 using conc. HCl.

The precipitate is filtered off with suction, washed and dried.

Yield: 25 g (99% of theory), m.p. 55-56° C.

Example XXX-3

(Process Q)

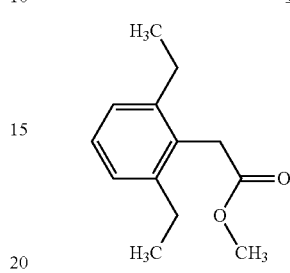

20.8 g of the compound methyl 2,6-diethyl-4-bromo-phenylacetate (according to Example XXVI-6 from WO 97/02243) are dissolved in 100 ml of methanol. 7.2 g of sodium acetate and 2 g of palladium hydroxide are added. The compound is then hydrogenated under pressure using hydrogen.

After the reaction has ended, the solution is filtered and concentrated. The residue is taken up in methylene chloride, washed with water, dried and concentrated.

Yield: 12 g (77% of theory)

USE EXAMPLES

Example A

Myzus Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the peach aphids (*Myzus persicae*) are treated by being dipped into the preparation of active compound of the desired concentration.

After the desired period of time, the kill in % is determined. 100% means that all aphids have been killed; 0% means that none of the aphids have been killed.

In this test, the compounds of Preparation Examples I-2-a-4, I-2-b-5, I-2-b-6, I-1-a-6, I-1-c-4, I-4-a-1 exhibit, at an exemplary active compound concentration of 1000 ppm, a kill of 100% after 6 days.

Example B

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Rice seedlings (*Oryza sativa*) are treated by being dipped into the preparation of active compound of the desired concentrated and are populated with the green rice leaf hopper (*Nephotettix cincticeps*) while the leaves are still moist.

After the desired period of time, the kill in % is determined. 100% means that all leaf hoppers have been killed; 0% means that none of the leaf hoppers have been killed.

In this test, the compounds of Preparation Examples I-2-b-9, I-2-a-4, I-1-a-9, I-1-a-8, I-1-a-2. I-1-a-1, I-1-a-3, I-4-a-1, exhibit, at an exemplary active compound concentration of 1000 ppm, a kill of 100% after 6 days.

Example C

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, the compounds of Preparation Examples I-2-a-3, I-2-b-8, I-2-b-6, I-1-a-2, I-1-a-3, I-1-a-21, I-4-a-1 exhibit, at an exemplary active compound concentration of 1000 ppm, a kill of 100% after 7 days.

Example D

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the owlet moth (*Plutella xylostella*) while the leaves are still moist.

After the desired period of time, the kill in % is determined. 100% means that all caterpillars have been killed: 0% means that none of the caterpillars have been killed.

In this test, the compounds of Preparation Examples I-1-a-8, I-4-a-1 exhibit, at an exemplary active compound concentration of 1000 ppm, a kill of 100% after 7 days.

Example E

Spodoptera Frugiperda Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test, the compound of Preparation Example I-2-a-3 exhibits, at an exemplary active compound concentration of 1000 ppm, a kill of 100% after 7 days.

Example F

Tetranychus Test (OP-Resistant/Dip Treatment)

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites have been killed.

In this test, the compounds of Preparation Examples I-2-a-4, I-2-b-10, I-2-b-11, I-2-b-8, I-2-b-2, I-1-a-3, I-1-a-21, I-1-c-4, I-4-a-1 exhibit, at an exemplary active compound concentration of 1000 ppm, a kill of 100% after 7 days.

Example G

Bemisia Test

Solvent: 7.5 parts by weight of dimethylformamide
Emulsifier: 2.5 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentrations.

Cotton plants (*Gossypium hirsutum*) which are infested by eggs, larvae and pupae of the white fly *Bemisia tabaci* are dipped into a preparation of active compound of the desired concentration.

After the desired period of time, the kill in % is determined. 100% means that all animals have been killed; 0% means that none of the animals have been killed.

In this test, the compounds of Preparation Examples I-2-b-9, I-2-a-4, I-2-b-10 exhibit, at an exemplary active compound concentration of 1000 ppm, a kill of 100% after 10 days.

Example H

Post-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amount of active compound desired is applied in 1000 l of water/ha.

After three weeks, the degree of damage to the plants is rated in % damage in comparison to the development of the untreated control.

The figures denote:
0%=no effect (like untreated control)
100%=total destruction

Example I

Pre-Emergence Test

Solvent: 5 parts by weight of acetone
Emulsifier: 1 part by weight of alkyaryl polyglycol ether To produce a suitable preparation of active compound, 1 part by weight of active compound is mixed with the stated amount of solvent, the stated amount emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated controls.

The figures denote:
0%=no effect (like untreated control)
100%=total destruction

| Post-emergence | g ai/ha | Wheat | Cotton | *Alopecurus* | *Avena fatua* | *Lolium* | *Sorghum* |
|---|---|---|---|---|---|---|---|
| Ex. I-2-a-4 | 60 | 0 | 0 | 95 | 80 | 95 | 80 |

| Post-emergence | g ai/ha | Sugar beet | *Alopecurus* | *Avena fatua* | *Digitaria* | *Lolium* | *Setaria* | *Ipomoea* | *Polygonum* |
|---|---|---|---|---|---|---|---|---|---|
| Ex. I-1-a-21 | 125 | 0 | 100 | 90 | 100 | 95 | 99 | 70 | — |
| Ex. I-1-c-4 | 60 | 10 | 90 | 90 | 95 | — | 100 | — | 70 |

| Post-emergence | g ai/ha | Soya bean | *Digitaria* | *Lolium* | *Setaria* | *Sorghum* | *Galium* |
|---|---|---|---|---|---|---|---|
| Ex. I-1-a-5 | 125 | 10 | 90 | — | 100 | 95 | 80 |
| Ex. I-1-a-3 | 125 | — | 80 | 70 | 90 | — | 80 |

| Post-emergence | g ai/ha | Sugar beet | Oilseed rape | *Digitaria* | *Lolium* | *Setaria* | *Sorghum* | *Galium* |
|---|---|---|---|---|---|---|---|---|
| Ex. I-I-a-2 | 125 | 0 | 0 | 80 | 70 | 95 | 80 | 80 |

| Post-emergence | g ai/ha | Sugar beet | Cotton | *Alopecurus* | *Avena fatua* | *Digitaria* | *Setaria* |
|---|---|---|---|---|---|---|---|
| Ex. I-1-a-9 | 15 | 10 | 0 | 100 | 95 | 95 | 100 |

| Post-emergence | g ai/ha | Sugar beet | Cotton | *Digitaria* | *Echinochloa* | *Setaria* | *Sorghum* |
|---|---|---|---|---|---|---|---|
| Ex. I-1-a-8 | 60 | 10 | 0 | 95 | 100 | 100 | 95 |

| Post-emergence | g ai/ha | *Digitaria* | *Lolium* | *Setaria* | *Sorghum* |
|---|---|---|---|---|---|
| Ex. I-1-a-6 | 125 | 95 | 80 | 95 | 100 |

| Post-emergence | g ai/ha | Wheat | Soya bean | Cotton | *Digitaria* | *Lolium* | *Setaria* |
|---|---|---|---|---|---|---|---|
| Ex. I-2-b-12 | 125 | — | 0 | 0 | 95 | 90 | 95 |
| Ex. I-2-b-13 | 125 | 10 | 0 | 0 | 80 | 70 | 95 |

| Post-emergence | g ai/ha | Wheat | Sugar beet | Cotton | *Digitaria* | *Echinochloa* | *Setaria* | *Sorghum* |
|---|---|---|---|---|---|---|---|---|
| Ex. I-4-a-1 | 125 | 20 | 0 | 0 | 100 | 90 | 95 | 90 |

| Post-emergence | g ai/ha | Wheat | *Lolium* | *Cassia* | *Solanum* | *Viola* |
|---|---|---|---|---|---|---|
| Ex. I-2-b-10 | 125 | 10 | 80 | 95 | 80 | 90 |

| Pre-emergence | g ai/ha | Wheat | Maize | Sugar beet | Soya bean | *Alopecurus* | *Avena fatua* | *Bromus* | *Lolium* | *Setaria* |
|---|---|---|---|---|---|---|---|---|---|---|

-continued

| | | | | | | | | | | |
|---|---|---|---|---|---|---|---|---|---|---|
| Ex. I-2-a-4 | 125 | — | 5 | 0 | 0 | 100 | 80 | 70 | 100 | 100 |
| Ex. I-1-a-8 | 60 | 0 | 10 | 0 | 0 | 100 | 90 | 100 | 100 | 100 |

| Pre-emergence | g ai/ha | Alopecurus | Avena fatua | Digitaria | Echinochloa | Lolium | Setaria |
|---|---|---|---|---|---|---|---|
| Ex. I-1-a-3 | 125 | 100 | 95 | 100 | 100 | 100 | 100 |

| Pre-emergence | g ai/ha | Alopecurus | Avena fatua | Echinochloa |
|---|---|---|---|---|
| Ex. I-1-a-6 | 60 | 90 | 80 | 90 |

| Pre-emergence | g ai/ha | Sugar beet | Soya bean | Alopecurus | Digitaria | Lolium | Setaria | Veronica |
|---|---|---|---|---|---|---|---|---|
| Ex. I-4-a-1 | 125 | 0 | 0 | 100 | 100 | 100 | 100 | 95 |
| Ex. I-1-a-21 | 125 | 0 | 0 | 100 | 100 | 100 | 100 | 100 |
| Ex. I-1-a-9 | 125 | 0 | 0 | 100 | 100 | 100 | 100 | 90 |

| Pre-emergence | g ai/ha | Wheat | Soya bean | Alopecurus | Echinochloa | Lolium | Setaria | Chenopodium |
|---|---|---|---|---|---|---|---|---|
| Ex. I-1-a-5 | 60 | 0 | 0 | 100 | 100 | 100 | 100 | 70 |

| Pre-emergence | g ai/ha | Soya bean | Alopecurus | Bromus | Cyperus | Digitaria | Lolium | Setaria | Abutilo |
|---|---|---|---|---|---|---|---|---|---|
| Ex. I-1-c-4 | 125 | 20 | 95 | 100 | 100 | 100 | 100 | 100 | 70 |

Example J

Critical Concentration Test/Soil Insects—Treatment of Transgenic Plants

Test insects: *Diabrotica balteata*—larvae in soil
Solvent: 7 parts by weight of acetone
Emulsifier: 1 part by weight of alkylaryl polyglycol ether To produce a suitable preparation of active compound, I part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is almost irrelevant, only the amount by weight of active compound per volume unit of soil, which is stated in ppm (mg/l), matters. The soil is filled into 0.25 l pots and these are allowed to stand at 20° C.

Immediately after preparation, 5 pre-germinated maize corns of the variety YIELD GUARD (trade mark of Monsanto Comp., USA) are placed into each pot. After 2 days, the test insects are placed into the treated soil. After a further 7 days, the efficacy of the active compound is determined by counting the maize plants that have emerged (1 plant=20% efficacy).

Example K

*Heliothis Virescens* Test—Treatment of Transgenic Plants

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya bean shoots (*glycine max*) of the variety Roundup Ready (trade mark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

What is claimed is:

1. A compound of the formula (I-6-A) and/or (I-6-B)

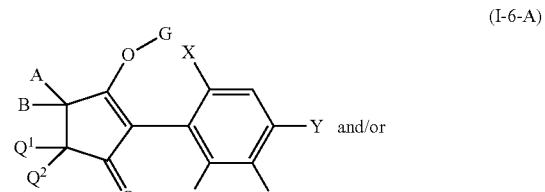

and/or

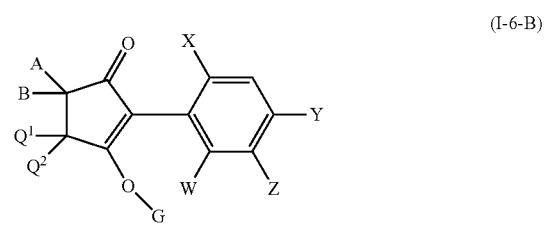

in which

W represents methyl,

X represents $C_1$-$C_6$-alkyl, $C_2$-$C_6$-alkenyl or ethinyl,

Y represents hydrogen, methyl, ethyl, i-propyl, $C_2$-$C_6$-alkenyl or ethinyl,

Z represents hydrogen, $C_1$-$C_6$-alkyl, $C_2$-$C_6$-alkenyl or ethinyl, with the proviso that at least one of the radicals X, Y or Z represents a chain having at least two carbon atoms and with the further proviso that X is not ethyl when Z is hydrogen and Y is methyl, B represents hydrogen, A and $Q^1$ together represent $C_4$-alkanediyl, $Q^2$ represents hydrogen, and G represents hydrogen (a) or

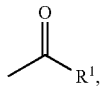
(b)

in which

R¹ represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl or cyclohexyl or cyclopropyl which is optionally monosubstituted by fluorine, chlorine, methyl or methoxy, or represents phenyl which is optionally monosubstituted by fluorine, chlorine, bromine, cyano, nitro, methyl, methoxy, trifluoromethyl or trifluoromethoxy.

2. A process for preparing a compound of the formula (I), wherein (A) a compound of the formula (I-6-a)

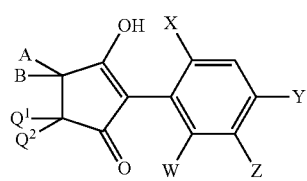
(I-6-a)

in which A, B, $Q^1$, $Q^2$, W, X, Y and Z are each as defined in claim 1, is obtained by intramolecular cyclization of a ketocarboxylic ester of the formula (VIII)

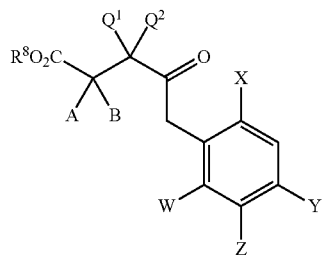
(VIII)

in which

A, B, $Q^1$, $Q^2$, W, X, Y and Z are each as defined in claim 1, and

R⁸ represents alkyl, if appropriate in the presence of a diluent and if appropriate in the presence of a base; or (B) a compound of the formula (I-6-a) or (I-6-b)

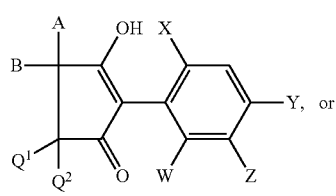
(I-6-a)

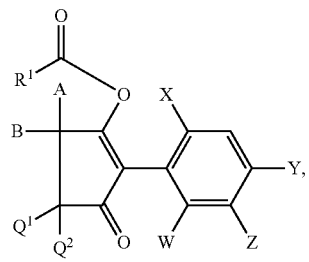
(I-6-b)

in which A, B, D, G, $Q^1$, $Q^2$, W, X, Y and Z are each as defined in claim 1, where one or at most two radicals X, Y or Z represent
$R^{22}$—C≡C— or

and $R^{22}$ represents hydrogen, is obtained by reacting a compound of the formula (I-6' (a-g))

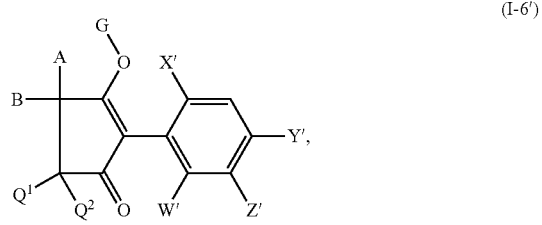
(I-6')

in which A, B, D, G, $Q^1$, W', X', Y' and Z' are each as defined in claim 1, and $Q^2$ is as defined above, and where the apostrophe ' means that one or at most two radicals X, Y and Z in this process represent chlorine, bromine or iodine, with the proviso that the other radicals X, Y and Z do not represent alkenyl or alkinyl with a silylacetylene of the formula (X-a) or a vinylstannane of the formula (X-b)

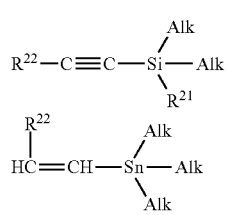
(X-a)

in which

Alk represents $C_1$-$C_4$-alkyl, $R^{21}$ represents $C_1$-$C_4$-alkyl or phenyl, and $R^{22}$ represents hydrogen, in the presence of a solvent, if appropriate in the presence of a base and a catalyst; or (C) a compound of the formula (I-6-b) shown above in which A, B, D, $Q^1$, $Q^2$, $R^1$, W, X, Y and Z are each as defined in claim 1 is obtained by reacting a compound of the formula (I-6-a) shown above in which A, B, D, $Q^1$, $Q^2$, W, X, Y and Z are each as defined in claim 1,
(α) with an acid halide of the formula (XI)

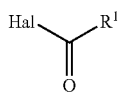  (XI)

in which
$R^1$ is as defined in claim 1 and
Hal represents halogen
or
(β) with a carboxylic anhydride of the formula (XII)

$R^1$—CO—O—CO—$R^1$  (XII)

in which $R^1$ is as defined in claim 1,
if appropriate in the presence of a diluent and if appropriate in the presence of an acid binder.

3. A compound of the formula (I) according to claim 1, wherein
W represents methyl,
X represents $C_1$-$C_4$-alkyl, $C_2$-$C_4$-alkenyl or ethinyl,
Y represents hydrogen, methyl, ethyl, i-propyl, $C_2$-$C_4$-alkenyl or ethinyl,
Z represents hydrogen, $C_1$-$C_4$-alkyl, $C_2$-$C_4$-alkenyl or ethinyl,
with the proviso that at least one of the radicals X, Y or Z represents a chain having at least two carbon atoms, where at most only one of the radicals X, Y or Z may represent $C_2$-$C_4$-alkenyl or ethinyl, and with the further proviso that X is not ethyl when Z is hydrogen and Y is methyl,
B represents hydrogen or $C_1$-$C_4$-alkyl,
A and $Q^1$ together represent $C_4$-alkanediyl,
$Q^2$ represents hydrogen, and
G represents hydrogen (a)

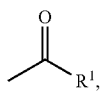  (b)

in which
$R^1$ represents $C_1$-$C_6$-alkyl, $C_2$-$C_6$-alkenyl, $C_2$-$C_2$-alkoxy-$C_1$-alkyl, $C_1$-$C_2$-alkylthio-$C_1$-alkyl or cyclohexyl or cyclopropyl which is optionally monosubstituted by fluorine, chlorine, methyl or methoxy, or represents phenyl which is optionally monosubstituted by fluorine, chlorine, bromine, cyano, nitro, methyl, methoxy, trifluoromethyl or trifluoromethoxy.

4. A compound of the formula (I) according to claim 1, wherein
W represents methyl,
X represents methyl, ethyl, n-propyl, iso-propyl, vinyl or ethinyl,
Y represents hydrogen, methyl, ethyl, i-propyl, vinyl or ethinyl,
Z represents hydrogen, methyl, ethyl, n-propyl, i-butyl, vinyl or ethinyl,
with the proviso that at least one of the radicals X, Y or Z represents a chain having at least two carbon atoms, where at most only one of the radicals X, Y or Z may represent vinyl or ethinyl, and with the further proviso that X is not ethyl when Z is hydrogen and Y is methyl,
B represents hydrogen, methyl or ethyl,
A and $Q^1$ together represent $C_4$-alkanediyl,
$Q^2$ represents hydrogen, and
G represents hydrogen (a) or

  (b)

in which
$R^1$ represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl or cyclohexyl or cyclopropyl which is optionally monosubstituted by fluorine, chlorine, methyl or methoxy,
represents phenyl which is optionally monosubstituted by fluorine, chlorine, bromine, cyano, nitro, methyl, methoxy, trifluoromethyl or trifluoromethoxy.

5. A pesticide or herbicide that comprises at least one compound of the formula (I) according to claim 1.

6. A method for controlling animal pests comprising allowing a compound of the formula (I) according to claim 1 to act on pests and/or their habitat.

7. A method of controlling undesirable vegetation comprising using a compound of formula (I) according to claim 1.

8. A process for preparing a pesticides or herbicide comprising mixing a compound of the formula (I) according to claim 1 with extenders and/or surfactants.

* * * * *